United States Patent
Graeber et al.

(10) Patent No.: US 12,213,977 B2
(45) Date of Patent: Feb. 4, 2025

(54) METHODS AND COMPOSITIONS FOR TREATING MELANOMA

(71) Applicant: THE REGENTS OF THE UNIVERSITY OF CALIFORNIA, Oakland, CA (US)

(72) Inventors: Thomas G. Graeber, Los Angeles, CA (US); Jennifer Tsoi, Los Angeles, CA (US); Antoni Ribas, Los Angeles, CA (US); Lidia Robert, Los Angeles, CA (US); Nicolaos Palaskas, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 207 days.

(21) Appl. No.: 16/625,075

(22) PCT Filed: Jun. 27, 2018

(86) PCT No.: PCT/US2018/039822
§ 371 (c)(1),
(2) Date: Dec. 20, 2019

(87) PCT Pub. No.: WO2019/006005
PCT Pub. Date: Jan. 3, 2019

(65) Prior Publication Data
US 2020/0163966 A1    May 28, 2020

Related U.S. Application Data

(60) Provisional application No. 62/650,051, filed on Mar. 29, 2018, provisional application No. 62/525,969, filed on Jun. 28, 2017.

(51) Int. Cl.
| *A61K 31/517* | (2006.01) |
| *A61K 31/437* | (2006.01) |
| *A61K 35/17* | (2015.01) |
| *A61K 45/06* | (2006.01) |
| *C07K 16/28* | (2006.01) |

(52) U.S. Cl.
CPC .......... *A61K 31/517* (2013.01); *A61K 31/437* (2013.01); *A61K 35/17* (2013.01); *C07K 16/2818* (2013.01); *A61K 45/06* (2013.01)

(58) Field of Classification Search
CPC ...... A61P 35/00; A61K 31/437; A61K 31/517
See application file for complete search history.

(56) References Cited

U.S. PATENT DOCUMENTS

| 2007/0154889 A1 | 7/2007 | Wang | |
| 2011/0177042 A1* | 7/2011 | Herlyn | C12N 5/0626 |
| | | | 514/557 |
| 2012/0095078 A1 | 4/2012 | Ronai | |
| 2015/0306080 A1* | 10/2015 | Zon | A61K 31/42 |
| | | | 514/300 |
| 2015/0307617 A1 | 10/2015 | Du et al. | |
| 2018/0120336 A1* | 5/2018 | Van Tine | A61K 31/198 |
| 2021/0113503 A1* | 4/2021 | Schultz | A61K 31/437 |

FOREIGN PATENT DOCUMENTS

| WO | WO-2012027716 A1 * | 3/2012 | ........ A61K 31/404 |
| WO | WO 2013152039 | 10/2013 | |
| WO | WO 2015084749 | 6/2015 | |
| WO | WO 2016196201 | 12/2016 | |
| WO | WO-2017058007 A1 * | 4/2017 | ........ A61K 31/167 |
| WO | WO-2018218087 A1 * | 11/2018 | ........ A61K 31/015 |

OTHER PUBLICATIONS

Jiao (European Journal of Medicinal Chemistry vol. 90 pp. 170-183 published 2015). (Year: 2015).*
Lachaier (Anticancer Research vol. 34 pp. 6417-6422. Published 2014). (Year: 2014).*
Mascarenhas (Pigment Cell Melanoma Res. vol. 23 pp. 225-23 published 2010). (Year: 2010).*
Bracelente (Oncotarget vol. 7 pp. 41142-41153 published 2016). (Year: 2016).*
Dudley (Journal of Clinical Oncology vol. 26 pp. 5233-5239 published 2008). (Year: 2008).*
Cheli (Oncogene vol. 30 pp. 2307-2318 published 2011). (Year: 2011).*
Yang (Cell vol. 156 pp. 317-331 published 2014). (Year: 2014).*
Revez (International Journal of Radiation Oncology Biol. Physics vol. 29 pp. 403-406. Published 1994) (Year: 1994).*
Kobayashi (Cancer Letters vol. 85 pp. 165-169. Published 1994). (Year: 1994).*
Berrocal et al., "Melanoma: Diagnosis, Staging, and Treatment. Consensus group recommendations" *Advances in Therapy* 2014, 31, 945-960.
Partial Supplementary European Search Report in Corresponding European Application No. 18823414.0, dated Mar. 12, 2021.
Wagner et al., "Diagnostic dilemma: late presentation of amelanotic BRAF-negative metastatic malignant melanoma resembling clear cell sarcoma: a case report" *Diagnostic Pathology* 2013, 8(192), 4 pages.
Eroglu, Z., and Ribas, A., "Combination therapy with BRAF and MEK inhibitors for melanoma: latest evidence and place in therapy" *Therapeutic Advances in Medical Oncology* 2016, 8(1), 48-56.
Hugo et al., "Non-genomic and Immune Evolution of Melanoma Acquiring MAPKi Resistance" *Cell* 2015, 162, 1271-1285.

(Continued)

*Primary Examiner* — Clinton A Brooks
*Assistant Examiner* — George W Kosturko
(74) *Attorney, Agent, or Firm* — Norton Rose Fulbright US LLP

(57) ABSTRACT

The current methods and compositions provide for a novel therapeutic method for treating patients diagnosed with melanoma, especially those that have become resistant to certain other therapies. Accordingly, certain aspects of the disclosure relate to a method for treating melanoma in a subject, the method comprising administering a composition comprising a ferroptosis-inducing agent or other dedifferentiated melanoma-targeting agent to the subject.

12 Claims, 25 Drawing Sheets

(56) References Cited

OTHER PUBLICATIONS

International Search Report and Written Opinion in corresponding application No. PCT/US2018/39822, dated Dec. 14, 2018.
Luke et al., "Targeted agents and immunotherapies: optimizing outcomes in melanoma" *Nature reviews. Clinical oncology* 2017, 14(8), 20 pages.
Müller et al., "Low MITF/AXL ratio predicts early resistance to multiple targeted drugs in melanoma" *Nat Commun.* 2014, 5(5712), 1-15.
Nazarian et al., "Melanomas acquire resistance to B-RAF(V600E) inhibition by RTK or N-RAS upregulation" *Nature* 2010, 468(7326), 11 pages.
Søndergaard et al., "Differential sensitivity of melanoma cell lines with BRAF V600E mutation to the specific Raf inhibitor PLX4032" *Journal of Translational Medicine* 2010, 8(39), 11 pages.
Wong et al., "Antitumor activity of the ERK inhibitor SCH722984 against BRAF mutant, NRAS mutant and wild-type melanoma" *Molecular Cancer* 2014, 13(194), 15 pages.

* cited by examiner

METHODS AND COMPOSITIONS FOR TREATING MELANOMA

CROSS-REFERENCE TO RELATED APPLICATIONS

This application is a national phase application under 35 U.S.C. § 371 of International Application No. PCT/US2018/039822, filed Jun. 27, 2018, which claims the benefit of priority of U.S. Provisional Patent Application No. 62/525,969, filed Jun. 28, 2017, and U.S. Provisional Patent Application No. 62/650,051, filed Mar. 29, 2018, which are hereby incorporated by reference in their entirety.

STATEMENT OF GOVERNMENT SUPPORT

This invention was made with government support under Grant Numbers CA009120, CA168585, and CA197633 awarded by the National Institutes of Health. The government has certain rights in the invention.

This invention was made with Government support under CA009120 and CA168585, awarded by the National Institutes of Health. The Government has certain rights in the invention.

BACKGROUND

1. Field of the Invention

Embodiments are directed generally to biology and medicine. In certain aspects methods involve treating cancer patients and determining an optimal therapeutic regimen for the cancer patient. In additional embodiments there are therapeutic compositions and the use of such compositions for the treatment of melanoma.

2. Description of Related Art

Melanoma is a highly aggressive type of skin cancer that arises from melanocytes, the pigment producing cells in the body. The discovery that approximately half of melanomas are driven through $BRAF_{V600}$ mutations and advances in tumor immunology have translated to new targeted and immune therapies with impressive response rates and significantly improved survival (Luke et al., 2017). However, for all these treatment modalities there remain patients that do not respond or ultimately relapse.

A source of cross-resistance to both therapeutic approaches is from differentiation plasticity of melanoma cells. This plasticity could be attributed to its embryonic history as melanocytes are derived from the neural crest, a transient, migratory, and multi-potent population of cells that can differentiate into diverse cell types (Sauka-Spengler and Bronner-Fraser, 2008). During acquired resistance to BRAF inhibition (BRAFi), melanoma cells can downregulate MITF, the master regulator of melanocyte differentiation, and upregulate receptor tyrosine kinases (RTK) such as AXL, EGFR, and PDGFRβ (Girotti et al., 2013; Müller et al., 2014; Nazarian et al., 2010). Low baseline levels of MITF and high levels of AXL were also predictive of intrinsic resistance to MAPK pathway inhibition (MAPKi) (Konieczkowski et al., 2014; Müller et al., 2014). In support of this, MITF loss and RTK upregulation has been observed in patient tumors during disease progression on MAPKi therapy (Hugo et al., 2015; Müller et al., 2014; Tirosh et al., 2016). Melanoma cells also dedifferentiate in response to pro-inflammatory signaling, as has been demonstrated in mouse models, which in turn can promote immunotherapy resistance (Landsberg et al., 2012). CD8+ T cells isolated from patient tumors were found to frequently recognize melanocyte lineage antigens (Kawakami et al.). Thus, in melanoma models with infiltrating T cells recognizing melanocytic antigens, dedifferentiation provides a mechanism to escape immune recognition. Additionally, inflammatory MITF-low melanomas were shown to have greater recruitment of myeloid cells (Riesenberg et al., 2015), which could support tumor growth or immune suppression (Hugo et al., 2015; Soudja et al., 2010).

In conclusion, dedifferentiated melanoma in patients presents a therapeutic challenge, since these patients may become or may already be resistant to current therapies for melanoma. Therefore, there is a need in the art for novel therapeutic regimens for these patients.

SUMMARY OF THE DISCLOSURE

The current methods and compositions provide for a novel therapeutic method for treating patients diagnosed with melanoma, especially those that have become resistant to certain other therapies. Accordingly, certain aspects of the disclosure relate to a method for treating melanoma in a subject, the method comprising administering a composition comprising a ferroptosis-inducing agent or other dedifferentiated melanoma-targeting agent to the subject.

Further aspects of the disclosure relate to a method for classifying a subject diagnosed with melanoma, the method comprising: a. obtaining a biological sample from the subject; and b. detecting the expression level of one or more biomarkers in the biological sample from the subject. In some embodiments, the biomarker comprises one or more of: MITF, SOX10, SOX9, SMAD3, CTNNB2, AXL, NGFR, EGFR, and ERBB3. In some embodiments, the biomarker comprises one or more of AJUBA, TOR4A, MARCH4, ZDHHC2, ZNF467, ZNF185, ZIC2, VASN, UCP2, GALNT6, TNFAIP2, TNFSF18, TMEM40, TMEM200A, TMEM184A, TBL1X, TRERF1, TOX, TBC1D2, SFN, SAMD12, SAMD11, SOX9, SLC8A1, SLC38A4. SLC16A14, SCNSA, SCNN1A, SH3RF2, SERPINB7, SLPI, SECTM1, RUNX2, ARHGAP29, REN, PAWR, PSG9, PSG5, PSG4, PBX1, PLAGL1, PHLDB2, PLEKHA6, PDGFC, PLAU, PKP2, PLAC8, PADI3, PITX1, NUAK1, NTNG1, NMT2, MYEOV, MICAL2, MGST1, MECOM, LYPD6B, LAMA5, KISS1, KRT86, KRT81, KRT80, KRT8, KRT7, KRT18, JUP, IL7R, IL4R, IRS1, IGFN1, HES7, GDA, GLIS2, GATA2, GPRC5C, GPRC5A, FMNL1, FOXA1, FLNC, FERMT1, FAT4, FAM196B, ELFN2, EGFR, DSE, DMBT1, DIO2, DOCK2, CYP2S1, CRIM1, CDK15, CORO6, COLEC10, CCDC88C, CCDC69, F3, F2RL1, CLU, CDYL2, CITED2, CARD11, CPA4, CREB3L1, CNN1, CALB2, CDH4, BTBD11, BDNF, BASP1, BNC1, ATP8B1, ABCG2, ARMC4, ANKRD1, AR, AMIGO2, ADAMTSL1, and ACSL5. In some embodiments, the biomarker comprises one or more of VIT, VIPR1, VEGFC, TWIST2, TNFRSF12A, TPM1, TPBG, TLE4, TOX2, TLR4, THSD4, STX1A, SYT1, SYNPO, STRA6, STC2, SPRED3, SPOCD1, SPOCK1, SLC2A1, SLC16A2, SLC14A1, SLC12A8, SMAGP, SLIT2, SDK1, STAC, SLFN11, S100A2, ROBO4, RAB27B, PKIA, PRSS23, PAPPA, PRDM1, KCNMA1, KCNN4, PODXL, PDGFRB, PLAUR, PXDN, PTX3, NMNAT2, NRP1, NGEF, NEGR1, NRG1, NTN4, MT2A, MT1E, MPP4, LOXL2, LDOC1, LAMB3, JUN, IL31RA, IL11, IL1B, ITGA3, ITGA2, IGFBP6, ID1, INHBA, HRH1, GAS6, GLIPR1, GFRA1, GATA3, GPR176, FZD2, FJX1, FOSL1, FOXF1, FBLIM1, FLNB, FAM83G, FAM20C, FAM171A1, FAM155A, ERRFI1, EFNB2, DPYD, DKK1, DOCKS, CYR61, CLMP, COL13A1, COL12A1, COL5A1, F2RL2, C16orf45, C15orf52, C12orf75, CD163L1, CAV1, CARD10, CLCF1, CDH13, BMP2, AXL, ABCC3, ARNTL2, ANTXR2, ANXA1, AKR1C3, and ARL4C.

Further aspects of the disclosure relate to a method of diagnosing melanoma in a subject, said method comprising: a. obtaining a biological sample from the subject; b. detecting the expression level of one or more biomarkers in the biological sample from the subject; c. diagnosing the patient with melanoma when the expression level of the one or more biomarkers is differentially expressed, compared to a control.

Further aspects of the disclosure relate to a method for inducing ferroptosis in a subject diagnosed with melanoma, the method comprising administering a composition comprising a ferroptosis-inducing agent or other dedifferentiated melanoma-targeting agent to the subject. Further aspects of the disclosure relate to a method for inducing ferroptosis in resistant melanoma cells, the method comprising administering a composition comprising a ferroptosis-inducing agent to the subject; wherein the resistant melanoma cells are resistant to a prior treatment as described herein.

Yet further aspects of the disclosure relate to a composition comprising a ferroptosis-inducing agent or other dedifferentiated melanoma-targeting agent and one or more of a MAPK inhibitor, an immunotherapy, or an additional agent. Yet further aspects of the disclosure relate to treating a subject as defined herein with a composition of the disclosure.

In some embodiments, the method further comprises administration of an additional therapy. In some embodiments, the additional therapy comprises an immunotherapy. In some embodiments, the immunotherapy comprises adoptive T cell transfer. In some embodiments, the additional therapy comprises an immune checkpoint inhibitor. In some embodiments, the immune checkpoint inhibitor comprises one or both of an anti-PD-1 antibody and an anti-CTLA4 antibody.

In some embodiments, the additional therapy comprises a MAPK inhibitor. In some embodiments, the MAPK inhibitor comprises a B-Raf inhibitor. In some embodiments, the additional therapy comprises one or more therapies described herein.

In some embodiments, the ferroptosis-inducing agent comprises one or more of erastin, sulfazine, and RSL3. In some embodiments, cell death-inducing agents comprise one or more of Ki8751 (a VEGFR2 kinase inhibitor), SGX-523 (a c-Met kinase inhibitor (RTK inhibitor)), AZD7762 (a Chk1 & Chk2 inhibitor-Checkpoint kinase 1 and 2 inhibitor), KW-2449 (a multi-kinase inhibitor—a FLT3 inhibitor), NVP-TAE684 (a ALK kinase inhibitor), AZD4547 (a Pan FGFR kinase inhibitor (RTK inhibitor)), TG-101348 (a JAK2 kinase inhibitor), bleomycin A2 (a DNA damaging agent), axitinib (a VEGFR kinase inhibitor), cytochalasin B (an inhibitor of actin polymerization), dasatinib (a Src kinase inhibitor), SNX-2112 (an HSP90 inhibitor), Semagacestat (a γ-secretase inhibitor), CHIR-99021 (a GSK-3 inhibitor), B02 (a RAD51 inhibitor), olaparib (a PARP inhibitor), silmitasertib (a casein kinase II (CK2) inhibitor), tanespimycin (a HSP90 inhibitor), nintedanib (a tyrosine-kinase inhibitor, targeting VEGFR, FGFR, and PDGFR), ML031 (a Sphingosine-1-phosphate (S1P) agonist), canertinib (a ErbB family inhibitor (EGFR, HER-2, ErbB-4)), SMER-3 (a MET30 Antagonist), BCL-LZH-4 (a inhibitor of Bcl-2 family proteins), SN-38 (a topoisomerase inhibitor), tamatinib (an inhibitor of immunoglobulin E (IgE)- and IgG-mediated activation of Fc receptor signaling), ML334 diastereomer (a small molecule inhibitor of the Keap1-Nrf2 interaction), analogues, salts and derivatives thereof. In some embodiments, one or more of these cell death-inducing agents are excluded.

In some embodiments, the melanoma cells are dedifferentiated or have a neural crest phenotype. In some embodiments, the melanoma cells have an undifferentiated phenotype. In some embodiments, the melanoma cells have one or more compared to a control: reduced expression MITF, reduced expression of SOX10, increased expression of SOX9, increased expression of SMAD3, reduced expression of CTNNB1, increased expression of AXL, reduced expression of NGFR, increased expression of EGFR, and reduced expression of ERBB3. In some embodiments, the subject has been determined to have differential expression of one or more of MITF, SOX10, SOX9, SMAD3, CTNNB2, AXL, NGFR, EGFR, and ERBB3, compared to a control. n some embodiments, the subject has been determined to have differential expression of one or more of AJUBA, TOR4A, MARCH4, ZDHHC2, ZNF467, ZNF185, ZIC2, VASN, UCP2, GALNT6, TNFAIP2, TNFSF18, TMEM40, TMEM200A, TMEM184A, TBL1X, TRERF1, TOX, TBC1D2, SFN, SAMD12, SAMD11, SOX9, SLC8A1, SLC38A4. SLC16A14, SCN5A, SCNN1A, SH3RF2, SERPINB7, SLPI, SECTM1, RUNX2, ARHGAP29, REN, PAWR, PSG9, PSG5, PSG4, PBX1, PLAGL1, PHLDB2, PLEKHA6, PDGFC, PLAU, PKP2, PLAC8, PADI3, PITX1, NUAK1, NTNG1, NMT2, MYEOV, MICAL2, MGST1, MECOM, LYPD6B, LAMA5, KISS1, KRT86, KRT81, KRT80, KRT8, KRT7, KRT18, JUP, IL7R, IL4R, IRS1, IGFN1, HES7, GDA, GLIS2, GATA2, GPRC5C, GPRC5A, FMNL1, FOXA1, FLNC, FERMT1, FAT4, FAM196B, ELFN2, EGFR, DSE, DMBT1, DIO2, DOCK2, CYP2S1, CRIM1, CDK15, CORO6, COLEC10, CCDC88C, CCDC69, F3, F2RL1, CLU, CDYL2, CITED2, CARD11, CPA4, CREB3L1, CNN1, CALB2, CDH4, BTBD11, BDNF, BASP1, BNC1, ATP8B1, ABCG2, ARMC4, ANKRD1, AR, AMIGO2, ADAMTSL1, and ACSL5 compared to a control. n some embodiments, the subject has been determined to have differential expression of one or more of VIT, VIPR1, VEGFC, TWIST2, TNFRSF12A, TPM1, TPBG, TLE4, TOX2, TLR4, THSD4, STX1A, SYT1, SYNPO, STRA6, STC2, SPRED3, SPOCD1, SPOCK1, SLC2A1, SLC16A2, SLC14A1, SLC12A8, SMAGP, SLIT2, SDK1, STAC, SLFN11, S100A2, ROBO4, RAB27B, PKIA, PRSS23, PAPPA, PRDM1, KCNMA1, KCNN4, PODXL, PDGFRB, PLAUR, PXDN, PTX3, NMNAT2, NRP1, NGEF, NEGR1, NRG1, NTN4, MT2A, MT1E, MPP4, LOXL2, LDOC1, LAMB3, JUN, IL31RA, IL11, IL1B, ITGA3, ITGA2, IGFBP6, ID1, INHBA, HRH1, GAS6, GLIPR1, GFRA1, GATA3, GPR176, FZD2, FJX1, FOSL1, FOXF1, FBLIM1, FLNB, FAM83G, FAM20C, FAM171A1, FAM155A, ERRFI1, EFNB2, DPYD, DKK1, DOCKS, CYR61, CLMP, COL13A1, COL12A1, COL5A1, F2RL2, C16orf45, C15orf52, C12orf75, CD163L1, CAV1, CARD10, CLCF1, CDH13, BMP2, AXL, ABCC3, ARNTL2, ANTXR2, ANXA1, AKR1C3, and ARL4C compared to a control.

In some embodiments, the subject has been previously treated for melanoma with a prior treatment. In some embodiments, the prior treatment comprises a MAPK inhibitor. In some embodiments, the MAPK inhibitor comprises a B-Raf inhibitor. In some embodiments, the B-Raf inhibitor comprises vemurafenib. In some embodiments, the MAPK inhibitor is one described herein. In some embodiments, the prior treatment comprises an immunotherapy. In some embodiments, the immunotherapy is one described herein. In some embodiments, the prior treatment comprises an additional agent described herein. In some embodiments, the subject has been determined to be resistant to the prior treatment.

In some embodiments, the melanoma comprises dedifferentiated melanoma or amelanotic melanoma. In some embodiments, the patient has been diagnosed with melanoma. In some embodiments, the patient has been diagnosed with dedifferentiated melanoma or amelanotic melanoma.

In some embodiments, the method further comprises determining the level of one or more biomarkers in a biological sample from the subject, wherein the biomarker comprises MITF, SOX10, SOX9, SMAD3, CTNNB2, AXL, NGFR, EGFR. In some embodiments, the biomarker comprises one or more of AJUBA, TOR4A, MARCH4, ZDHHC2, ZNF467, ZNF185, ZIC2, VASN, UCP2, GALNT6, TNFAIP2, TNFSF18, TMEM40, TMEM200A, TMEM184A, TBL1X, TRERF1, TOX, TBC1D2, SFN, SAMD12, SAMD11, SOX9, SLC8A1, SLC38A4. SLC16A14, SCNSA, SCNN1A, SH3RF2, SERPINB7, SLPI, SECTM1, RUNX2, ARHGAP29, REN, PAWR, PSG9, PSG5, PSG4, PBX1, PLAGL1, PHLDB2, PLEKHA6, PDGFC, PLAU, PKP2, PLAC8, PADI3, PITX1, NUAK1, NTNG1, NMT2, MYEOV, MICAL2, MGST1, MECOM, LYPD6B, LAMA5, KISS1, KRT86, KRT81, KRT80, KRT8, KRT7, KRT18, JUP, IL7R, IL4R, IRS1, IGFN1, HES7, GDA, GLIS2, GATA2, GPRC5C, GPRC5A, FMNL1, FOXA1, FLNC, FERMT1, FAT4, FAM196B, ELFN2, EGFR, DSE, DMBT1, DIO2, DOCK2, CYP2S1, CRIM1, CDK15, CORO6, COLEC10, CCDC88C, CCDC69, F3, F2RL1, CLU, CDYL2, CITED2, CARD11, CPA4, CREB3L1, CNN1, CALB2, CDH4, BTBD11, BDNF, BASP1, BNC1, ATP8B1, ABCG2, ARMC4, ANKRD1, AR, AMIGO2, ADAMTSL1, and ACSL5. In some embodiments, the biomarker comprises one or more of VIT, VIPR1, VEGFC, TWIST2, TNFRSF12A, TPM1, TPBG, TLE4, TOX2, TLR4, THSD4, STX1A, SYT1, SYNPO, STRA6, STC2, SPRED3, SPOCD1, SPOCK1, SLC2A1, SLC16A2, SLC14A1, SLC12A8, SMAGP, SLIT2, SDK1, STAC, SLFN11, S100A2, ROBO4, RAB27B, PKIA, PRSS23, PAPPA, PRDM1, KCNMA1, KCNN4, PODXL, PDGFRB, PLAUR, PXDN, PTX3, NMNAT2, NRP1, NGEF, NEGR1, NRG1, NTN4, MT2A, MT1E, MPP4, LOXL2, LDOC1, LAMB3, JUN, IL31RA, IL11, IL1B, ITGA3, ITGA2, IGFBP6, ID1, INHBA, HRH1, GAS6, GLIPR1, GFRA1, GATA3, GPR176, FZD2, FJX1, FOSL1, FOXF1, FBLIM1, FLNB, FAM83G, FAM20C, FAM171A1, FAM155A, ERRFI1, EFNB2, DPYD, DKK1, DOCKS, CYR61, CLMP, COL13A1, COL12A1, COL5A1, F2RL2, C16orf45, C15orf52, C12orf75, CD163L1, CAV1, CARD10, CLCF1, CDH13, BMP2, AXL, ABCC3, ARNTL2, ANTXR2, ANXA1, AKR1C3, and ARL4C.

In some embodiments, the biological sample comprises cancerous cells. In some embodiments, the biological sample comprises cancerous skin cells. In some embodiments, the level of one or more of the biomarkers is differentially expressed compared to a control. In some embodiments, the control comprises a non-cancerous sample, a cancerous sample with a differentiated phenotype, a cancerous sample with a transitory phenotype, a cancerous sample with a melanocytic phenotype, or a MAPK inhibitor-sensitive cancerous sample, or an immunotherapy-resistant sample.

In some embodiments, the compositions of the disclosure excludes iron chelators and/or antioxidants.

In some embodiments, the method further comprises comparing the expression level of the biomarker to a control. In some embodiments, the method further comprises classifying the subject as having dedifferentiated melanoma or amelanotic melanoma when the expression level of the one or more biomarkers is differentially expressed compared to a control. In some embodiments, the method further comprises treating the subject classified as having dedifferentiated melanoma or amelanotic melanoma with a composition comprising a ferroptosis- or other cell death-inducing agent.

In some embodiments, detecting the expression level of the one or more biomarkers in the biological sample from the subject comprises determining the mRNA or protein expression of the one or more biomarkers. In some embodiments, determining the level of expression comprises performing fluorescence in situ hybridization (FISH), enzyme-linked immunosorbent assay (ELISA), comparative genomic hybridization (CGH), real time PCR, southern blot, western blot analysis, microarray analysis, or immunohistochemistry.

In some embodiments, the method further comprises treating the subject diagnosed with melanoma with a composition comprising a ferroptosis or other cell death-inducing agent.

In some embodiments, the administration comprises intratumoral, intravenous, peri-tumoral, oral, intra-lesional, or sub-cutaneous. In some embodiments, the mode of administration is a mode described herein.

Methods for determining expression levels, parsing patient populations, and determining cut-off values are known in the art and may include, for example, a Receiver Operating Characteristic (ROC) curve analysis.

In some embodiments of the above disclosed aspects, the method further comprises recording the expression level or the prognosis score in a tangible medium. In some embodiments, the method further comprises reporting the expression level or the prognosis score to the patient, a health care payer, a physician, an insurance agent, or an electronic system. In some embodiments, the method further comprises monitoring the patient for cancer recurrence or metastasis or prescribing a treatment that excludes the previously prescribed treatment. The treatment may be any treatment described herein.

Certain methods may involve the use of a normalized sample or control that is based on one or more cancer samples that are not from the patient being tested. Methods may also involve obtaining a biological sample comprising cancer cells from the patient or obtaining a cancer sample.

In some embodiments, the expression level is elevated or reduced relative to a control level of expression. In some embodiments, the control level is a mean, an average, a normalized value, or a cut-off value. One skilled in the art would understand that a patient would be predicted to respond to a ferroptosis or other cell death-inducing agent when the expression level of the measured biomarker(s) in the patient sample is the same, or not significantly different, or within 1 or 2 standard deviations from a control that represents a level in dedifferentiated melanoma or amelanotic melanoma.

In some embodiments, the expression or activity level of a protein is determined or has been from a biological sample from a patient or a control. In certain embodiments the sample is obtained from a biopsy from the tissue by any of the biopsy methods described herein or known in the art. In other embodiments the sample may be obtained from any of the tissues provided herein that include but are not limited to gall bladder, skin, heart, lung, pancreas, liver, muscle, kidney, smooth muscle, bladder, intestine, brain, prostate, esophagus, or thyroid tissue. Alternatively, the sample may include but not be limited to blood, serum, sweat, hair follicle, buccal tissue, tears, menses, urine, feces, or saliva. In particular embodiments, the sample may be a tissue sample, a whole blood sample, a urine sample, a saliva sample, a serum sample, a plasma sample, a skin sample or a fecal sample.

Some embodiments further involve isolating nucleic acids such as ribonucleic or RNA from a biological sample or in a sample of the patient. Other steps may or may not include amplifying a nucleic acid in a sample and/or hybridizing one or more probes to an amplified or non-amplified nucleic acid. The methods may further comprise assaying nucleic acids in a sample. Further embodiments include isolating or analyzing protein expression in a biological sample for the expression of polypeptides and biomarkers described herein.

In certain embodiments, a microarray may be used to measure or assay the level of protein expression in a sample. The methods may further comprise recording the expression or activity level in a tangible medium or reporting the expression or activity level to the patient, a health care payer, a physician, an insurance agent, or an electronic system.

In some embodiments, methods will involve determining or calculating a prognosis score based on data concerning the expression or activity level of one or more genes, meaning that the expression or activity level of a gene is at least one of the factors on which the score is based. A prognosis score will provide information about the patient, such as the general probability whether the patient is sensitive to a particular therapy or has poor survival or high chances of recurrence. In certain embodiments, a prognosis value is expressed as a numerical integer or number that represents a probability of 0% likelihood to 100% likelihood that a patient has a chance of poor survival or cancer recurrence or poor response to a particular treatment.

In some embodiments, the prognosis score is expressed as a number that represents a probability of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% likelihood (or any range derivable therein) that a patient has a chance of poor survival or cancer recurrence or poor or favorable response to a particular treatment. Alternatively, the probability may be expressed generally in percentiles, quartiles, or deciles.

A difference between or among weighted coefficients or expression or activity levels or between or among the weighted comparisons may be, be at least or be at most about 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 times or -fold (or any range derivable therein).

In some embodiments, determination of calculation of a diagnostic, prognostic, or risk score is performed by applying classification algorithms based on the expression values of biomarkers with differential expression p values of about, between about, or at most about 0.005, 0.006, 0.007, 0.008, 0.009, 0.01, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.03, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.1, 0.2, 0.3, 0.4, 0.5, 0.6, 0.7, 0.8, 0.9 or higher (or any range derivable therein). In certain embodiments, the prognosis score is calculated using one or more statistically significantly differentially expressed biomarkers (either individually or as difference pairs), including expression or activity levels in a gene or protein.

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: a) receiving information corresponding to an expression or activity level of a gene or protein in a sample from a patient; and b) determining a difference value in the expression or activity levels using the information corresponding to the expression or activity levels in the sample compared to a control or reference expression or activity level for the gene.

In other aspects, tangible computer-readable medium further comprise computer-readable code that, when executed by a computer, causes the computer to perform one or more additional operations comprising making recommendations comprising: wherein the patient in the step a) is under or after a first treatment for cancer, administering the same treatment as the first treatment to the patient if the patient does not have increased expression or activity level; administering a different treatment from the first treatment to the patient if the patient has increased expression or activity level.

In some embodiments, receiving information comprises receiving from a tangible data storage device information corresponding to the expression or activity levels from a tangible storage device. In additional embodiments the medium further comprises computer-readable code that, when executed by a computer, causes the computer to perform one or more additional operations comprising: sending information corresponding to the difference value to a tangible data storage device, calculating a prognosis score for the patient, treating the patient with a traditional therapy if the patient does not have expression or activity levels, and/or or treating the patient with an alternative therapy if the patient has increased expression or activity levels.

The tangible, computer-readable medium further comprise computer-readable code that, when executed by a computer, causes the computer to perform one or more additional operations comprising calculating a prognosis score for the patient. The operations may further comprise making recommendations comprising: administering a treatment comprising a ferroptosis or other cell death-inducing agent to a patient that is determined to have a particular phenotype or biomarkers expression level.

It is contemplated that any method or composition described herein can be implemented with respect to any other method or composition described herein and that different embodiments may be combined.

Use of the one or more compositions may be employed based on methods described herein. Use of one or more compositions may be employed in the preparation of medicaments for treatments according to the methods described herein. Other embodiments are discussed throughout this application. Any embodiment discussed with respect to one aspect of the disclosure applies to other aspects of the disclosure as well and vice versa. The embodiments in the Example section are understood to be embodiments that are applicable to all aspects of the technology described herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Immunoblot of pERK (Thr202/Tyr204) levels across a panel of melanoma cell lines showing no subtype-specific patterns. (B) Immunoblot of cells treated with vemurafenib at the indicated time-points showing initial suppression and rebound of pERK. (C) Crystal violet staining assays of long-term combination treatment of RSL3 (M229: 150 nM, M397: 40 nM, M249: 500 nM) and vemurafenib (V=1 µM) for 21 days. DMSO treated cells were stained after 7 days. (D, E) Quantification of crystal violet staining assays testing vemurafenib in combination with erastin (D) or RSL3 (E). (F, G) Immunoblot showing confirming activation of signaling pathways by TNFα (F) or IFNγ (G) treatment. (H) Crystal violet staining assays of RSL3 treatment for 7 days with cytokine exposure for the initial 3 days (M229 and M249) or 7 days (M397). IFNγ=100 U/mL, TNFα=1000 U/mL. (I-J) Quantification of crystal violet staining assays testing cytokine exposure in combination with erastin (I) or RSL3 (J), from at least three independent experiments. For (I), the left bar above Con, TNF, and IFNG represents DMSO, and the right bar above Con, TNF, and IFNG represents Erastin. For (J), the left bar above Con, TNF, and IFNG represents DMSO, and the right bar above Con, TNF, and IFNG represents RSL3. Relative amounts shown for quantified crystal violet assays are normalized to the average DMSO control treatment from at least three independent experiments. Statistical tests between groups to test for decrease in persistent cells were performed using a one-tailed paired t-test. Data shown represent mean±sd; t-test p values: *≤0.05, ≤0.01, *≤0.001. For A-J: Undifferentiated cell lines include M229R, M296, and M410; Neural Crest-like cell lines include M233, M238P, and M238R; Transitory cell lines include M397 and M229P; Melanocytic cell lines include M202, M249P, and M249R.

Figure 4:
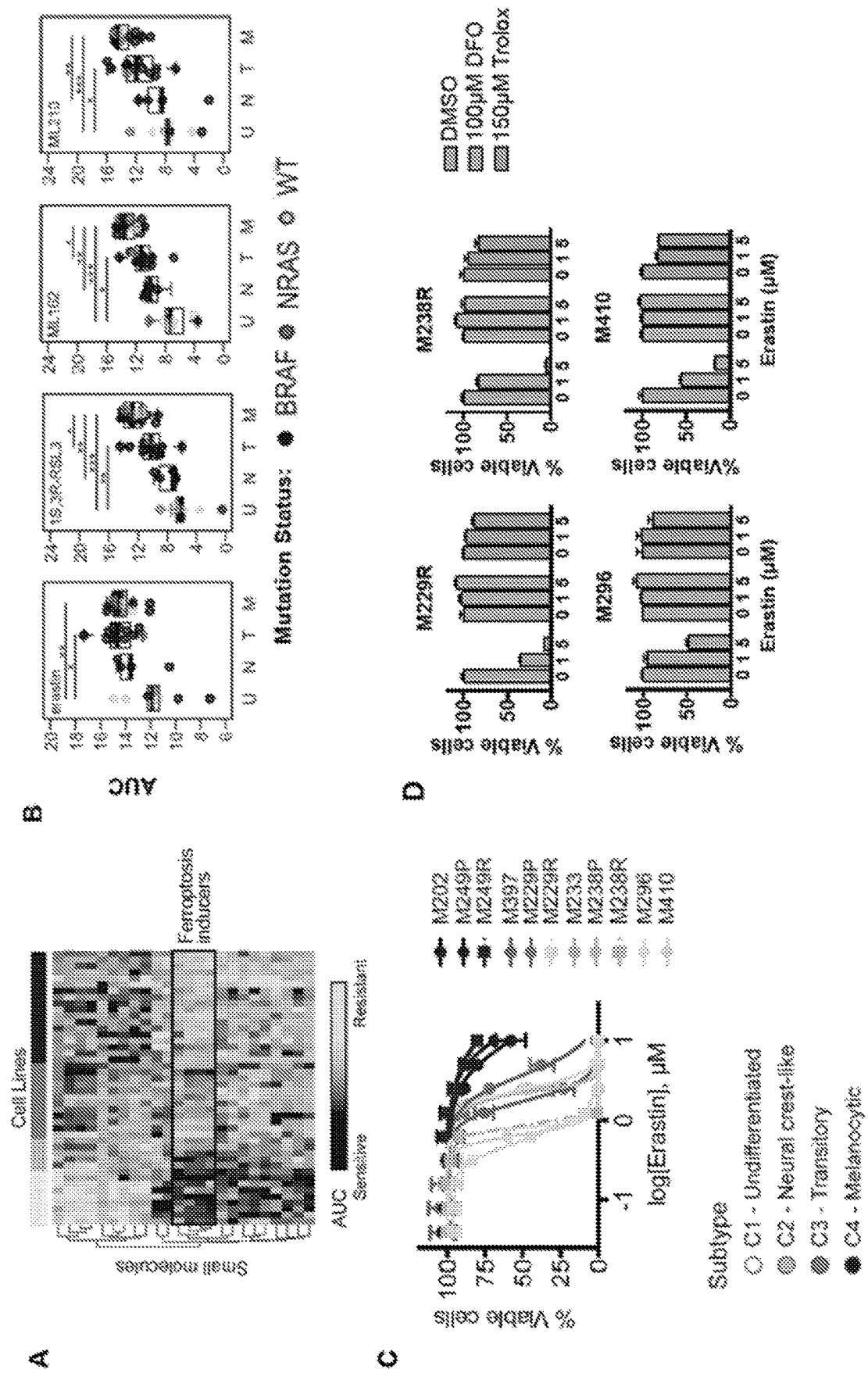
FIG. 4—Integration with pharmacogenomics drug sensitivity profiles reveals subtype-specific sensitivity to ferroptosis and other cell death-inducing drugs. (A) Hierarchical clustering of the CTRP pharmacogenomics database AUC values for small molecules pre-filtered for ANOVA P<0.01 across melanoma cell lines grouped by predicted subtype (B) Area under the curve (AUC) sensitivity values for the indicated ferroptosis inducing drugs grouped by predicted melanoma differentiation subtype. (U: Undifferentiated, N: Neural crest-like, T: Transitory, M: Melanocytic; Kruskal-Wallis ANOVA and Dunn's post hoc test p-values: *≤0.05, ≤0.01, *≤0.001, lower AUC values indicate increased sensitivity) (C) Validation of erastin sensitivity patterns across indicated M series melanoma cell lines. Paired parental and acquired resistant isogenic sublines are denoted by a square shape with resistant variant curves denoted with dashed lines. (D) Measurement of percent viable cells compared to DMSO control with erastin treatment alone or in combination with DFO or Trolox. Bars 1-3 of each graph represent DMSO, bars 4-6 of each graph represent 100 µM DFO, and bars 7-9 of each graph represent 150 µM Trolox.
Figure 14:
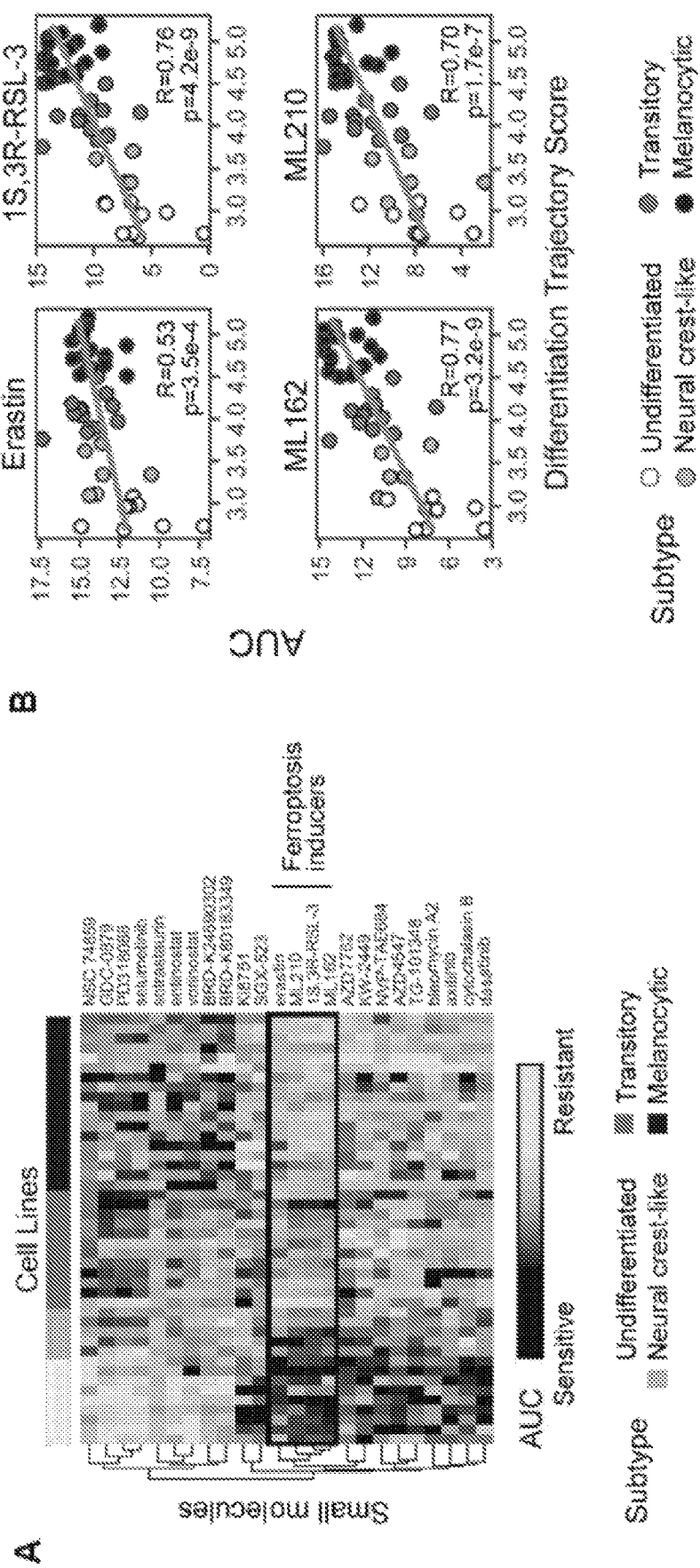
Figure 14:
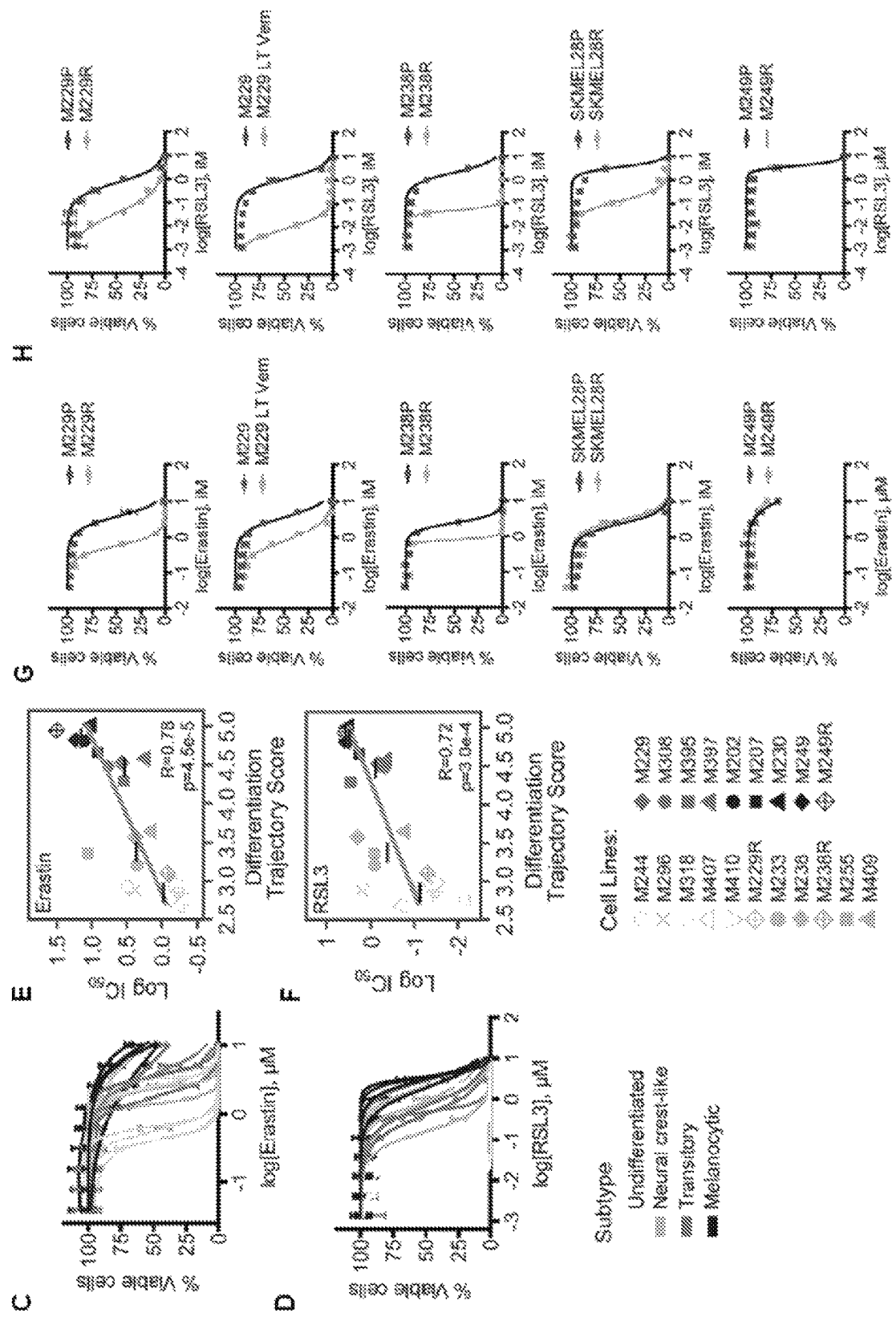

FIG. 14—Integration of pharmacogenomics drug sensitivity profiles reveals subtype-specific sensitivity to ferroptosis inducing drugs—supplement to FIG. 4 including testing of additional cells. (A) Hierarchical clustering of the CTRP pharmacogenomics database AUC values across differentiation subtypes. (B) Plot of AUC values vs. the differentiation trajectory score for all ferroptosis inducing drugs from the CTRP. Low AUC values indicate increased sensitivity. (C) Dose response curves across indicated M series melanoma cell lines for erastin and RSL3. (D) Corresponding plot of log IC50 concentration values for erastin and RSL3 treatment versus the differentiation trajectory score. Black dashes indicate mean within the subtype group. (E, F) Dose-response curves showing increased sensitivity to erastin (E) and RSL3 (F) in cell lines with vemurafenib-induced dedifferentiation including both acquired resistance lines (P: parental, R: resistant) or long-term (LT) adaptive resistance (44 days). Percent viable cells are calculated relative to DMSO. Drug response curves are shown as mean±sem of two replicates and representative of at least three independent experiments. For C-H: Undifferentiated cell lines include M229R, M296, and M410; Neural Crest-like cell lines include M233, M238P, and M238R; Transitory cell lines include M397 and M229P; Melanocytic cell lines include M202, M249P, and M249R.

DESCRIPTION OF ILLUSTRATIVE EMBODIMENTS

Ferroptosis occurs through an iron-dependent accumulation of lethal lipid reactive oxygen species (ROS) and regulated by GPX4, a glutathione-dependent enzyme that catalyzes the reduction of lipid ROS to lipid alcohols (Dixon et al., 2012; Yang et al., 2014). Ferroptosis is a relatively recent discovery of programmed cell death distinct from apoptosis and it was unexpectedly discovered that inducing ferroptosis in patients with certain melanoma phenotypes and/or genotypes can enhance signaling inhibition and immune therapies by synthetic lethal induction of ferroptosis.

I. Definitions

As used herein, the term "antibody" encompasses antibodies and antibody fragments thereof, derived from any antibody-producing mammal (e.g., mouse, rat, rabbit, and primate including human), that specifically bind to an antigenic polypeptide. Exemplary antibodies include polyclonal, monoclonal and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

The term substantially the same or not significantly different refers to a level of expression that is not significantly different than what it is compared to. Alternatively, or in conjunction, the term substantially the same refers to a level of expression that is less than 2, 1.5, or 1.25 fold different than the expression or activity level it is compared to.

A "subject," "individual" or "patient" is used interchangeably herein and refers to a vertebrate, for example a primate, a mammal or a human. Mammals include, but are not limited to equines, canines, bovines, ovines, murines, rats, simians, humans, farm animals, sport animals and pets. Also intended to be included as a subject are any subjects involved in clinical research trials not showing any clinical sign of disease, or subjects involved in epidemiological studies, or subjects used as controls.

The term "primer" or "probe" as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

As used herein, "increased expression," "increased level of expression," "elevated expression," "decreased expression," or "decreased level of expression" refers to an expression level of a biomarker in the subject's sample as compared to a reference level representing the same biomarker or a different biomarker. In certain aspects, the reference level may be a reference level of expression from a non-cancerous tissue from the same subject. Alternatively, the reference level may be a reference level of expression from a different subject or group of subjects. For example, the reference level of expression may be an expression level obtained from a sample (e.g., a tissue, fluid or cell sample) of a subject or group of subjects without cancer, or an expression level obtained from a non-cancerous tissue of a subject or group of subjects with cancer. The reference level may be a single value or may be a range of values. The reference level of expression can be determined using any method known to those of ordinary skill in the art. In some embodiments, the reference level is an average level of expression determined from a cohort of subjects with cancer or without cancer. The reference level may also be depicted graphically as an area on a graph. In certain embodiments, a reference level is a normalized level.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. In some embodiments it is contemplated that an numerical value discussed herein may be used with the term "about" or "approximately."

As used herein, the term "comprising" is intended to mean that the compositions and methods include the recited elements, but not excluding others. "Consisting essentially of" when used to define compositions and methods, shall mean excluding other elements of any essential significance to the combination for the stated purpose. "Consisting essentially of" in the context of pharmaceutical compositions of the disclosure is intended to include all the recited active agents and excludes any additional non-recited active agents, but does not exclude other components of the composition that are not active ingredients. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The terms "protein", "polypeptide" and "peptide" are used interchangeably herein when referring to a gene product or functional protein.

The terms "ameliorating," "inhibiting," or "reducing," or any variation of these terms, when used in the claims and/or the specification includes any measurable decrease or complete inhibition to achieve a desired result.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

The term "inhibitor" refers to a therapeutic agent that indirectly or directly inhibits the activity or expression of a protein, process (e.g. metabolic process), or biochemical pathway.

A person of ordinary skill in the art understands that an expression level from a test subject may be determined to have an elevated level of expression, a similar level of expression or a decreased level of expression compared to a reference level.

As used herein, "treating," "treatment" or "therapy" is an approach for obtaining beneficial or desired clinical results. This includes: reduce the alleviation of symptoms, the reduction of inflammation, the inhibition of cancer cell growth, and/or the reduction of tumor size. In some embodiments, the term treatment refers to the inhibition or reduction of cancer cell proliferation in a subject having cancer. Furthermore, these terms are intended to encompass curing as well as ameliorating at least one symptom of the condition or disease. For example, in the case of cancer, a response to treatment includes a reduction in cachexia, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, progression free survival, overall survival, each as measured by standards set by the National Cancer Institute and the U.S. Food and Drug Administration for the approval of new drugs. See Johnson et al. (2003) J. Clin. Oncol. 21(7):1404-1411.

The term "therapeutically effective amount" refers to an amount of the drug that treats or inhibits cancer in the subject. In some embodiments, the therapeutically effective amount inhibits at least or at most or exactly 100, 99, 98, 96, 94, 92, 90, 85, 80, 75, 70, 65, 60, 55, 50, 40, 30, 20, or 10%, or any derivable range therein, of a protein's activity or expression.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

II. Therapeutic Agents

A. Ferroptosis-Inducing Agents

Ferroptosis occurs through an iron-dependent accumulation of lethal lipid reactive oxygen species (ROS) and regulated by GPX4, a glutathione-dependent enzyme that catalyzes the reduction of lipid ROS to lipid alcohols (Dixon et al., 2012; Yang et al., 2014). Ferroptosis is a relatively recent discovery of programmed cell death distinct from apoptosis and the methods and compositions of the current application provides a differentiated-guided approach that can be harnessed to counter a melanoma therapy escape route.

Exemplary ferroptosis-inducing agents include glutathione synthesis inhibitors such as erastin, sulfalazine, buthioninesulfoximine (BSO), sorafenib, and DPI2; GPX4 inhibitors such as RSL3, RSL5, ML162, ML210, DPI7, DPI10, DPI12, DPI13, DPI17, DPI18, DPI19, CIL56, and FIN56; and other agents such as DPI3, DPI4, DPI6, CIL41, CIL69, CIL70, CIL75, and CIL79. Further examples include analogs of the disclosed ferroptosis-inducing agents such as erastin-A, erastin-B, or desmethyl-erastin, and sorafenib analogs, such as those described in WO 2015051149.

B. Immunotherapies

In some embodiments, the methods include the administration of an immunotherapy. Exemplary immunotherapies are described below.

1. Checkpoint Inhibitors

An "immune checkpoint inhibitor" is any molecule that directly or indirectly inhibits, partially or completely, an immune checkpoint pathway. Without wishing to be bound by any particular theory, it is generally thought that immune checkpoint pathways function to turn on or off aspects of the immune system, particularly T cells. Following activation of a T cell, a number of inhibitory receptors can be upregulated and present on the surface of the T cell in order to suppress the immune response at the appropriate time. In the case of persistent immune stimulation, such as with chronic viral infection, for example, immune checkpoint pathways can suppress the immune response and lead to immune exhaustion. Examples of immune checkpoint pathways include, without limitation, PD-1/PD-L1, CTLA4/B7-1, TIM-3, LAG3, By-He, H4, HAVCR2, ID01, CD276 and VTCN1. In the instance of the PD-1/PD-L1 immune checkpoint pathway, an inhibitor may bind to PD-1 or to PD-L1 and prevent interaction between the receptor and ligand. Therefore, the inhibitor may be an anti-PD-1 antibody or anti-PD-L1 antibody. Similarly, in the instance of the CTLA4/B7-1 immune checkpoint pathway, an inhibitor may bind to CTLA4 or to B7-1 and prevent interaction between the receptor and ligand. Further examples of immune checkpoint inhibitors can be found, for example, in WO2014/144885. Such immune checkpoint inhibitors are incorporated by reference herein. In some embodiments of any one of the methods, compositions or kits provided, the immune checkpoint inhibitor is a small molecule inhibitor of an immune checkpoint pathway. In some embodiments of any one of the methods, compositions or kits provided, the immune checkpoint inhibitor is a polypeptide that inhibits an immune checkpoint pathway. In some embodiments of any one of the methods, compositions or kits provided, the inhibitor is a fusion protein. In some embodiments of any one of the methods, compositions or kits provided, the immune checkpoint inhibitor is an antibody. In some embodiments of any one of the methods, compositions or kits provided, the antibody is a monoclonal antibody.

Non-limiting examples of immune checkpoint inhibitors include fully human monoclonal antibodies, such as RG7446, BMS-936558/MDX-1106, BMS-936559 (anti-PDL1 antibody), Yervoy/ipilimumab (anti-CTLA-4 checkpoint inhibitor), and Tremelimumab (CTLA-4 blocking antibody); humanized antibodies, such as pidilizumab (CT-011, CureTech Ltd.) and lambrolizumab (MK-3475, Merck, PD-1 blocker); and fusion proteins, such as AMP-224 (Merck). Other examples of checkpoint inhibitors include anti-OX40, PD-L1 monoclonal Antibody (Anti-B7-H1; MEDI4736), Nivolumab (BMS-936558, Bristol-Myers Squibb, anti-PD1 antibody), CT-011 (anti-PD1 antibody), BY55 monoclonal antibody, MPLDL3280A (anti-PDL1 antibody), and MSB0010718C (anti-PDL1 antibody), MDX-1105 (Medarex), MPDL3280A (Genentech), Anti-KIR antibodies such as lirlumab (Innate Pharma) and IPH2101 (Innate Pharma) may perform similar functions in NK cells. Further examples of checkpoint inhibitors include agonistic anti-4-1bb antibody; agonistic anti-CD27 antibody; agonistic anti-GM antibody; agonistic anti-OX40 antibody; and antagonistic anti-TIM3 antibody.

2. Additional Immunotherapies and Agents

In some embodiments, the method further comprises administration of an immunotherapy or an additional agent described herein. In some embodiments, the additional agent is an immunostimulator. The term "immunostimulator" as used herein refers to a compound that can stimulate an immune response in a subject, and may include an adjuvant. In some embodiments, an immunostimulator is an agent that does not constitute a specific antigen, but can boost the strength and longevity of an immune response to an antigen. Such immunostimulators may include, but are not limited to stimulators of pattern recognition receptors, such as Toll-like receptors, RIG-1 and NOD-like receptors (NLR), mineral salts, such as alum, alum combined with monphosphoryl lipid (MPL) A of Enterobacteria, such as *Escherichia coli, Salmonella minnesota, Salmonella typhimurium,* or *Shigella flexneri* or specifically with MPL® (AS04), MPL A of above-mentioned bacteria separately, saponins, such as QS-21, Quil-A, ISCOMs, ISCOMATRIX, emulsions such as MF59, Montanide, ISA 51 and ISA 720, AS02 (QS21+squalene+MPL.), liposomes and liposomal formulations such as AS01, synthesized or specifically prepared microparticles and microcarriers such as bacteria-derived outer membrane vesicles (OMV) of *N. gonorrheae, Chlamydia trachomatis* and others, or chitosan particles, depot-forming agents, such as Pluronic block co-polymers, specifically modified or prepared peptides, such as muramyl dipeptide, aminoalkyl glucosaminide 4-phosphates, such as RC529, or proteins, such as bacterial toxoids or toxin fragments.

In some embodiments, the additional agent comprises an agonist for pattern recognition receptors (PRR), including, but not limited to Toll-Like Receptors (TLRs), specifically TLRs 2, 3, 4, 5, 7, 8, 9 and/or combinations thereof. In some embodiments, additional agents comprise agonists for Toll-Like Receptors 3, agonists for Toll-Like Receptors 7 and 8, or agonists for Toll-Like Receptor 9; preferably the recited immunostimulators comprise imidazoquinolines; such as R848; adenine derivatives, such as those disclosed in U.S. Pat. No. 6,329,381, U.S. Published Patent Application 2010/0075995, or WO 2010/018132; immunostimulatory DNA; or immunostimulatory RNA. In some embodiments, the additional agents also may comprise immunostimulatory RNA molecules, such as but not limited to dsRNA, poly I:C or poly I:poly C12U (available as Ampligen®, both poly I:C and poly I:polyC 12U being known as TLR3 stimulants), and/or those disclosed in F. Heil et al., "Species-Specific Recognition of Single-Stranded RNA via Toll-like Receptor 7 and 8" Science 303(5663), 1526-1529 (2004); J. Vollmer et al., "Immune modulation by chemically modified ribonucleosides and oligoribonucleotides" WO 2008033432 A2; A. Forsbach et al., "Immunostimulatory oligoribonucleotides containing specific sequence motif(s) and targeting the Toll-like receptor 8 pathway" WO 2007062107 A2; E. Uhlmann et al., "Modified oligoribonucleotide analogs with enhanced immunostimulatory activity" U.S. Pat. Appl. Publ. US 2006241076; G. Lipford et al., "Immunostimulatory viral RNA oligonucleotides and use for treating cancer and infections" WO 2005097993 A2; G. Lipford et al., "Immunostimulatory G,U-containing oligoribonucleotides, compositions, and screening methods" WO 2003086280 A2. In some embodiments, an additional agent may be a TLR-4 agonist, such as bacterial lipopolysaccharide (LPS), VSV-G, and/or HMGB-1. In some embodiments, additional agents may comprise TLR-5 agonists, such as flagellin, or portions or derivatives thereof, including but not limited to those disclosed in U.S. Pat. Nos. 6,130,082, 6,585,980, and 7,192,725.

In some embodiments, additional agents may be proinflammatory stimuli released from necrotic cells (e.g., urate crystals). In some embodiments, additional agents may be activated components of the complement cascade (e.g., CD21, CD35, etc.). In some embodiments, additional agents may be activated components of immune complexes. Additional agents also include complement receptor agonists, such as a molecule that binds to CD21 or CD35. In some embodiments, the complement receptor agonist induces endogenous complement opsonization of the synthetic nanocarrier. In some embodiments, immunostimulators are cytokines, which are small proteins or biological factors (in the range of 5 kD-20 kD) that are released by cells and have specific effects on cell-cell interaction, communication and behavior of other cells. In some embodiments, the cytokine receptor agonist is a small molecule, antibody, fusion protein, or aptamer.

In some embodiments, the additional agent is a chimeric antigen receptor (CAR). CARs are artificial T cell receptors which graft a specificity onto an immune effector cell. The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g. neuroblastoma cells). The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows the scFv to orient in different directions to enable antigen binding. The transmembrane domain is a typical hydrophobic alpha helix usually derived from the original molecule of the signalling endodomain which protrudes into the cell and transmits the desired signal.

Additional agents that can act as immunostimulators include STING agonists. The STING pathway is a pathway that is involved in the detection of cytosolic DNA. Stimulator of interferon genes (STING), also known as transmembrane protein 173 (TMEM173) and MPYS/MITA/ERIS, is a protein that in humans is encoded by the TMEM173 gene. STING plays an important role in innate immunity. STING induces type I interferon production when cells are infected with intracellular pathogens, such as viruses, mycobacteria and intracellular parasites. Type I interferon, mediated by STING, protects infected cells and nearby cells from local infection in an autocrine and paracrine manner.

STING is encoded by the TMEM173 gene. It works as both a direct cytosolic DNA sensor (CDS) and an adaptor protein in Type I interferon signaling through different molecular mechanisms. It has been shown to activate downstream transcription factors STAT6 and IRF3 through TBK1, which are responsible for antiviral response and innate immune response against intracellular pathogen.

STING resides in the endoplasmic reticulum, but in the presence of cytosolic DNA, the sensor cGAS binds to the DNA and forms cyclic dinucleotides. This di-nucleotide binds to STING and promotes its aggregation and translocation from the ER through the Golgi to perinuclear sites. There, STING complexes with TBK1 and promotes its phosphorylation. Once TBK1 is phosphorylated, it phosphorylates the transcription factor IRF3 that dimerices and traslocates to the nucleus, where it activates the transcription of type I IFN and other innate immune genes.

STING agonsists can include 3'3'-cGAMP fluorinated, fluorinated cyclic diadenylate monophosphate, ZDHHC1, 2'3'-c-di-AM(PS)2 (Rp,Rp), 2'2'-cGAMP, c-di-IMP, 2'3'-cGAM(PS)2 (Rp/Sp), 3'3'-cGAMP, DMXAA, 2'3'-cGAMP, c-di-GMP, c-di-GMP, 2'3'-c-di-GMP, 2'3'-c-di-AMP, c-di-GMP Fluorinated, and c-di-AMP.

In some embodiments, the immunotherapy includes cytolytic viral therapy, such administration of an oncolytic virus or modified version thereof. Oncolytic viruses include oncolytic herpes simplex virus, adenovirus, reovirus, measles, Newcastle disease virus, and vaccinia virus.

3. Vaccine Immunotherapies

The methods of the disclosure may also include the administration of vaccines. As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject, including administrations.

In certain aspects of the present disclosure, the compositions may be administered either in vitro, ex vivo, or in vivo. In certain in vitro embodiments, autologous T cells are incubated with compositions of this disclosure. The cells can then be used for in vitro analysis, or alternatively for ex vivo administration.

Method aspects of the disclosure include vaccinating a subject with a variety of different immunotherapeutic compositions. In some embodiments, the methods further comprise administration of immune cells to the subject. In some embodiments, the immune cells are autologous. In some embodiments, the immune cells has been contacted with an antigen. In some embodiments, the antigen is an antigen expressed by the subject's cancer cells. In some embodiments, the antigen is cell free. The term "cell free" refers to a composition that does not have any cellular components. In some embodiments, the antigen is an extract from the patient's tumor. In some embodiments, the antigen is a polypeptide. In some embodiments, the antigen comprises one or more of tumor cell lysate, apoptotic tumor cell, tumor-associated antigen, and tumor-derived mRNA. In some embodiments, the immune cell has been contacted with a maturation agent. In some embodiments, the maturation agent is one or more of GM-CSF, IL-1β, TNF-α, and PGE2. In some embodiments, the immune cell comprises a chimeric antigen receptor.

In some embodiments, the immune cell is an antigen presenting cells. Antigen-presenting cells can be used as a cancer vaccine. Examples of the antigen-presenting cells include dendritic cells, macrophages, B cells, and tumor cells (false antigen-presenting cells) in which a T cell stimulation factor (e.g., B7 or 4-1 BBL) and the like is forcibly expressed by, for example, gene transfer. In some embodiments, the antigen presenting cell is a dendritic cell.

The route of administration of the immune cell may be, for example, intratumoral, intracutaneous, subcutaneous, intravenous, intralymphatic, and intraperitoneal administrations. In some embodiments, the administration is intratumoral or intrapymphatic. In some embodiments, the immune cells are administered directly into a cancer tissue or a lymph node.

In some embodiments, the immune cell is a T cell. T cells can also be used as a cancer vaccine. The T cells may be ones that have been contacted with an antigen or with antigen-presenting cells. For example, APCs may be cultured with tumor antigen specific to the patient's cancer to differentiate them, into, for example, CD8-positive cytotoxic T lymphocytes (CTLs) or CD4-positive helper T cells. The T cells thus established may be administered to an individual with cancer.

The origin of the naive T cells is not specifically limited and it may be derived from, for example, peripheral blood of a vertebrate animal. The naive T cell used may be CD8-positive cells or CD4-positive cells isolated from a PBMC fraction. In some embodiments, the naive T cells are CD8- positive cells or CD4-positive cells mixed with other cells and components without being isolated from the PBMC fraction in terms of the efficiency of inducing CTLs. For example, when cells of a PBMC fraction are cultured in a medium supplemented with serum and tumor antigen, the PBMCs differentiate into dendritic cell precursors. The dendritic cell precursors then bind to the peptide and differentiate into dendritic cells as the antigen-presenting cells presenting this peptide/tumor antigen. The antigen-presenting cells stimulate the CD8-positive T cells in the PBMCs to differentiate them into CTLs. Thus, the CTLs capable of recognizing the added peptide can be obtained. The CTLs thus obtained may be isolated and used as the cancer vaccine as they are. Alternatively, they may be cultured further in the presence of interleukin such as IL-2, the antigen-presenting cell, and tumor antigen before used as the cancer vaccine. The route of their administration is not specifically limited and examples include intracutaneous, subcutaneous, intravenous, and intratumoral administrations.

In further embodiments, the immunotherapy comprises ex vivo administration of dendritic cells, such as dendritic cells that have been contacted with antigens, such as autologous or allogeneic tumor lysate pulsed DCs, DC/tumor cell fusion productions, mRNA transduced DCs and virus-transduced DCs.

4. Tumor Cell Vaccines

Melanoma tumor cells may also be used as immunogens using a range of vaccination regimes. Tumor cell vaccines can be designed either as whole melanoma cells from fresh or cryopreserved tumor samples irradiated prior to treatment to halt propagation in the recipient or derived from subcellular components of melanoma cell lysates. Vaccines can either be derived from autologous or allogeneic tumor cells.

Tumor cell vaccines may be combined with other non-specific adjuvants such as *Bacillus* Calmette-Guérin (BCG) or proinflammatory cytokines, such as GM-CSF. In other embodiments, autologous tumor cells may be conjugated to haptens such as 2, 4-dinitrophenol (DNP; e.g., M-Vax). Allogeneic tumor cell vaccines can be prepared from multiple cell lines and are not derived from the recipient's own cells. This allows for manipulation of tumor cells to express a range of tumor-associated antigens that may induce a wide range of immune responses. Allogeneic tumor cell vaccines are also easier to prepare, standardize and produce, and may have wider clinical applicability. Exemplary allogenic tumor cell vaccines useful as an immunotherapy according to the methods of the disclosure include Canvaxin™ (CancerVax Corp, CA, USA) and Melacine® (Corixa-Montana, MT, USA), which may be used alone or with other agents, such as adjuvants, for example.

In some embodiments, the vaccine comprises a peptide vaccine. Numerous melanoma antigens have been identified, and a variety of vaccination strategies have been examined aimed at activating immune responses to recognize and destroy melanoma cells expressing these antigens using vaccines that can direct immune responses against a single HLA-restricted antigen (univalent) or polyvalent vaccines, using multiple antigens or antigenic epitopes. Polyvalent vaccines may increase the probability of eradicating tumors by: circumventing antigenic heterogeneity and loss of antigen expression by cancer cells in progressing tumors; and overcoming HLA restriction.

For antigenic vaccine approaches to therapy, selection of immunodominant MHC-presented epitopes of known tumor-associated antigens is aimed at generating CTL responses against tumor cells expressing these antigens. Antigenic peptides are generally derived from one or more melanoma-associated antigens, such as tyrosinase, tyrosinase-related proteins (TRP-1 and TRP-2), melanoma-associated glycoprotein antigen family (gp100/pmel17) and MART/Melan-A, and also cancer-testis antigens such as NY-ESO-1, melanoma antigen E (MAGE) and B melanoma antigen. Various approaches have aimed to enhance the immunogenic capacity of peptide vaccines by administering these in combination with cytokines (e.g., IL-2, IFN-α2b and GM-CSF), Toll-like receptor (TLR) agonists (e.g., CpG oligodeoxynucleotides and imiquimod) or emulsified with adjuvants (e.g., incomplete Freud's adjuvant, ASO2B and Alum).

In some embodiments, the vaccine is a DNA or a viral vaccine. Nucleic acid vaccines, either as naked plasmid DNA or as recombinant attenuated viruses or viral vectors (e.g., retroviruses, adenoviruses, poxviruses and alphaviruses), encode one or more specific epitopes of one or more tumor-associated antigens (e.g., tyrosinase and gp100) that can be recognized by cytotoxic CD8+ T cells. Vaccination administered by intramuscular or intradermal injections should trigger nucleic acid uptake by somatic cells such as keratinocytes or myocytes or by APCs such as DCs with subsequent antigen expression at the site of inoculation. APCs, either directly inoculated or through release of antigen by somatic cells (cross-priming) can then become activated to present antigens to T cells either in situ or upon migration to lymph nodes leading to T-cell maturation and expansion.

5. Cytokines

Exemplary cytokine treatments include decarbazine, INF-α2β, IL-2, high-dose IL-2, pegylated IFN-α2β, IFN-α, IFN-γ, GM-CSF and IL-2, IL-4, IL-6, IL-12, IL-18 and IL-21.

C. MAPK Inhibitors

In some embodiments, the compositions comprise a MAPK inhibitor. MAPK inhibitors include those that inhibit MAPK/ERK pathway. Exemplary MAPK inhibitors include vemurafenib, dabrafenib, trametinib, cobimetinib, selumetinib, and combinations thereof. Specific combinations include 1) dabrafenib and cobimetinib and 2) vemurafenib and trametinib. In some embodiments, the MAPK inhibitor is a MEK inhibitor. MEK inhibitors include cobimetinib, CI-1040, PD035901, Binimetinib (MEK162), selumetinib, and Trametinib (GSK1120212). In some embodiments, the MAPK inhibitor is a Raf inhibitor. Raf inhibitors include, for example, SB590885, PLX4720, XL281, RAF265, encorafenib, dabrafenib, vemurafenib. In some embodiments, the Raf inhibitor is an inhibitor of B-Raf. Exemplary B-Raf inhibitors include sorafenib, PLX4032, regorafenib (BAY 73-4506), NVP-BHG712, vemurafenib, and dabarefenib.

Further examples include VX-702 (Vertex), Pamapimod (Roche Pharmaceuticals), Iosmapimod (GW856553; GlaxoSmithKline), Dilmapimod (SB 681323; GlaxoSmithKline), Doramapimod (BIRB 796; Boehringer Ingelheim Pharmaceutical), BMS-582949 (Bristol-Myers Squibb), ARRY-797 (Array BioPharma), PH797804 (Pfizer), PF-3644022 (Pfizer), MSC2032964A (Merck Serono), CI-1040 (PD184352; Pfizer), PD0325901 (Pfizer), Selumetinib (AZD6244; Array BioPharma/AstraZeneca), Trametinib (GSK1120212; GlaxoSmithKline), ARRY-438162 (Array BioPharma), ralimetinib, SB203580, and SCIO-469 (Scios).

D. Additional Agents

In some embodiments, the methods and compositions of the disclosure comprises the administration of an additional agent or includes an additional agent in a therapeutic composition. In some embodiments, the additional agent is a VEGF-targeted agent. Targeting the tumor vascular microenvironment and preventing growth of metastases by inhibiting new blood vessel formation and supply of vital nutrients may help restrict tumor growth and progression. Melanoma metastases have a prominent vascular component and tumor-induced sentinel lymph-node lymphangiogenesis promotes melanoma metastasis to distant sites, lending merits to anti-angiogenic therapies. In some embodiments, the additional agent is a neutralizing or inhibitor antibody directed to VEGF-A, VEGFR, and/or VEGFR-2. One exemplary additional agent that is a VEGF-targeting agent is the bevacizumab (Avastin®, Genentech/Roche; San Francisco, CA, USA). The antibody recognizes an epitope expressed on all VEGF-A isoforms with high affinity and blocks VEGF interaction with both receptors.

In some embodiments, the additional agent comprises an antibody that targets Tregs. Tregs are thought to suppress antitumor responses in vivo and may, in part, be responsible for the limited efficacy of strategies aimed at boosting immunity, such as IL-2 and tumor vaccines. An exemplary agent in this category is a CD25 antibody. In some embodiments, the CD25 antibody comprises daclizumab.

In some embodiments, the additional agent is an agent that targets costimulatory molecules. Other strategies entail activating T cells with agonist mAbs such as those against costimulatory cell surface molecules OX40 and CD137. OX40, expressed on antigen-primed T cells, recognizes its cognate ligand on APCs (DCs, activated B cells and macrophages) mediating the survival and activation of T cells. CD137, also known as 4-1BB, a membrane glycoprotein belonging to the tumor necrosis factor receptor family is expressed on primed T cells and other immune cells (e.g., NKs, monocytes, macrophages, neutrophils, mast cells and DCs). CD137 recognizes a ligand on the surface of APCs and this interaction is thought to induce T-cell proliferation and maturation. Agonistic antibodies to CD137 have been shown to induce antitumoral immune responses associated with increased T-cell activation and infiltration in tumor lesions.

In some embodiments, the additional agent is an anti-CD40 antibody. CD40 is expressed on solid tumors including melanoma. CD40 represents a potential therapeutic target in that activation of CD40 promotes apoptosis within tumor cells. It is also responsible in part for the generation of tumor-specific T-cell responses, as CD40L is expressed on the surface of activated T lymphocytes. CD40-CD40L interaction on T lymphocytes mediates increased immune stimulation and cytotoxicity. CD40 stimulation is also thought to allow for DC maturation, a process which is inhibited within the tumor microenvironment and is thought to be contributory to immune escape.

In some embodiments, the additional agent comprises an agent that targets integran or fibronectin isoforms. In some embodiments, the agent targets integrins of the αv family that are involved in tumor-associated angiogenesis. Exemplary agents include antibodies such as the chimeric volociximab (M200) against α5β1 integrin, the humanized mAb etaracizumab (Abegrin™ [MedImmune Inc., MD, USA], Vitaxin or MEDI-522) recognising the integrin αvβ3, and the human antibody CNTO 95 against αv integrin.

In some embodiments, the agent targets a splice variant of fibronectin, such as the isoform extra domain-B (ED-B) fibronectin, a protein found in the subendothelial extracellular matrix in tumor lesions that is produced by melanoma cells and thought to promote tumor growth and angiogenesis. In some embodiments, the agent is an antibody that recognizes the ED-B fibronectin. In a specific embodiment, the agent is an antibody recognizing ED-B fibronectin fused with the human pluripotent cytokine IL-12 (e.g. AS1409—Antisoma; London, UK).

In some embodiments, the additional agent comprises a bisphosphonate. In some embodiments, the biphoshpnate is used in combination with IL-2. An exemplary biphosphate comprises zoledronate.

In some embodiments, the additional agent comprises a chemotherapeutic agent. Chemotherapies include, for example, cisplatin (CDDP), carboplatin, dacarbazine, temozolomide, nab-paclitaxel, paclitaxel, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant of the foregoing.

In some embodiments, the chemotherapeutic agent is selected from dacarbazine, temozolomide, nab-paclitaxel, paclitaxel, cisplatin, carboplatin, and vinblastine.

Suitable therapeutic agents include, for example, *vinca* alkaloids, agents that disrupt microtubule formation (such as colchicines and its derivatives), anti-angiogenic agents, therapeutic antibodies, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

E. Inhibitory Antibodies

In certain embodiments, an antibody or a fragment thereof that binds to at least a portion of a B-Raf or MEK protein and inhibits the protein's activity and/or function is used in the methods and compositions described herein.

In some embodiments, the antibody is a monoclonal antibody or a polyclonal antibody. In some embodiments, the antibody is a chimeric antibody, an affinity matured antibody, a humanized antibody, or a human antibody. In some embodiments, the antibody is an antibody fragment. In some embodiments, the antibody is a Fab, Fab', Fab'-SH, F(ab')2, or scFv. In one embodiment, the antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a mouse. In one embodiment, an antigen binding sequence is synthetic, e.g., obtained by mutagenesis (e.g., phage display screening, etc.). In one embodiment, a chimeric antibody has murine V regions and human C region. In one embodiment, the murine light chain V region is fused to a human kappa light chain or a human IgG1 C region.

Examples of antibody fragments include, without limitation: (i) the Fab fragment, consisting of VL, VH, CL and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker which allows the two domains to associate to form a binding domain; (viii) bi-specific single chain Fv dimers (see U.S. Pat. No. 5,091,513) and (ix) diabodies, multivalent or multispecific fragments constructed by gene fusion (U.S. Patent Pub. 2005/0214860). Fv, scFv or diabody molecules may be stabilized by the incorporation of disulphide bridges linking the VH and VL domains. Minibodies comprising a scFv joined to a CH3 domain may also be made (Hu et al, 1996).

A monoclonal antibody is a single species of antibody wherein every antibody molecule recognizes the same epitope because all antibody producing cells are derived from a single B-lymphocyte cell line. Hybridoma technology involves the fusion of a single B lymphocyte from a mouse previously immunized with an antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced. However, in therapeutic applications a goal of hybridoma technology is to reduce the immune reaction in humans that may result from administration of monoclonal antibodies generated by the non-human (e.g., mouse) hybridoma cell line.

Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent and human amino acid sequences. In "humanized" monoclonal antibodies, only the hypervariable CDR is derived from mouse monoclonal antibodies, and the framework regions are derived from human amino acid sequences. It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

It is possible to create engineered antibodies, using monoclonal and other antibodies and recombinant DNA technology to produce other antibodies or chimeric molecules which retain the antigen or epitope specificity of the original antibody, i.e., the molecule has a binding domain. Such techniques may involve introducing DNA encoding the immunoglobulin variable region or the CDRs of an antibody to the genetic material for the framework regions, constant regions, or constant regions plus framework regions, of a different antibody. See, for instance, U.S. Pat. Nos. 5,091,513, and 6,881,557, which are incorporated herein by this reference.

By known means as described herein, polyclonal or monoclonal antibodies, binding fragments and binding domains and CDRs (including engineered forms of any of the foregoing), may be created that are specific to a protein described herein, one or more of its respective epitopes, or conjugates of any of the foregoing, whether such antigens or epitopes are isolated from natural sources or are synthetic derivatives or variants of the natural compounds.

Antibodies may be produced from any animal source, including birds and mammals. Particularly, the antibodies may be ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by this reference. These techniques are further described in: Marks (1992); Stemmer (1994); Gram et al. (1992); Barbas et al. (1994); and Schier et al. (1996).

Methods for producing polyclonal antibodies in various animal species, as well as for producing monoclonal antibodies of various types, including humanized, chimeric, and fully human, are well known in the art. Methods for producing these antibodies are also well known. For example, the following U.S. patents and patent publications provide enabling descriptions of such methods and are herein incorporated by reference: U.S. Patent publication Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent publications, and other publications cited herein and therein are hereby incorporated by reference in the present application.

It is fully expected that antibodies to B-Raf or MEK will have the ability to neutralize or counteract the effects of the protein regardless of the animal species, monoclonal cell line or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into binding fragments having the binding domain or CDR. Removal of the Fc portion reduces the likelihood that the antigen binding fragment will elicit an undesirable immunological response and, thus, antibodies without Fc may be particularly useful for prophylactic or therapeutic treatments. As described above, antibodies may also be constructed so as to be chimeric, partially or fully human, so as to reduce or eliminate the adverse immunological consequences resulting from administering to an animal an antibody that has been produced in, or has sequences from, other species.

In some embodiments, the inhibitor is a peptide, polypeptide, or protein inhibitor. In some embodiments, the inhibitor is an antagonistic antibody.

F. Nucleic Acid Inhibitors

Inhibitory nucleic acids or any ways of inhibiting gene expression of BRAF and MEK known in the art are contemplated in certain embodiments. Examples of an inhibitory nucleic acid include but are not limited to siRNA (small interfering RNA), short hairpin RNA (shRNA), double-stranded RNA, an antisense oligonucleotide, a ribozyme, and a nucleic acid encoding thereof. An inhibitory nucleic acid may inhibit the transcription of a gene or prevent the translation of a gene transcript in a cell. An inhibitory nucleic acid may be from 16 to 1000 nucleotides long, and in certain embodiments from 18 to 100 nucleotides long. The nucleic acid may have nucleotides of at least or at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 50, 60, 70, 80, 90 or any range derivable therefrom.

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

In some embodiments, the nucleic acid inhibitor is comprises a modification, such as a chemical modification or a modified base. In some embodiments, one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 (or any derivable range therein) of the nucleotide positions in one or both strands of an siRNA molecule are modified. Modifications include nucleic acid sugar modifications, base modifications, backbone (internucleotide linkage) modifications, non-nucleotide modifications, and/or any combination thereof. In certain instances, purine and pyrimidine nucleotides are differentially modified. For example, purine and pyrimidine nucleotides can be differentially modified at the 2'-sugar position (i.e., at least one purine has a different modification from at least one pyrimidine in the same or different strand at the 2'-sugar position). In other instances, at least one modified nucleotide is a 2'-deoxy-2'-fluoro nucleotide, a 2'-deoxy nucleotide, or a 2'-O-alkyl nucleotide. In certain embodiments, the siRNA molecule has 3' overhangs of one, two, three, or four nucleotide(s) on one or both of the strands. In other embodiments, the siRNA lacks overhangs (i.e., has blunt ends). The overhangs can be modified or unmodified. Examples of modified nucleotides in the overhangs include, but are not limited to, 2'-O-alkyl nucleotides, 2'-deoxy-2'-fluoro nucleotides, or 2'-deoxy nucleotides. The overhang nucleotides in the antisense strand can comprise nucleotides that are complementary to nucleotides in the Bach1 target sequence. Likewise, the overhangs in the sense stand can comprise nucleotides that are in the Bach1 target sequence. In certain instances, the siRNA molecules have two 3' overhang nucleotides on the antisense stand that are 2'-O-alkyl nucleotides and two 3' overhang nucleotides on the sense stand that are 2'-deoxy nucleotides.

Particularly, an inhibitory nucleic acid may be capable of decreasing the expression of a protein or mRNA by at least 10%, 20%, 30%, or 40%, more particularly by at least 50%, 60%, or 70%, and most particularly by at least 75%, 80%, 90%, 95% or more or any range or value in between the foregoing.

In further embodiments, there are synthetic nucleic acids that are MAPK inhibitors. An inhibitor may be between 17 to 25 nucleotides in length and comprises a 5' to 3' sequence that is at least 90% complementary to the 5' to 3' sequence of a mature BACH1 mRNA. In certain embodiments, an inhibitor molecule is 17, 18, 19, 20, 21, 22, 23, 24, or 25 nucleotides in length, or any range derivable therein. Moreover, an inhibitor molecule has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature MAPK gene (e.g. BRAF or MEK) mRNA, particularly a mature, naturally occurring mRNA. One of skill in the art could use a portion of the probe sequence that is complementary to the sequence of a mature mRNA as the sequence for an mRNA inhibitor. Moreover, that portion of the probe sequence can be altered so that it is still 90% complementary to the sequence of a mature mRNA.

G. Combination Therapies

The methods and compositions may include chemotherapy, therapeutic agents, surgical removal of cancerous cells, radiation therapy, and combinations thereof. In some aspects, the treatment regimen excludes one or more of chemotherapy, therapeutic agents, surgical removal of cancerous cells and/or radiation therapy.

In some embodiments, the treatment regimen comprises a combination of the one or more chemotherapeutic agents, therapeutic agents, inhibitors, and/or immunotherapies described herein. In some embodiments, the treatment regimen excludes one or more of the chemotherapeutic agents, therapeutic agents, inhibitors, and/or immunotherapies described herein.

In further embodiments a combination of therapeutic treatment agents is administered to cancer cells. The therapeutic agents may be administered serially (within minutes, hours, or days of each other) or in parallel; they also may be administered to the patient in a pre-mixed single composition.

Various combinations of more than an anticancer modality, agent or compound (or a combination of such agents and/or compounds) may be employed, for example, a first anticancer modality, agent or compound is "A" and a second anticancer modality, agent or compound (or a combination of such modalities, agents and/or compounds) given as part of an anticancer therapy regime, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the therapeutic compounds or agents to a patient will follow general protocols for the administration of such compounds, taking into account the toxicity, if any, of the therapy. It is expected that the treatment cycles would be repeated as necessary. It also is contemplated that various standard therapies, as well as surgical intervention, may be applied in combination with the described therapy.

Radiation therapy that cause DNA damage and have been used extensively include what are commonly known as y-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Alternative cancer therapy include any cancer therapy other than surgery, chemotherapy and radiation therapy, such as immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

III. Methods of Treatment

A. Treatment of Cancer

Certain embodiments are directed to methods of treating cancer, such as skin cancer, based on certain parameters such as biomarker levels and cancer phenotypes. Any known treatments that are contemplated for treating a cancer or skin cancer can be used.

In certain aspects, there may be provided methods for treating a subject determined to have cancer and with a predetermined expression profile of one or more biomarkers disclosed herein.

In a further aspect, biomarkers and related systems that can establish a prognosis of cancer patients can be used to identify patients who may get benefit of conventional single or combined modality therapy. In the same way, those patients who do not get much benefit from such conventional single or combined modality therapy can be identified and can be offered alternative treatment(s).

Approximately 60% of persons with cancer will undergo surgery of some type, which includes preventative, diagnostic or staging, curative and palliative surgery. Curative surgery is a cancer treatment that may be used in conjunction with other therapies, such as the treatment, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the treatment methods described herein may be used in conjunction with removal of superficial cancers, precancers, or incidental amounts of normal tissue.

In some embodiments, the methods may further comprise a therapy described herein such as those described below.

Laser therapy is the use of high-intensity light to destroy tumor cells. Laser therapy affects the cells only in the treated area. Laser therapy may be used to destroy cancerous tissue and relieve a blockage in the esophagus when the cancer cannot be removed by surgery. The relief of a blockage can help to reduce symptoms, especially swallowing problems.

Photodynamic therapy (PDT), a type of laser therapy, involves the use of drugs that are absorbed by cancer cells; when exposed to a special light, the drugs become active and destroy the cancer cells. PDT may be used to relieve symptoms of esophageal cancer such as difficulty swallowing.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein). A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

The cancers amenable for treatment include skin cancers of various types, locations, sizes, and characteristics. In some embodiments, the skin cancer is de-differentiated melanoma or amelanotic melanoma.

B. ROC Analysis

In statistics, a receiver operating characteristic (ROC), or ROC curve, is a graphical plot that illustrates the performance of a binary classifier system as its discrimination threshold is varied. The curve is created by plotting the true positive rate against the false positive rate at various threshold settings. (The true-positive rate is also known as sensitivity in biomedical informatics, or recall in machine learning. The false-positive rate is also known as the fall-out and can be calculated as 1−specificity). The ROC curve is thus the sensitivity as a function of fall-out. In general, if the probability distributions for both detection and false alarm are known, the ROC curve can be generated by plotting the cumulative distribution function (area under the probability distribution from −infinity to +infinity) of the detection probability in the y-axis versus the cumulative distribution function of the false-alarm probability in x-axis.

ROC analysis provides tools to select possibly optimal models and to discard suboptimal ones independently from (and prior to specifying) the cost context or the class distribution. ROC analysis is related in a direct and natural way to cost/benefit analysis of diagnostic decision making.

The ROC curve was first developed by electrical engineers and radar engineers during World War II for detecting enemy objects in battlefields and was soon introduced to psychology to account for perceptual detection of stimuli. ROC analysis since then has been used in medicine, radiology, biometrics, and other areas for many decades and is increasingly used in machine learning and data mining research.

The ROC is also known as a relative operating characteristic curve, because it is a comparison of two operating characteristics (TPR and FPR) as the criterion changes. ROC analysis curves are known in the art and described in Metz CE (1978) Basic principles of ROC analysis. Seminars in Nuclear Medicine 8:283-298; Youden W J (1950) An index for rating diagnostic tests. Cancer 3:32-35; Zweig M H, Campbell G (1993) Receiver-operating characteristic (ROC) plots: a fundamental evaluation tool in clinical medicine. Clinical Chemistry 39:561-577; and Greiner M, Pfeiffer D, Smith R D (2000) Principles and practical application of the receiver-operating characteristic analysis for diagnostic tests. Preventive Veterinary Medicine 45:23-41, which are herein incorporated by reference in their entirety.

ROC analysis is useful for determining cut-off values for expression levels, protein levels, or activity levels. Such cut-off values can be used to determine a patient's prognosis and to predict a patient's response to a particular therapy.

C. Biological Sample Preparation

In certain aspects, methods involve obtaining a sample from a subject. The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from skin tissue by any of the biopsy methods previously mentioned. In other embodiments the sample may be obtained from any of the tissues provided herein that include but are not limited to non-cancerous or cancerous tissue and non-cancerous or cancerous tissue from the serum, gall bladder, mucosal, skin, heart, lung, breast, pancreas, blood, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects the sample is obtained from melanocytes or skin cells derived from a tumor or neoplasm. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, scraping, phlebotomy, or any other methods known in the art. In some cases, the sample may be obtained, stored, or transported using components of a kit of the present methods. In some cases, multiple samples, such as multiple cancerous samples may be obtained for diagnosis by the methods described herein. In other cases, multiple samples, such as one or more samples from one tissue type (for example breast) and one or more samples from another tissue may be obtained for diagnosis by the methods. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, dermatologist, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a colorectal or a suspected colorectal tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, proteins, polypeptides, genes, gene fragments, expression products, gene expression products, protein expression products or fragments, or gene expression product fragments of an individual to be tested. Methods for determining sample suitability and/or adequacy are provided.

In some embodiments, the subject may be referred to a specialist such as an oncologist, surgeon, or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

IV. Analysis of Gene Expression

A gene shall be understood to be specifically expressed in a certain cell type if the expression level of said gene in said cell type is at least 2-fold, 5-fold, 10-fold, 100-fold, 1000-fold, or 10000-fold higher than in a reference cell type, or in a mixture of reference cell types. Reference cell types include non-cancerous tissue cells or a heterogeneous population of cancers.

Comparison of multiple marker genes with a threshold level can be performed as follows: 1. The individual marker genes are compared to their respective threshold levels. 2. The number of marker genes, the expression level of which is above their respective threshold level, is determined. 3. If a marker genes is expressed above its respective threshold level, then the expression level of the marker gene is taken to be "above the threshold level".

In certain aspects, the determination of expression levels is on a gene chip, such as an Affymetrix™ gene chip. In another aspect, the determination of expression levels is done by kinetic real time PCR.

In certain aspects, the methods can relate to a system for performing such methods, the system comprising (a) apparatus or device for storing data on the biomarker level of the patient; (b) apparatus or device for determining the expression level of at least one marker gene or activity; (c) apparatus or device for comparing the expression level of the first marker gene or activity with a predetermined first threshold value; (d) apparatus or device for determining the expression level of at least one second, third, fourth, $5^{th}$, $6^{th}$ or more marker gene or activity and for comparing with a corresponding predetermined threshold; and (e) computing apparatus or device programmed to provide a unfavorable or poor prognosis or favorable prognosis based on the comparisons.

The person skilled in the art readily appreciates that an unfavorable or poor prognosis can be given if the expression level of the first marker gene with the predetermined first threshold value indicates a tumor that is likely to recur or not respond well to standard therapies.

The expression patterns can also be compared by using one or more ratios between the expression levels of different cancer biomarkers. Other suitable measures or indicators can also be employed for assessing the relationship or difference between different expression patterns.

The expression levels of cancer biomarkers can be compared to reference expression levels using various methods. These reference levels can be determined using expression levels of a reference based on all cancer patients. Alternatively, it can be based on an internal reference such as a gene that is expressed in all cells. In some embodiments, the reference is a gene expressed in cancer cells at a higher level than any biomarker. Any comparison can be performed using the fold change or the absolute difference between the expression levels to be compared. One or more cancer biomarkers can be used in the comparison. It is contemplated that 1, 2, 3, 4, 5, 6, 7, 8, 9, 10, and/or 11 biomarkers (or any range derivable therein) may be compared to each other and/or to a reference that is internal or external. A person of ordinary skill in the art would know how to do such comparisons.

Comparisons or results from comparisons may reveal or be expressed as x-fold increase or decrease in expression relative to a standard or relative to another biomarker or relative to the same biomarker but in a different class of prognosis. In some embodiments, patients with a poor prognosis have a relatively high level of expression (overexpression) or relatively low level of expression (underexpression) when compared to patients with a better or favorable prognosis, or vice versa.

Fold increases or decreases may be, be at least, or be at most 1-, 2-, 3-, 4-, 5-, 6-, 7-, 8-, 9-, 10-, 11-, 12-, 13-, 14-, 15-, 16-, 17-, 18-, 19-, 20-, 25-, 30-, 35-, 40-, 45-, 50-, 55-, 60-, 65-, 70-, 75-, 80-, 85-, 90-, 95-, 100- or more, or any range derivable therein. Alternatively, differences in expression may be expressed as a percent decrease or increase, such as at least or at most 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000% difference, or any range derivable therein.

Other ways to express relative expression levels are with normalized or relative numbers such as 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or any range derivable therein. In some embodiments, the levels can be relative to a control.

Algorithms, such as the weighted voting programs, can be used to facilitate the evaluation of biomarker levels. In addition, other clinical evidence can be combined with the biomarker-based test to reduce the risk of false evaluations. Other cytogenetic evaluations may be considered in some embodiments.

Any biological sample from the patient that contains cancer cells may be used to evaluate the expression pattern of any biomarker discussed herein. In some embodiments, a biological sample from a tumor is used. Evaluation of the sample may involve, though it need not involve, panning (enriching) for cancer cells or isolating the cancer cells.

A. Measurement of Gene Expression Using Nucleic Acids

Testing methods based on differentially expressed gene products are well known in the art. In accordance with one aspect, the differential expression patterns of cancer biomarkers can be determined by measuring the levels of RNA transcripts of these genes, or genes whose expression is modulated by the these genes, in the patient's cancer cells. Suitable methods for this purpose include, but are not limited to, RT-PCR, Northern Blot, in situ hybridization, Southern Blot, slot-blotting, nuclease protection assay and oligonucleotide arrays.

In certain aspects, RNA isolated from cancer cells can be amplified to cDNA or cRNA before detection and/or quantitation. The isolated RNA can be either total RNA or mRNA. The RNA amplification can be specific or non-specific. Suitable amplification methods include, but are not limited to, reverse transcriptase PCR, isothermal amplification, ligase chain reaction, and Qbeta replicase. The amplified nucleic acid products can be detected and/or quantitated through hybridization to labeled probes. In some embodiments, detection may involve fluorescence resonance energy transfer (FRET) or some other kind of quantum dots.

Amplification primers or hybridization probes for a cancer biomarker can be prepared from the gene sequence or obtained through commercial sources, such as Affymatrix. In certain embodiments the gene sequence is identical or complementary to at least 8 contiguous nucleotides of the coding sequence.

Sequences suitable for making probes/primers for the detection of their corresponding cancer biomarkers include those that are identical or complementary to all or part of the cancer biomarker genes described herein. These sequences are all nucleic acid sequences of cancer biomarkers.

The use of a probe or primer of between 13 and 100 nucleotides, particularly between 17 and 100 nucleotides in length, or in some aspects up to 1-2 kilobases or more in length, allows the formation of a duplex molecule that is both stable and selective. Molecules having complementary sequences over contiguous stretches greater than 20 bases in length may be used to increase stability and/or selectivity of the hybrid molecules obtained. One may design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

In one embodiment, each probe/primer comprises at least 15 nucleotides. For instance, each probe can comprise at least or at most 20, 25, 50, 75, 100, 125, 150, 175, 200, 225, 250, 275, 300, 325, 350, 400 or more nucleotides (or any range derivable therein). They may have these lengths and have a sequence that is identical or complementary to a gene described herein. Particularly, each probe/primer has relatively high sequence complexity and does not have any ambiguous residue (undetermined "n" residues). The probes/primers can hybridize to the target gene, including its RNA transcripts, under stringent or highly stringent conditions. In some embodiments, because each of the biomarkers has more than one human sequence, it is contemplated that probes and primers may be designed for use with each of these sequences. For example, inosine is a nucleotide frequently used in probes or primers to hybridize to more than one sequence. It is contemplated that probes or primers may have inosine or other design implementations that accommodate recognition of more than one human sequence for a particular biomarker.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In another embodiment, the probes/primers for a gene are selected from regions which significantly diverge from the sequences of other genes. Such regions can be determined by checking the probe/primer sequences against a human genome sequence database, such as the Entrez database at the NCBI. One algorithm suitable for this purpose is the BLAST algorithm. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence to increase the cumulative alignment score. Cumulative scores are calculated using, for nucleotide sequences, the parameters M (reward score for a pair of matching residues; always >0) and N (penalty score for mismatching residues; always <0). The BLAST algorithm parameters W, T, and X determine the sensitivity and speed of the alignment. These parameters can be adjusted for different purposes, as appreciated by one of ordinary skill in the art.

In one embodiment, quantitative RT-PCR (such as TaqMan, ABI) is used for detecting and comparing the levels of RNA transcripts in cancer samples. Quantitative RT-PCR involves reverse transcription (RT) of RNA to cDNA followed by relative quantitative PCR (RT-PCR). The concentration of the target DNA in the linear portion of the PCR process is proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is true in the linear range portion of the PCR reaction. The final concentration of the target DNA in the plateau portion of the curve is determined by the availability of reagents in the reaction mix and is independent of the original concentration of target DNA. Therefore, the sampling and quantifying of the amplified PCR products may be carried out when the PCR reactions are in the linear portion of their curves. In addition, relative concentrations of the amplifiable cDNAs may be normalized to some independent standard, which may be based on either internally existing RNA species or externally introduced RNA species. The abundance of a particular mRNA species may also be determined relative to the average abundance of all mRNA species in the sample.

In one embodiment, the PCR amplification utilizes one or more internal PCR standards. The internal standard may be an abundant housekeeping gene in the cell or it can specifically be GAPDH, GUSB and β-2 microglobulin. These standards may be used to normalize expression levels so that the expression levels of different gene products can be compared directly. A person of ordinary skill in the art would know how to use an internal standard to normalize expression levels.

A problem inherent in clinical samples is that they are of variable quantity and/or quality. This problem can be overcome if the RT-PCR is performed as a relative quantitative RT-PCR with an internal standard in which the internal standard is an amplifiable cDNA fragment that is similar or larger than the target cDNA fragment and in which the abundance of the mRNA encoding the internal standard is roughly 5-100 fold higher than the mRNA encoding the target. This assay measures relative abundance, not absolute abundance of the respective mRNA species.

In another embodiment, the relative quantitative RT-PCR uses an external standard protocol. Under this protocol, the PCR products are sampled in the linear portion of their amplification curves. The number of PCR cycles that are optimal for sampling can be empirically determined for each target cDNA fragment. In addition, the reverse transcriptase products of each RNA population isolated from the various samples can be normalized for equal concentrations of amplifiable cDNAs.

Nucleic acid arrays can also be used to detect and compare the differential expression patterns of cancer biomarkers in cancer cells. The probes suitable for detecting the corresponding cancer biomarkers can be stably attached to known discrete regions on a solid substrate. As used herein, a probe is "stably attached" to a discrete region if the probe maintains its position relative to the discrete region during the hybridization and the subsequent washes. Construction of nucleic acid arrays is well known in the art. Suitable substrates for making polynucleotide arrays include, but are not limited to, membranes, films, plastics and quartz wafers.

A nucleic acid array can comprise at least 1, 2, 3, 4, 5, 6, 7, 8, 9, 10, 15, 20, 25, 30, 35, 40, 45, 50, 60, 70, 80, 90, 100, 150, 200, 250 or more different polynucleotide probes, which may hybridize to different and/or the same biomarkers. Multiple probes for the same gene can be used on a single nucleic acid array. Probes for other disease genes can also be included in the nucleic acid array. The probe density on the array can be in any range. In some embodiments, the density may be 50, 100, 200, 300, 400, 500 or more probes/cm$^2$.

Specifically contemplated are chip-based nucleic acid technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of one or more cancer biomarkers with respect to diagnostic, prognostic, and treatment methods.

Certain embodiments may involve the use of arrays or data generated from an array. Data may be readily available. Moreover, an array may be prepared in order to generate data that may then be used in correlation studies.

An array generally refers to ordered macroarrays or microarrays of nucleic acid molecules (probes) that are fully or nearly complementary or identical to a plurality of mRNA molecules or cDNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon. Such arrays may vary in a number of different ways, including average probe length, sequence or types of probes, nature of bond between the probe and the array surface, e.g. covalent or non-covalent, and the like. The labeling and screening methods and the arrays are not limited in its utility with respect to any parameter except that the probes detect expression levels; consequently, methods and compositions may be used with a variety of different types of genes.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per cm2. The surface area of the array can be about or less than about 1, 1.6, 2, 3, 4, 5, 6, 7, 8, 9, or 10 cm2.

Moreover, a person of ordinary skill in the art could readily analyze data generated using an array. Such protocols include information found in WO 9743450; WO 03023058; WO 03022421; WO 03029485; WO 03067217; WO 03066906; WO 03076928; WO 03093810; WO 03100448A1, all of which are specifically incorporated by reference.

In one embodiment, nuclease protection assays are used to quantify RNAs derived from the cancer samples. There are many different versions of nuclease protection assays known to those practiced in the art. The common characteristic that these nuclease protection assays have is that they involve hybridization of an antisense nucleic acid with the RNA to be quantified. The resulting hybrid double-stranded molecule is then digested with a nuclease that digests single-stranded nucleic acids more efficiently than double-stranded molecules. The amount of antisense nucleic acid that survives digestion is a measure of the amount of the target RNA species to be quantified. An example of a nuclease protection assay that is commercially available is the RNase protection assay manufactured by Ambion, Inc. (Austin, Tex.).

B. Measurement of Gene Expression Using Proteins and Polypeptides

In other embodiments, the differential expression patterns of cancer biomarkers can be determined by measuring the levels of polypeptides encoded by these genes in cancer cells. Methods suitable for this purpose include, but are not limited to, immunoassays such as ELISA, RIA, FACS, dot blot, Western Blot, immunohistochemistry, and antibody-based radioimaging. Protocols for carrying out these immunoassays are well known in the art. Other methods such as 2-dimensional SDS-polyacrylamide gel electrophoresis can also be used. These procedures may be used to recognize any of the polypeptides encoded by the cancer biomarker genes described herein.

One example of a method suitable for detecting the levels of target proteins in peripheral blood samples is ELISA. In an exemplifying ELISA, antibodies capable of binding to the target proteins encoded by one or more cancer biomarker genes are immobilized onto a selected surface exhibiting protein affinity, such as wells in a polystyrene or polyvinylchloride microtiter plate. Then, cancer cell samples to be tested are added to the wells. After binding and washing to remove non-specifically bound immunocomplexes, the bound antigen(s) can be detected. Detection can be achieved by the addition of a second antibody which is specific for the target proteins and is linked to a detectable label. Detection may also be achieved by the addition of a second antibody, followed by the addition of a third antibody that has binding affinity for the second antibody, with the third antibody being linked to a detectable label. Before being added to the microtiter plate, cells in the peripheral blood samples can be lysed using various methods known in the art. Proper extraction procedures can be used to separate the target proteins from potentially interfering substances.

In another ELISA embodiment, the cancer cell samples containing the target proteins are immobilized onto the well surface and then contacted with the antibodies. After binding and washing to remove non-specifically bound immunocomplexes, the bound antigen is detected. Where the initial antibodies are linked to a detectable label, the immunocomplexes can be detected directly. The immunocomplexes can also be detected using a second antibody that has binding affinity for the first antibody, with the second antibody being linked to a detectable label.

Another typical ELISA involves the use of antibody competition in the detection. In this ELISA, the target proteins are immobilized on the well surface. The labeled antibodies are added to the well, allowed to bind to the target proteins, and detected by means of their labels. The amount of the target proteins in an unknown sample is then determined by mixing the sample with the labeled antibodies before or during incubation with coated wells. The presence of the target proteins in the unknown sample acts to reduce the amount of antibody available for binding to the well and thus reduces the ultimate signal.

Different ELISA formats can have certain features in common, such as coating, incubating or binding, washing to remove non-specifically bound species, and detecting the bound immunocomplexes. For instance, in coating a plate with either antigen or antibody, the wells of the plate can be incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test samples. Examples of these nonspecific proteins include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means can also be used. After binding of a protein or antibody to the well, coating with a non-reactive material to reduce background, and washing to remove unbound material, the immobilizing surface is contacted with the control and/or clinical or biological sample to be tested under conditions effective to allow immunocomplex (antigen/antibody) formation. These conditions may include, for example, diluting the antigens and antibodies with solutions such as BSA, bovine gamma globulin (BGG) and phosphate buffered saline (PBS)/Tween and incubating the antibodies and antigens at room temperature for about 1 to 4 hours or at 49° C. overnight. Detection of the immunocomplex then requires a labeled secondary binding ligand or antibody, or a secondary binding ligand or antibody in conjunction with a labeled tertiary antibody or third binding ligand.

After all of the incubation steps in an ELISA, the contacted surface can be washed so as to remove non-complexed material. For instance, the surface may be washed with a solution such as PBS/Tween, or borate buffer. Following the formation of specific immunocomplexes between the test sample and the originally bound material, and subsequent washing, the occurrence of the amount of immunocomplexes can be determined.

To provide a detecting means, the second or third antibody can have an associated label to allow detection. In one embodiment, the label is an enzyme that generates color development upon incubating with an appropriate chromogenic substrate. Thus, for example, one may contact and incubate the first or second immunocomplex with a urease, glucose oxidase, alkaline phosphatase or hydrogen peroxidase-conjugated antibody for a period of time and under conditions that favor the development of further immunocomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl)-benzhiazoline-6-sulfonic acid (ABTS) and hydrogen peroxide, in the case of peroxidase as the enzyme label. Quantitation can be achieved by measuring the degree of color generation, e.g., using a spectrophotometer.

Another suitable method is RIA (radioimmunoassay). An example of RIA is based on the competition between radiolabeled-polypeptides and unlabeled polypeptides for binding to a limited quantity of antibodies. Suitable radiolabels include, but are not limited to, $I^{125}$. In one embodiment, a fixed concentration of $I^{125}$-labeled polypeptide is incubated with a series of dilution of an antibody specific to the polypeptide. When the unlabeled polypeptide is added to the system, the amount of the $I^{125}$-polypeptide that binds to the antibody is decreased. A standard curve can therefore be constructed to represent the amount of antibody-bound $I^{125}$-polypeptide as a function of the concentration of the unlabeled polypeptide. From this standard curve, the concentration of the polypeptide in unknown samples can be determined. Various protocols for conducting RIA to measure the levels of polypeptides in cancer cell samples are well known in the art.

Suitable antibodies include, but are not limited to, polyclonal antibodies, monoclonal antibodies, chimeric antibodies, humanized antibodies, single chain antibodies, Fab fragments, and fragments produced by a Fab expression library.

Antibodies can be labeled with one or more detectable moieties to allow for detection of antibody-antigen complexes. The detectable moieties can include compositions detectable by spectroscopic, enzymatic, photochemical, biochemical, bioelectronic, immunochemical, electrical, optical or chemical means. The detectable moieties include, but are not limited to, radioisotopes, chemiluminescent compounds, labeled binding proteins, heavy metal atoms, spectroscopic markers such as fluorescent markers and dyes, magnetic labels, linked enzymes, mass spectrometry tags, spin labels, electron transfer donors and acceptors, and the like.

Protein array technology is discussed in detail in Pandey and Mann (2000) and MacBeath and Schreiber (2000), each of which is herein specifically incorporated by reference. These arrays typically contain thousands of different proteins or antibodies spotted onto glass slides or immobilized in tiny wells and allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds. In certain embodiments such technology can be used to quantitate a number of proteins in a sample, such as a cancer biomarker proteins.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

The earliest and best-known protein chip is the ProteinChip by Ciphergen Biosystems Inc. (Fremont, Calif.). The ProteinChip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF).

The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

In other aspects, the levels of polypeptides in samples can be determined by detecting the biological activities associated with the polypeptides. If a biological function/activity of a polypeptide is known, suitable in vitro bioassays can be designed to evaluate the biological function/activity, thereby determining the amount of the polypeptide in the sample.

V. Pharmaceutical Compositions

In certain aspects, the compositions or agents for use in the methods, such as therapeutic agents or inhibitors, are suitably contained in a pharmaceutically acceptable carrier. The carrier is non-toxic, biocompatible and is selected so as not to detrimentally affect the biological activity of the agent. The agents in some aspects of the disclosure may be formulated into preparations for local delivery (i.e. to a specific location of the body, such as skeletal muscle or other tissue) or systemic delivery, in solid, semi-solid, gel, liquid or gaseous forms such as tablets, capsules, powders, granules, ointments, solutions, depositories, inhalants and injections allowing for oral, parenteral or surgical administration. Certain aspects of the disclosure also contemplate local administration of the compositions by coating medical devices, local administration, and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting examples, microparticles, microspheres, nanospheres or nanoparticles composed of proteins, liposomes, carbohydrates, synthetic organic compounds, inorganic compounds, polymeric or copolymeric hydrogels and polymeric micelles.

In certain aspects, the actual dosage amount of a composition administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active agent, such as an isolated exosome, a related lipid nanovesicle, or an exosome or nanovesicle loaded with therapeutic agents or diagnostic agents. In other embodiments, the active agent may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 microgram/kg/body weight to about 100 mg/kg/body weight, about 5 microgram/kg/body weight to about 500 milligram/kg/body weight, etc., can be administered.

Solutions of pharmaceutical compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

In certain aspects, the pharmaceutical compositions are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg or less, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antgifungal agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In further aspects, the pharmaceutical compositions may include classic pharmaceutical preparations. Administration of pharmaceutical compositions according to certain aspects may be via any common route so long as the target tissue is available via that route. This may include oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, intralesional, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the pharmaceutical composition is determined based on the intended goal. The term "unit dose" or "dosage" refers to physically discrete units suitable for use in a subject, each unit containing a predetermined-quantity of the pharmaceutical composition calculated to produce the desired responses discussed above in association with its administration, i.e., the appropriate route and treatment regimen. The quantity to be administered, both according to number of treatments and unit dose, depends on the protection or effect desired.

Precise amounts of the pharmaceutical composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

VI. Kits

Certain aspects of the present disclosure also concern kits containing compositions of the disclosure or compositions to implement methods of the disclosure. In some embodiments, kits can be used to evaluate one or more nucleic acid and/or polypeptide molecules. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more nucleic acid probes, synthetic RNA molecules or inhibitors, or any value or range and combination derivable therein. In some embodiments, there are kits for evaluating gene expression, protein expression, or protein activity in a cell.

In certain embodiments, the kits may comprise materials for analyzing cell morphology and/or phenotype, such as histology slides and reagents, histological stains, alcohol, buffers, tissue embedding mediums, paraffin, formaldehyde, and tissue dehydrant.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using probes, polypeptide detecting agents, and/or inhibitors or agents of the disclosure for prognostic or diagnostic applications are included. Specifically contemplated are any such molecules corresponding to any nucleic acid or polypeptide identified herein.

In certain aspects, negative and/or positive control agents are included in some kit embodiments. The control molecules can be used to verify transfection efficiency and/or control for transfection-induced changes in cells.

Embodiments of the disclosure include kits for analysis of a pathological sample by assessing a nucleic acid or polypeptide profile for a sample comprising, in suitable container means, two or more RNA probes, or a polypeptide detecting agent, wherein the RNA probes or polypeptide detecting agent detects nucleic acids or polypeptides described herein. Furthermore, the probes, detecting agents and/or inhibiting reagents may be labeled. Labels are known in the art and also described herein. In some embodiments, the kit can further comprise reagents for labeling probes, nucleic acids, and/or detecting agents. The kit may also include labeling reagents, including at least one of amine-modified nucleotide, poly(A) polymerase, and poly(A) polymerase buffer. Labeling reagents can include an amine-reactive dye. Certain aspects also encompass kits for performing the diagnostic or therapeutic methods. Such kits can be prepared from readily available materials and reagents. For example, such kits can comprise any one or more of the following materials: enzymes, reaction tubes, buffers, detergent, primers, probes, antibodies. In a particular embodiment, these kits allow a practitioner to obtain samples of neoplastic cells in breast, blood, tears, semen, saliva, urine, tissue, serum, stool, sputum, cerebrospinal fluid and supernatant from cell lysate. In another particular embodiment, these kits include the needed apparatus for performing RNA extraction, RT-PCR, and gel electrophoresis. Instructions for performing the assays can also be included in the kits.

In a particular aspect, these kits may comprise a plurality of agents for assessing the differential expression of a plurality of biomarkers, wherein the kit is housed in a container. The kits may further comprise instructions for using the kit for assessing expression, means for converting the expression data into expression values and/or means for analyzing the expression values to generate prognosis. The agents in the kit for measuring biomarker expression may comprise a plurality of PCR probes and/or primers for qRT-PCR and/or a plurality of antibody or fragments thereof for assessing expression of the biomarkers. In another embodiment, the agents in the kit for measuring biomarker expression may comprise an array of polynucleotides complementary to the mRNAs of the biomarkers. Possible means for converting the expression data into expression values and for analyzing the expression values to generate scores that predict survival or prognosis may be also included.

Kits may comprise a container with a label. Suitable containers include, for example, bottles, vials, and test tubes. The containers may be formed from a variety of materials such as glass or plastic. The container may hold a composition which includes a probe that is useful for prognostic or non-prognostic applications, such as described above. The label on the container may indicate that the composition is used for a specific prognostic or non-prognostic application, and may also indicate directions for either in vivo or in vitro use, such as those described above. The kit may comprise the container described above and one or more other containers comprising materials desirable from a commercial and user standpoint, including buffers, diluents, filters, needles, syringes, and package inserts with instructions for use.

VII. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Figure 1:
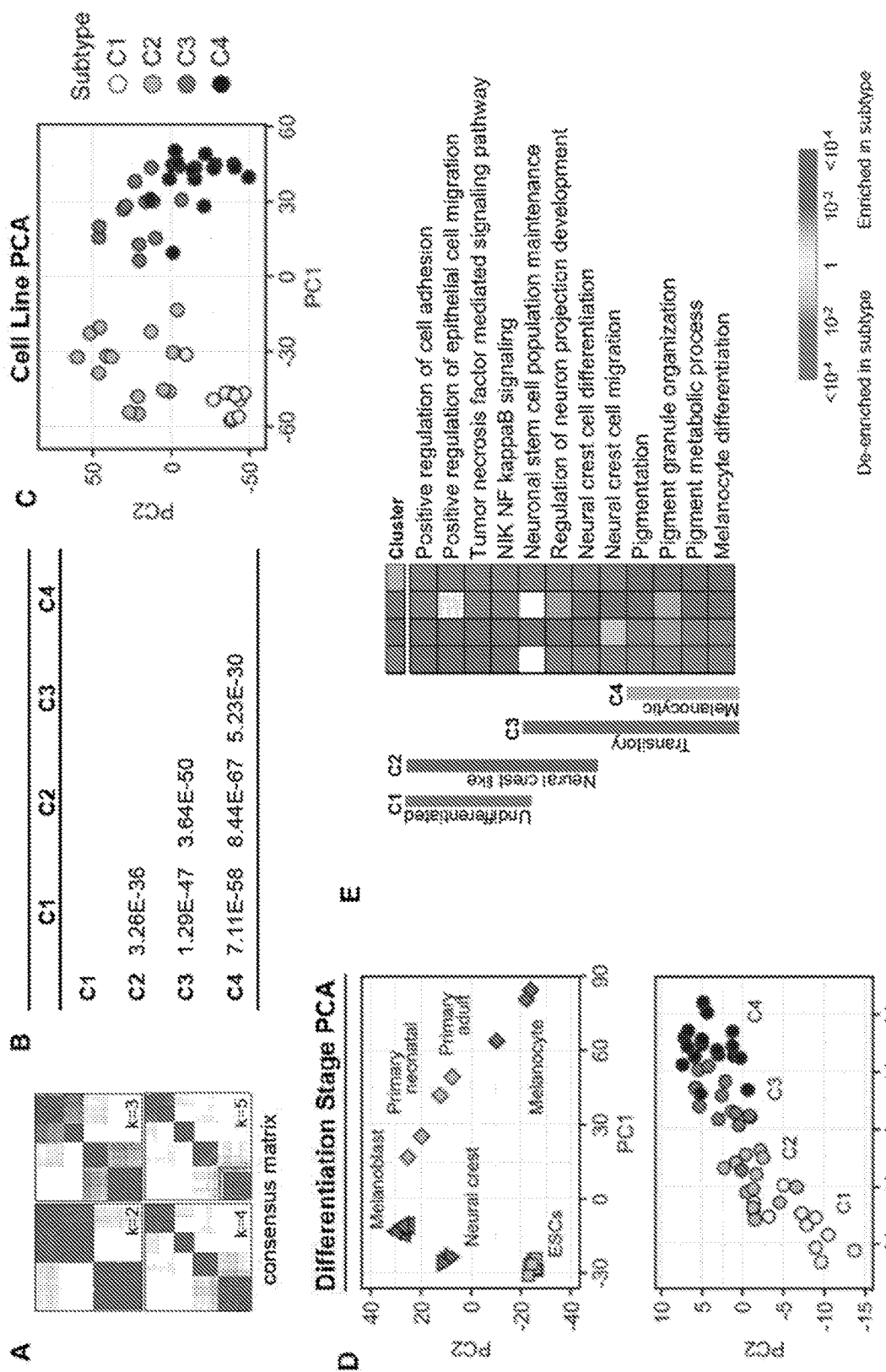
FIG. 1—Identification of four melanoma subtypes related by progressive differentiation. (A) Consensus hierarchical clustering of melanoma cell lines identifies four robust clusters. (B) Pairwise comparisons using SigClust showing that the cluster delineations are statistically significant. (C) PCA of melanoma cell line expression profiles annotated by identified clusters. (D) PCA of gene expression profiles from an in vitro embryonic stem cell (ESC) to melanocyte multistage differentiation system and projection of melanoma cell line expression profiles into melanocyte differentiation stage PCA space show progressive separation of clusters. (E) Heatmap of rank-based enrichment analysis p-values of each cluster vs. the rest showing progressive enrichment patterns of differentiation associated GO gene-sets. (F) Boxplots of select transcription factors and RTK genes in cell line expression profiles showing their subtype-specific patterns. (U: Undifferentiated, N: Neural crest-like, T: Transitory, M: Melanocytic; number in each group: U=10, N=42, T=12, M=17; Kruskal-Wallis ANOVA and Dunn's post hoc test p-values: *≤0.05, ≤0.01, *≤0.001). (G) Enrichment analysis of Melanocytic vs. Transitory subtypes to infer MITF activity in cell lines using an independently identified list of MITF target genes.
Figure 1:
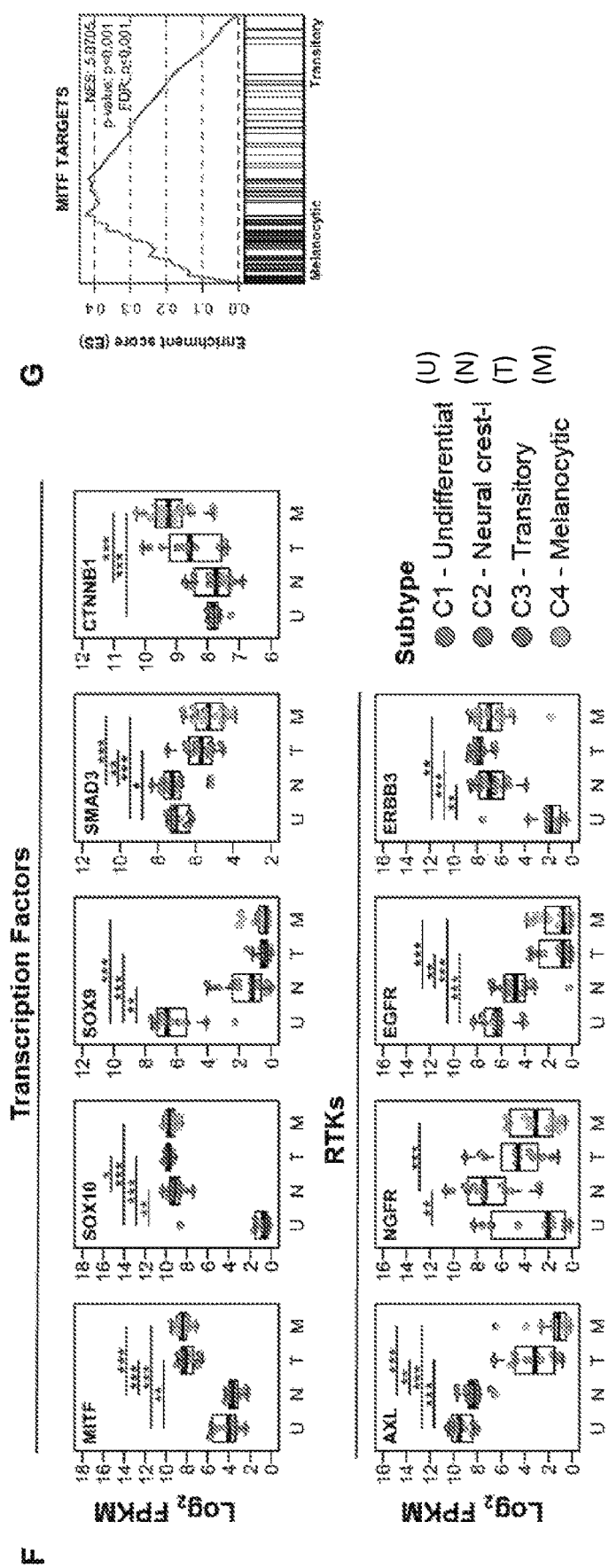

Example 1—Multi-Stage Differentiation Defines Melanoma Subtypes with Differential Vulnerability to Drug-Induced Iron-Dependent Oxidative Stress A. Results 1. Melanoma Subtypes Reflect Four Progressive Differentiation States The inventors performed consensus hierarchal clustering (Monti et al., 2003) of expression profiles from a panel of 53 human melanoma cell lines, including paired acquired resistance sub-lines, established from patient biopsies. The clustering results reveal that cell lines fall robustly into four clusters numbered C1-C4 with no appreciable gain in cluster stability when increasing to higher numbers of clusters (FIG. 1A, Table S1). The inventors next evaluated every combination of cluster pairs using SigClust (Liu et al., 2008) and found each cluster to be significantly different from one another (FIG. 1B). Additionally, all of the clusters arranged into distinct groups by principal component analysis (PCA) (FIG. 1C).

The inventors next investigated how the four melanoma clusters were related by differentiation. A comparative analysis to a human in vitro model of melanocyte differentiation was performed (Mica et al., 2013), where human embryonic stem (ES) cells were induced to differentiate sequentially to neural crest, melanoblast, and melanocyte stages. PCA of these differentiation stage gene expression profiles, which included primary melanocytes as a reference control, shows each stage segregates progressively along a two-dimensional arc-like trajectory with differentiation. Projection of both the melanoma cell lines onto the same melanocyte differentiation stage-defined PCA space similarly separated out the four identified melanoma clusters, indicating a progressive four-stage differentiation relationship (FIG. 1D).

An enrichment analysis of each cluster compared with the remaining three was performed and again observed a progressive pattern of differentiation-related enrichment of GO biological process terms (FIG. 1E, table shown in U.S. Prov. App 62/525,969). C1 was defined as the undifferentiated subtype due to enrichment for invasive phenotype gene sets such as those involving cell adhesion and migration, in addition to inflammation-related gene sets as observed previously in dedifferentiated low MITF melanoma cells (Hoek et al., 2006; Konieczkowski et al., 2014). C2 was defined as the neural crest-like subtype due to enrichment for neural crest-related gene sets. As a generally dedifferentiated subtype, the neural crest-like subtype shared enrichment for the characteristic invasive/inflammation-related gene sets. C3 was defined as the transitory subtype, due to concurrent enrichment of neural crest and pigmentation associated gene sets suggesting a transitional or mixed neural crest to melanocytic state. Finally, C4 is the most differentiated and was defined as the melanocytic subtype, due to loss of the neural crest signature and strong enrichment for pigmentation-associated gene sets.

The inventors next explored the expression patterns of transcription factors and RTK genes across the identified melanoma subtypes (FIG. 1F). As expected, the undifferentiated and neural crest-like subtypes both had low levels of MITF and high levels of AXL. Elevated in these two subtypes were also SMAD3, suggesting a role for TGFβ signaling with the invasive phenotype as previously described (Hoek et al., 2006; Rodeck et al., 1999). These two subtypes do have some notable differences. In the undifferentiated subtype, the inventors observed significantly lower levels of ERBB3, neural crest marker NGFR, and transcription factor SOX10. As SOX10 is a critical neural crest lineage specifying transcription factor essential for melanocyte development (Sauka-Spengler and Bronner-Fraser, 2008), its absence is further supportive of an even less differentiated state. Genes upregulated in the undifferentiated subtype include SOX9 and EGFR, both of which have been shown to be promoted by SOX10 loss (Shakhova et al., 2012; Sun et al., 2014).

The transitory and melanocytic subtypes are a refinement of the previously reported differentiated proliferative phenotype, characterized by higher expression of MITF and lower expression of AXL. Wnt/beta-catenin signaling has been implicated in enhancing MITF target gene expression, and an increased expression of beta-catenin (CTNNB1) is observed across these two subtypes in support of a more mature melanocyte signature (Schepsky et al., 2006). To evaluate if there is differential MITF activity between these two subtypes, the inventors performed enrichment analysis using previously described MITF target genes to infer activity (Hoek et al., 2008). The melanocytic subtype showed stronger enrichment of these MITF target genes (FIG. 1G), supportive of greater differentiation state within this subtype.

Figure 8:
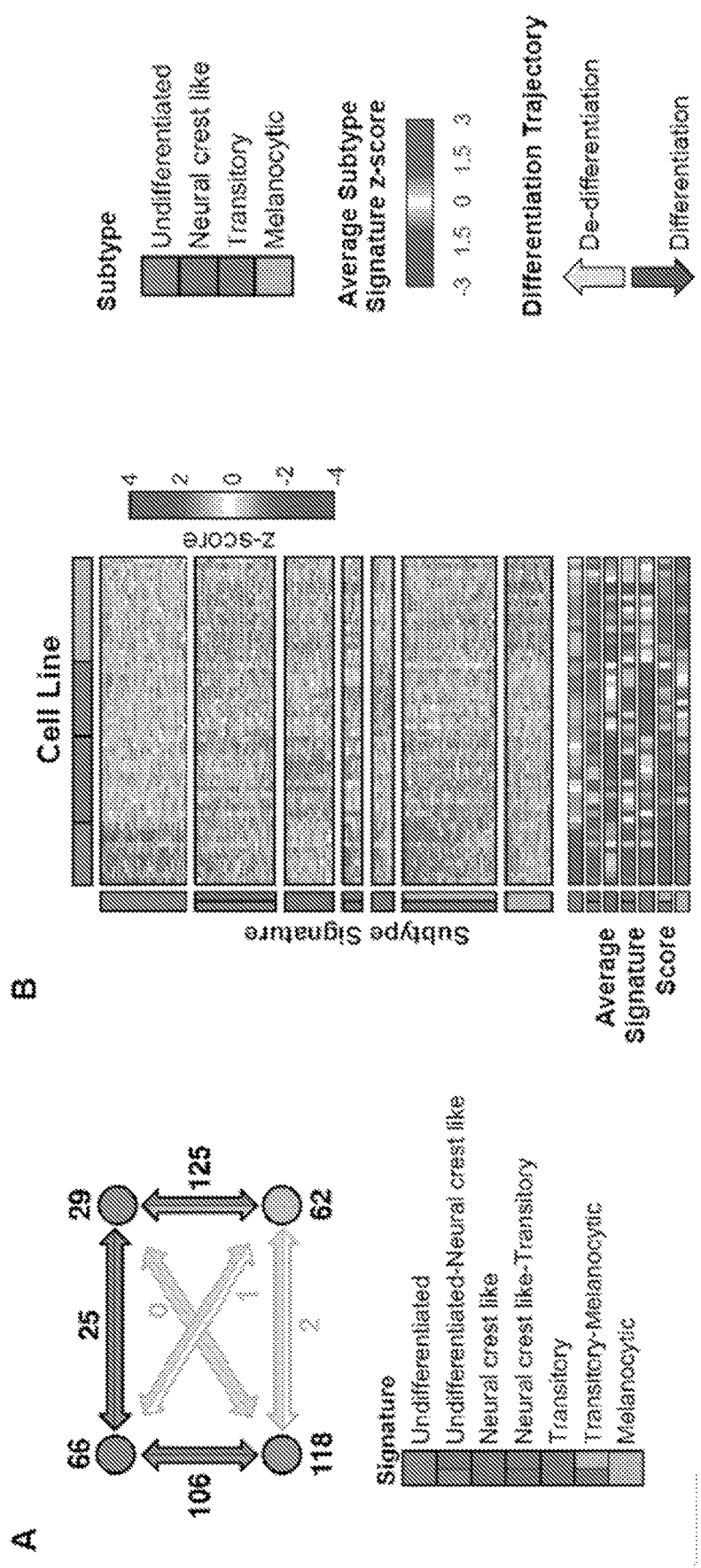
FIG. 8—Identification of subtype signatures for visualization of treatment-induced dedifferentiation. (A) Numbers of differentially upregulated genes in each individual subtype or shared between pairs of subtypes when compared to the remaining subtypes ($\log_2$ fold change ≥1.5, 5% false discovery rate). (B) Heatmap of subtype gene signatures in cell line gene expression profiles. Average of each subtype signature z-score are shown at the bottom. (C) Heatmap of signature genes, average signature z-scores, and differentiation trajectory position changes for matched parental (P) or single (DR) or double drug (DDR) resistance samples of the three indicated cell lines. Single drug: vemurafenib (BRAFi); double drug: vemurafenib+selumetinib (MEKi). (D) Heatmap of signature genes, average signature z-scores, and differentiation trajectory position changes at baseline (B), on-treatment (OT) or disease progression (DP) for 11 melanoma patient treatment cases. All patients were on double drug (dabrafenib+trametinib (BRAFi+MEKi)) therapy with the exception of Pt2 on single drug therapy (vemurafenib (BRAFi)). On treatment samples are 12±5 days.
Figure 8:
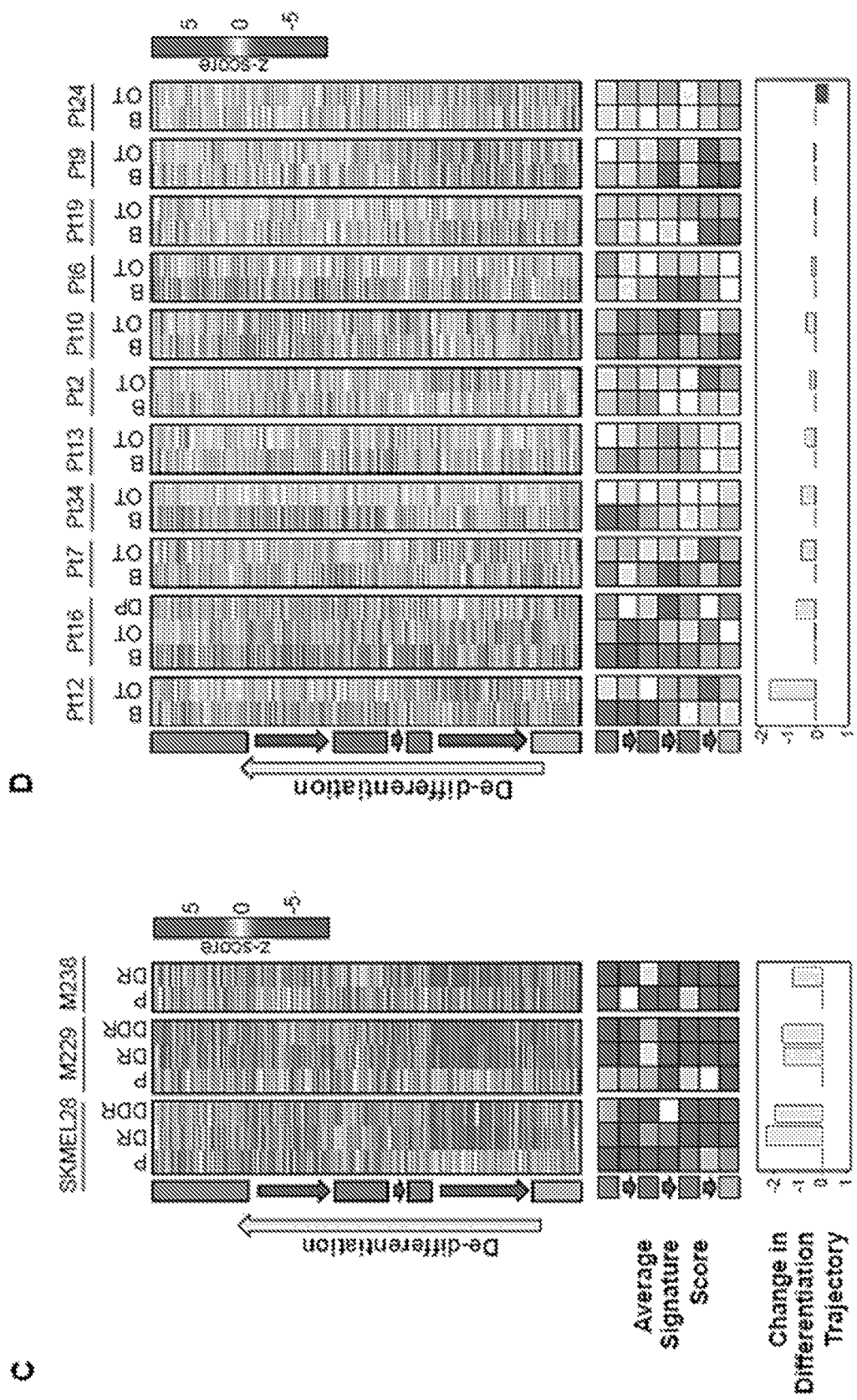

2. Treatment Induced Dedifferentiation in the Context of the Four-Stage Differentiation Model The results thus far illustrate that melanoma cells can exist at distinct baseline differentiation states. Melanoma cells are highly plastic and can dedifferentiate in response to MAPK pathway inhibition and pro-inflammatory signaling from increased immune infiltration during immunotherapy. To relate these treatment-induced differentiation transitions to the subtypes, the inventors defined distinguishing transcriptional signatures for each subtype. For each signature, differentially upregulated genes specific to each subtype were determined using a log 2 fold change threshold of 1.5 and 5% false discovery rate (Table S4). Additionally, the inventors tested the extent of shared differentially expressed genes between 'adjacent' subtypes compared to other subtype pairings. Highly consistent with the interpretation of the subtypes as four progressive differentiation states, the only cluster pairings that generated an appreciable signature were between sequential clusters in the two-dimensional arc-like trajectory model (FIG. 8A-B).

Figure 2:
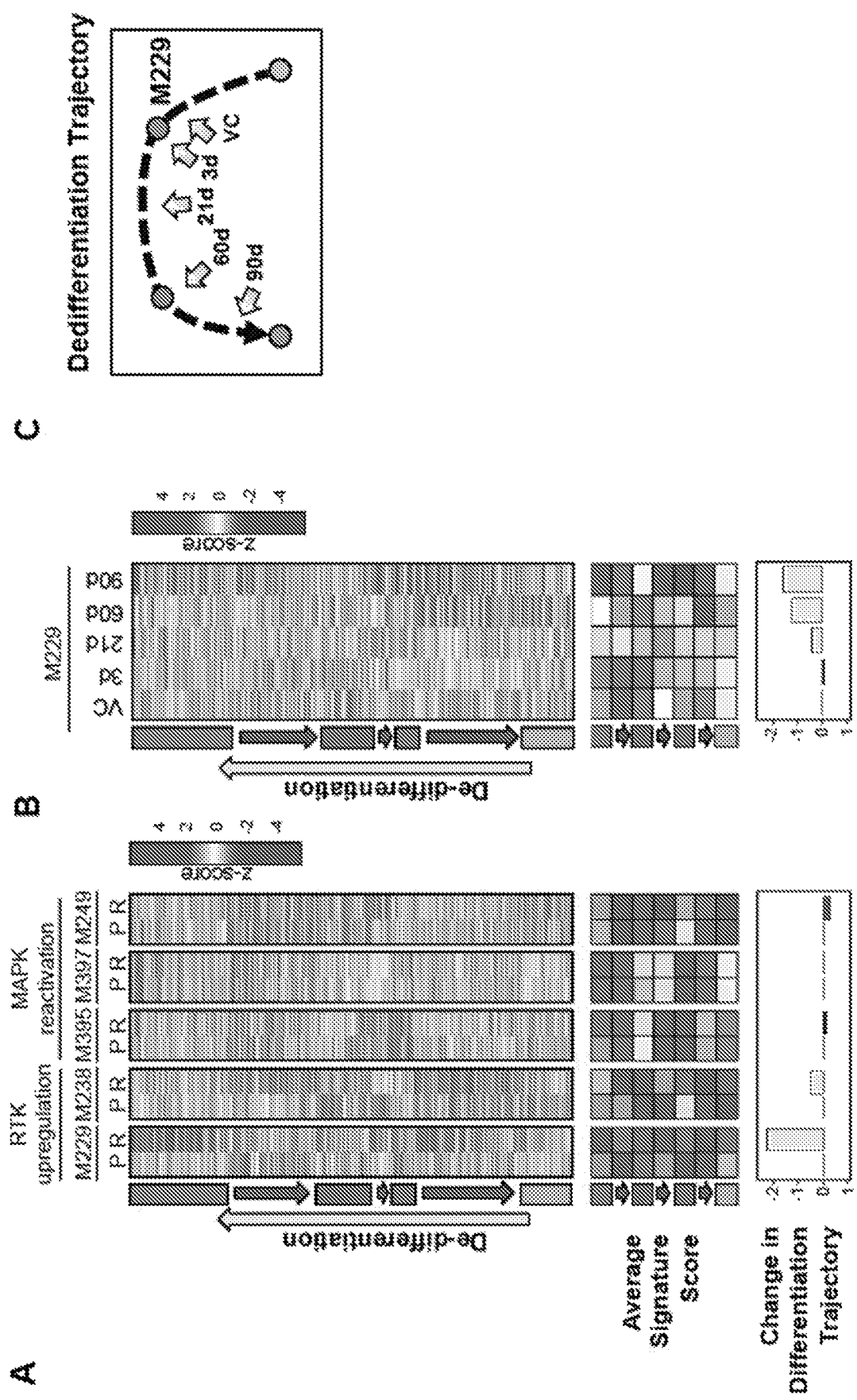
FIG. 2—Treatment-induced dedifferentiation in the context of the four-stage differentiation model. (A) Heatmap of signature genes, average signature z-scores, and differentiation trajectory position changes for matched parental and resistant cell lines with different indicated mechanisms of vemurafenib acquired resistance. (B) Heatmap of signature genes, average signature z-scores, and differentiation trajectory position changes in timecourse of M229 melanoma cell line treated with vemurafenib compared to vehicle control (VC, DMSO) (C) Schematic representing progressive dedifferentiation along our two-dimensional model with increased treatment time with vemurafenib. (D) Heatmap of signature genes, average signature z-scores, and differentiation trajectory position changes for murine HCmel3 tumors or cell lines with treatment control or relapse from adoptive transfer of antigen specific T cells. Dark grey arrows represent increased differentiation state and the light grey arrow indicates the treatment induced de-differentiation direction.
Figure 2:
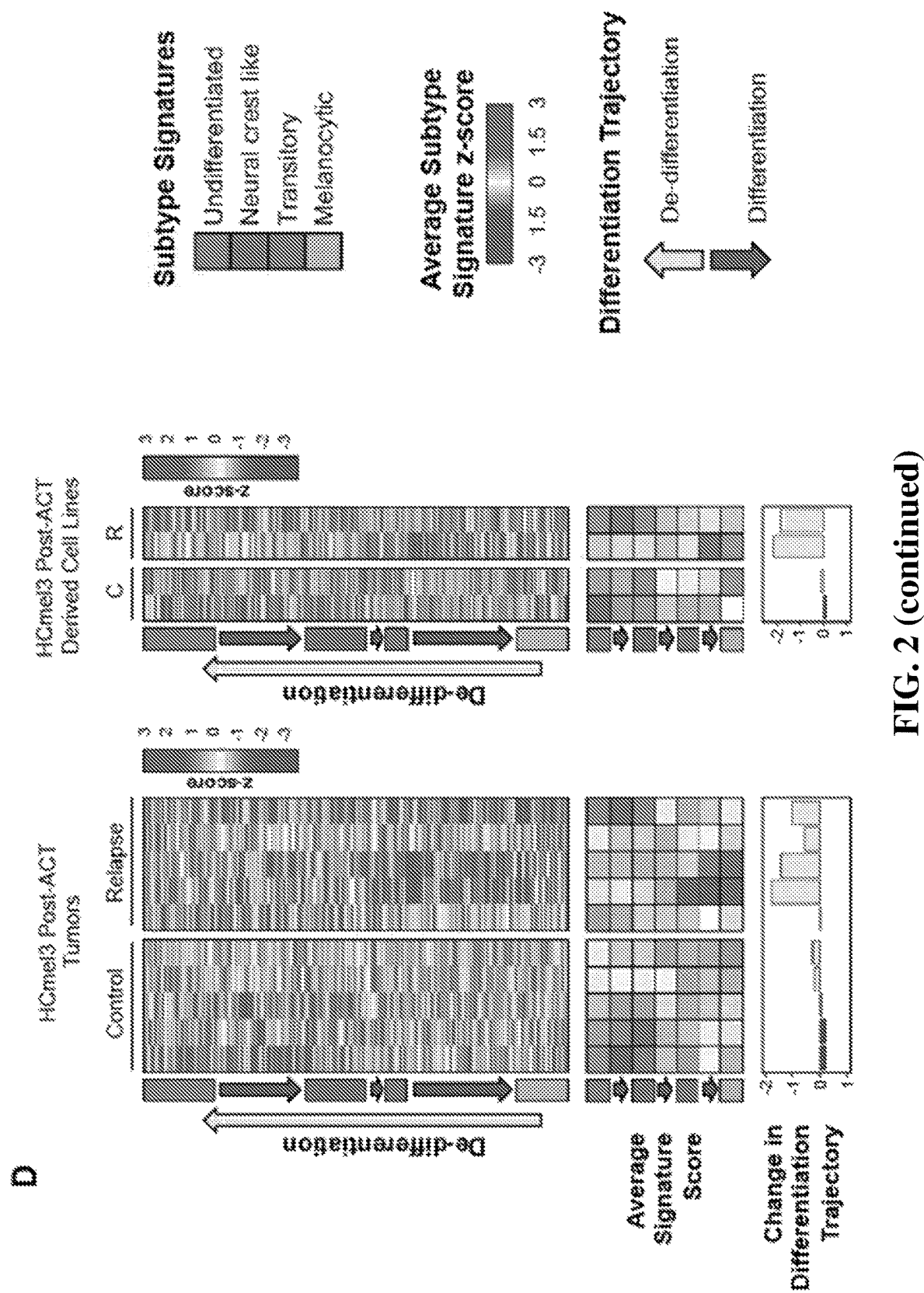

These signatures were first applied to investigate dedifferentiation-associated acquired resistance to MAPK pathway inhibitors that occur through RTK-upregulation (Müller et al., 2014). To quantify the degree of treatment-induced dedifferentiation, the inventors calculated a differentiation trajectory position score for each sample using a "center of mass" approach (Methods). The change in the differentiation trajectory score for each sample from respective controls thus indicates the level of dedifferentiation. In the BRAF mutant cell lines M229P and M238P, the inventors observed that cell lines can begin with different initial differentiation stages as defined by their subtype signatures, but move substantially towards the undifferentiated signature upon acquired resistance to vemurafenib (M229R, M238R) (FIG. 2A). Similar results were observed in an independent study of RTK-driven single and double drug (BRAFi and MEKi) resistant cell lines (FIG. 8C). To evaluate the temporal changes that occur with the acquisition of resistance, the inventors performed a vemurafenib time-course study of M229P, which starts as a transitory subtype but switches to an undifferentiated subtype in M229R. Supportive of our differentiation model, treatment with vemurafenib produced gene expression changes that marked progressive dedifferentiation with time through our subtype signatures towards the undifferentiated subtype (FIG. 2B-C). This progression towards the undifferentiated subtype is consistent with a recent report of stepwise reprogramming and stable resistance acquired through loss of SOX10-mediated differentiation (Shaffer et al., 2017). Using the subtype signatures, dedifferentiation in patient biopsies was detectable on-treatment during double drug MAPK therapy, and upon resistant disease progression (FIG. 8D) (Kwong et al., 2015). As a negative control, genomic alterations that directly reactivate the MAPK pathway through NRAS mutation (M249R) or BRAF alternative splicing (M395R, M397R) do not show observe any differentiation changes (FIG. 2A) (Nazarian et al., 2010).

The inventors next applied the subtype signatures to investigate immunotherapy resistance occurring through inflammation-induced dedifferentiation. Such dedifferentiation has been shown to occur in vivo in a mouse model of adoptive cell transfer (ACT) using transgenic cytotoxic T cells targeting the melanocytic antigen gp100 (Landsberg et al., 2012). In this system, dedifferentiation decreased the presentation of the tumor antigen, as scored by loss of melanocytic biomarkers (gp100, TRP2), leading to tumor progression. As expected, the inventors observed greater expression of dedifferentiation signatures within the relapse group compared to the control both in the tumors and in tumor-derived cell lines (FIG. 2D). Collectively, these results show that the differentiation framework is consistent with and can help measure and visualize dedifferentiation associated with modern melanoma therapy resistance.

3. Melanoma Classifier Identifies Consistent Subtypes in Cell Lines and Tumors

Figure 3:
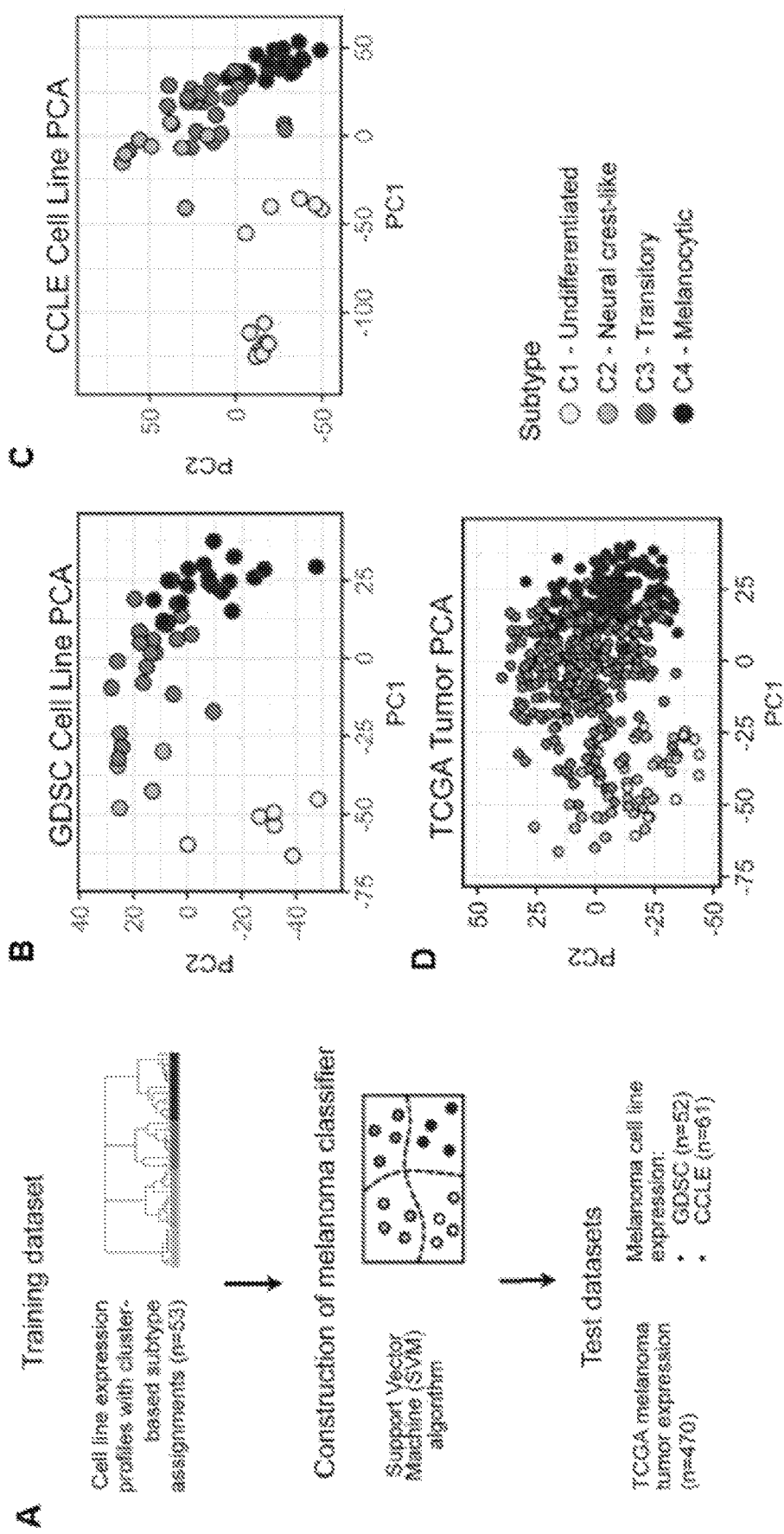
FIG. 3—Melanoma classifier identifies consistent subtypes in cell Lines and tumors. (A) Schematic of the melanoma subtype classifier pipeline. (B-D) PCA of GDSC (B), CCLE (C) and TCGA (D) datasets annotated by the predicted cluster assignment. For the TCGA dataset, immune and keratin associated genes were removed for melanoma specific analysis.

The dedifferentiation response to MAPK pathway inhibition and to immunotherapy suggests that targeting the dedifferentiated state could be a viable approach to overcome resistance. As the multi-stage subtypes provide a refinement of melanoma differentiation, the inventors sought to identify differentiation-associated relationships to drug sensitivity. To integrate publicly available pharmacogenomics cell line resources with our cell line dataset, the inventors built a predictive model trained on the cell line expression profiles to predict subtypes in other cell lines (FIG. 3A). The inventors used a support vector machine (SVM) classifier combined with the "top-scoring pairs" (TSP)-based method (Shi et al., 2011) to capture the relative expression relationship between genes and define predictive signatures (Methods). This approach helps ensure that different data sources, processing methods, and normalization strategies are compatible with the prediction model and to minimize the test-set bias. The inventors applied the prediction model to the Cancer Cell Line Encyclopedia (CCLE) and Genomics of Drug Sensitivity in Cancer (GDSC) independent datasets. Within the 29 cell lines shared between these two datasets, 27 were identically predicted (93.1%) and the other two only shifted by 1 stepwise differentiation state. PCA of each dataset annotated by the prediction results show similar differentiation trajectory patterns as in the original analysis (FIG. 3B-C), further supporting the robustness of the four-step differentiation framework.

Figure 9:
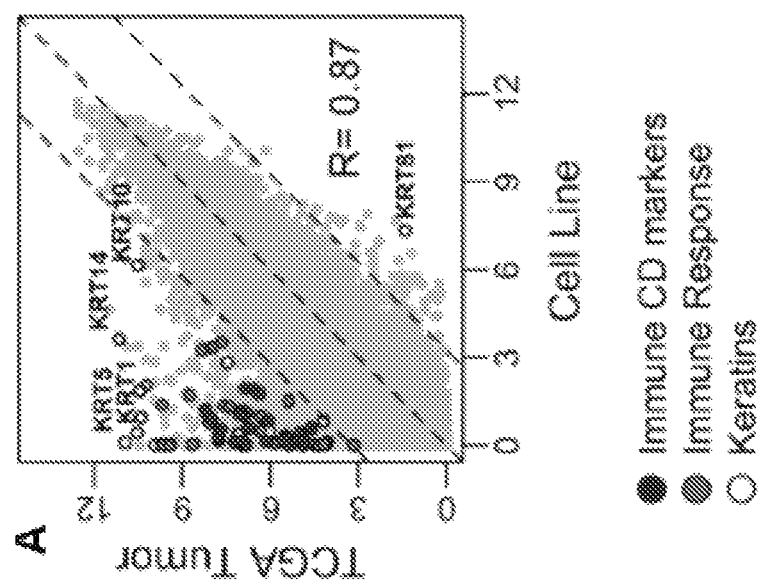
FIG. 9—Removal of confounding signatures from bulk tumors yields similar results as cell lines. (A) Scatterplot of maximum gene expression in the melanoma bulk tumors and cell lines show strong concordance. Maximum expression was defined as the $95^{th}$ percentile value to reduce the effects of outliers. Dashed lines represent two standard deviations from the diagonal. (B) PCA of bulk tumor global gene expression profiles annotated by predicted subtypes after stepwise removal of confounding signatures. PCA figures below are colored by CD3E expression to show the influence of immune infiltration and KRT5/14 (averaged expression) to show the influence of keratinocyte-type keratins and tissue biopsy source throughout each step. Initial PCA showed a strong influence of immune infiltration and after removal of an immune correlated gene signature, PCA of the remaining gene expression reveal secondary bias from keratinocyte-type keratins likely from the skin due to overlap with primary tissue as the biopsy site. PCA of global tumor expression annotated after removal of both immune and keratin confounded genes, shows a decreased bias from immune, keratin, and the tissue biopsy site and increased similarity to cell line-clustering patterns. (C) Projection of bulk tumor expression profiles into melanoma cell line-based PCA space from FIG. 1B.
Figure 9:
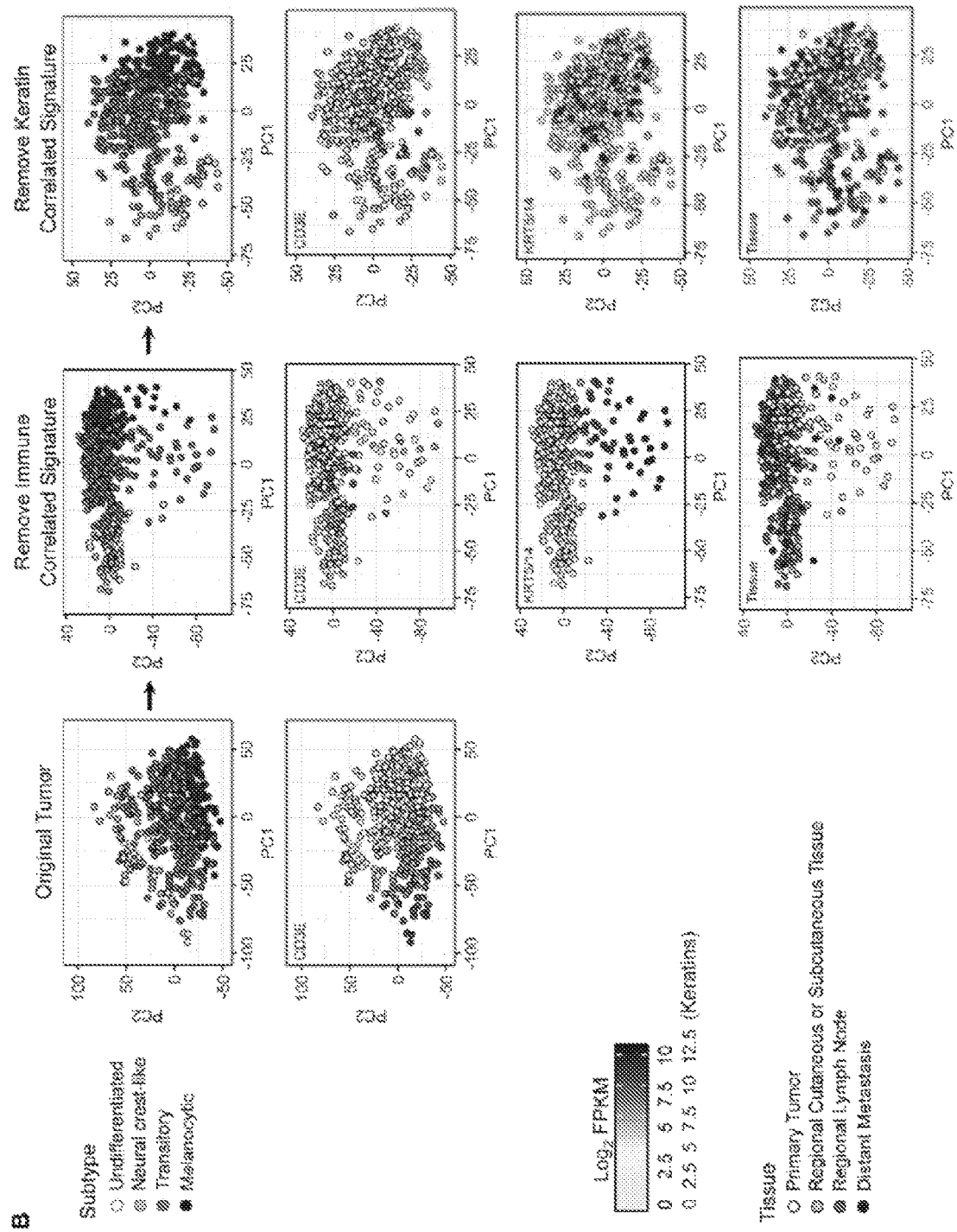
Figure 9:
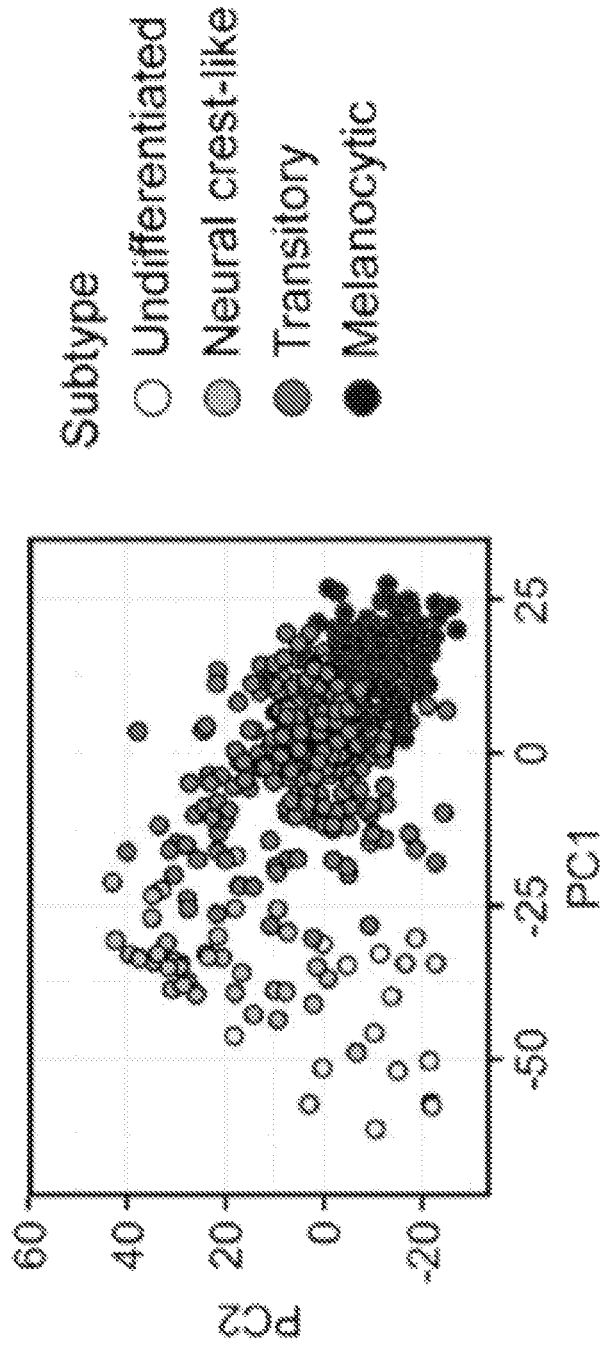

To evaluate the relevance of the subtypes in patient tumors, the inventors extended the cell line-trained classifier to the TCGA skin cutaneous melanoma (SKCM) bulk tumor expression profiles for melanoma-specific sub-classification (table shown in U.S. Prov. App 62/525,969). The inventors evaluated the similarity of gene expression between the cell lines and bulk tumors by comparing the maximum expression of each gene and observed strong concordance (R=0.87), confirming that cell lines do retain tumor expression patterns (FIG. 9A). The residual disparity is mostly from genes expressed higher in tumors than in cell lines that are contributed by non-melanoma cells within the tumor bulk. For example, these genes included highly immune-specific CD markers and cytokines indicative of immune infiltration. Additionally, some tumors had high expression of keratinocyte-type keratin pairs (KRT1/KRT10 and KRT5/KRT14), which is found almost specifically in stratified epithelia such as the epidermis (Moll et al., 2008). When the inventors removed these two confounding signatures (FIG. 9B, Methods), PCA of the bulk tumor expression profiles show analogous arc-like trajectory differentiation subtype patterns consistent with the pure cell line cases, further supporting the progressive relationship between these melanoma subtypes (FIG. 3D). Similar patterns were also observed in a parallel approach by projection of the tumor profiles onto the cell line-defined PCA space (FIG. 9C, FIG. 1D), which emphasizes melanoma-specific genes and reduces the influence of non-melanoma cell genes within the tumor.

Figure 10:
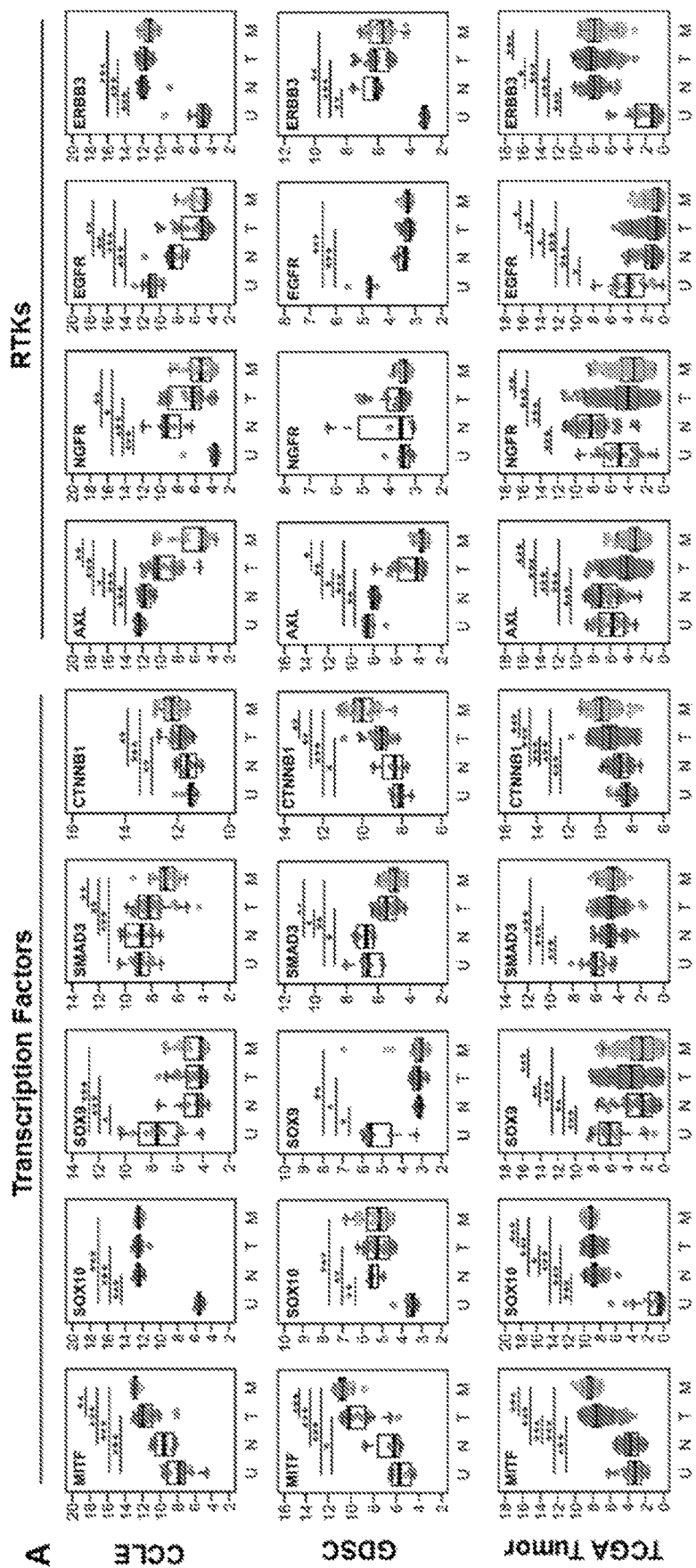
FIG. 10—Differentiation marker patterns across subtypes are consistent among independent test datasets. (A) Boxplots of select transcription factors and RTK gene expression showing their subtype-specific patterns. (B) Enrichment analysis of Melanocytic vs. Transitory subtypes to infer MITF activity in CCLE, GDSC, and TCGA datasets. (C) Beta values of select genes from the GDSC cell lines and TCGA tumor dataset grouped by predicted subtype. (U: Undifferentiated, N: Neural crest-like, T: Transitory, M: Melanocytic; number in each group, GDSC: U=12, N=8, T=22, M=19; GDSC: U=6, N=4, T=19, M=23; TCGA: U=16, N=37, T=294, M=123; Kruskal-Wallis ANOVA and Dunn's post hoc test p-values: *≤0.05, ≤0.01, *≤0.001)
Figure 10:
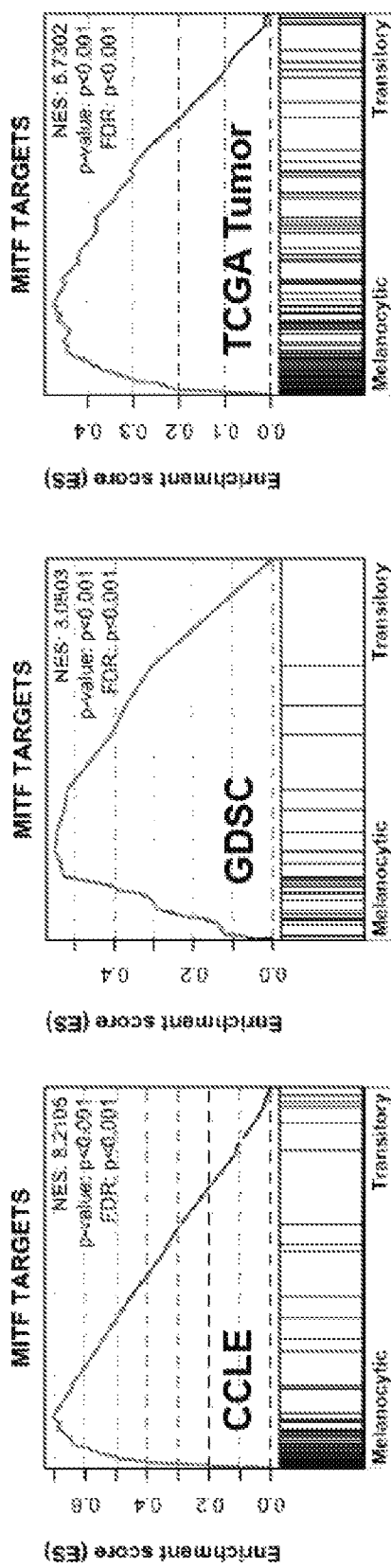
Figure 11:
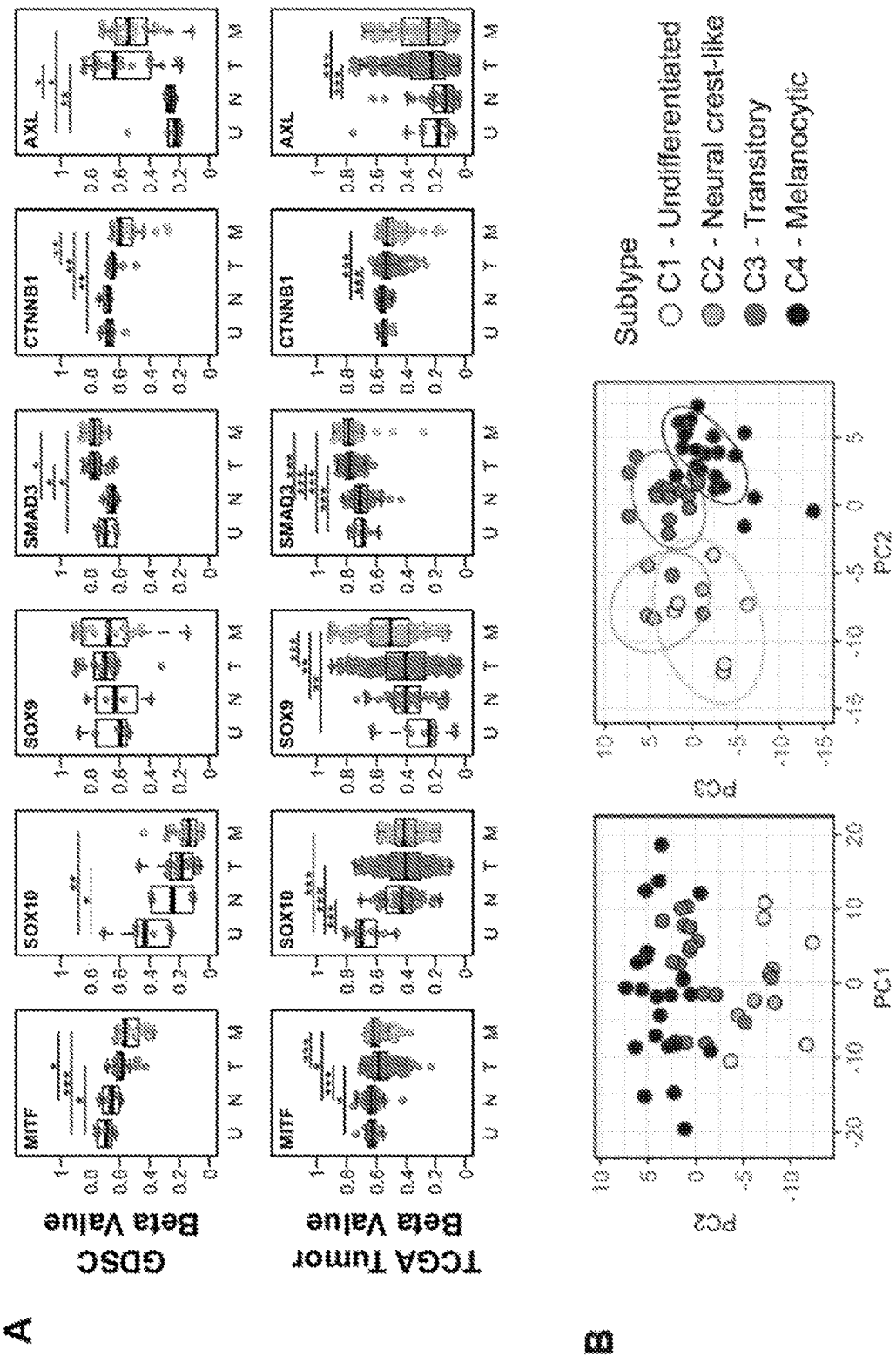
FIG. 11—Epigenetic changes in DNA methylation mirror the transcriptional programs of differentiation. (A) Beta values of select genes from the GDSC cell lines and TCGA tumor dataset grouped by predicted subtype. (U: Undifferentiated, N: Neural crest-like, T: Transitory, M: Melanocytic; number in each group, cell lines: U=6, N=4, T=17, M=23; tumors: U=16, N=37, T=294, M=123; Kruskal-Wallis ANOVA and Dunn's post hoc test p-values: *≤0.05, ≤0.01, *≤0.001). (B) PCA based on methylation beta values from the GDSC cell line dataset and annotated by predicted subtype. Plot of PC2 vs. PC3 show subtype patterns similar to the arc-like differentiation trajectory observed with the gene expression PCA. Ellipses mark 80% confidence interval based on multivariate t-distribution. PC1 reflects another methylation signal not explained by the subtypes.

Collectively, these results demonstrate the consistency of these subtype relationships detectable in both melanoma cell line and tumor cohorts independently. These subtype predictions also show similar expression patterns of RTKs, transcription factors, and inferred MITF activity across all datasets (FIG. 10A-B). As TCGA tumor and GDSC cell line profiles have matching methylation data, the inventors utilized this data integration to explore the extent the differentiation-associated expression differences could be regulated at the methylation level. The inventors found promoter methylation beta values that are inversely correlated with expression in both cell lines and tumors for the genes AXL, MITF, SOX10, SMAD3 and CTNNB1 (FIG. 11A). Furthermore, PCA of the genome-wide promoter methylation data in the GDSC dataset revealed a similar arc-like, progressive differentiation subtype trajectory as in the expression-based analysis (FIG. 11B). These results match the generally expected trend for methylated promoters to inhibit transcription and are supportive of epigenetic regulation of differentiation as previously appreciated (Lauss et al., 2015; Shaffer et al., 2017).

Figure 12:
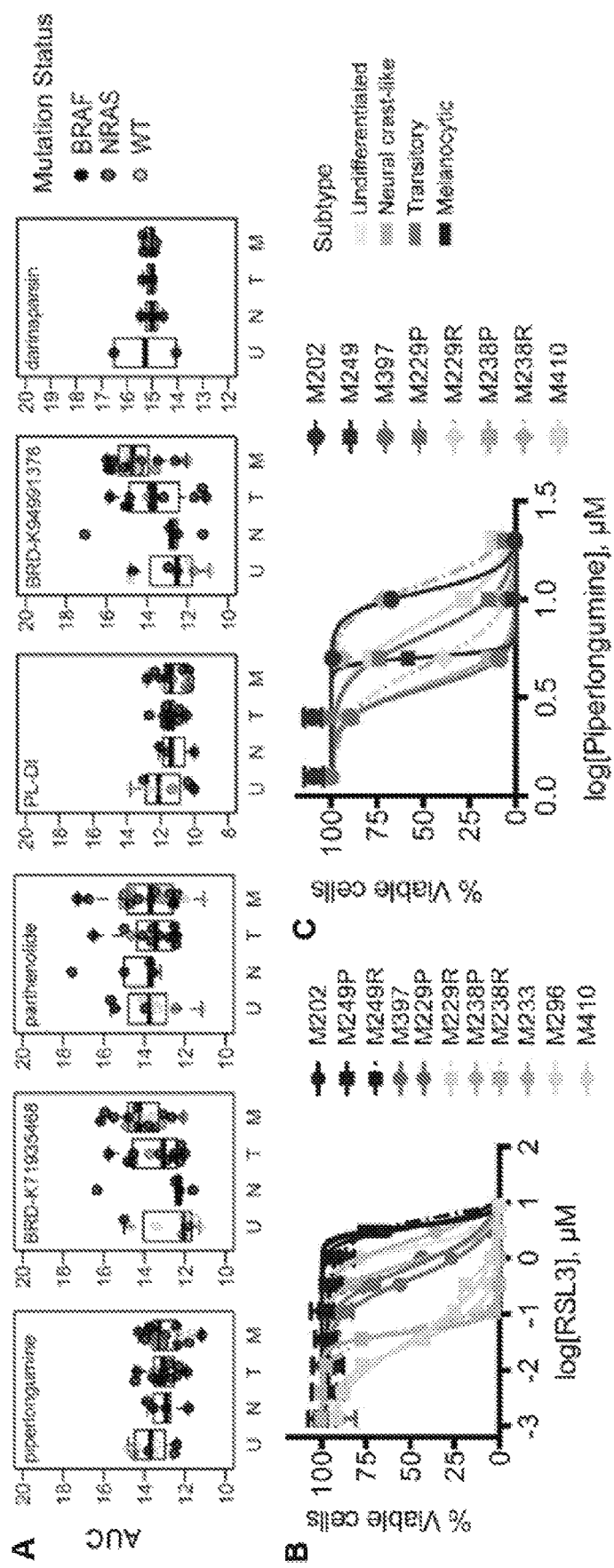
FIG. 12—Confirmation of ferroptosis in undifferentiated signature cell lines. (A) AUC values from the CTRP for other ROS generating drugs that do not induce ferroptosis do not show any subtype trends. (U: Undifferentiated, N: Neural crest-like, T: Transitory, M: Melanocytic; Kruskal-Wallis ANOVA and Dunn's post hoc test p-values: *≤0.05, ≤0.01, *≤0.001) (B) Validation of RSL3 sensitivity patterns across indicated cell lines. (C) Validation of no difference in sensitivity among subtypes and vemurafenib resistant lines when treated with piperlongumine. Undifferentiated cell lines include M229R, M296, and M410; Neural Crest-like cell lines include M233, M238P, and M238R; Transitory cell lines include M397 and M229P; Melanocytic cell lines include M202, M249P, and M249R. (D) Cytotoxicity assay using the Incucyte Cytotox Red reagent showing rapid cell death with erastin treatment that can be prevented with DFO or Trolox. (E) Trypan blue exclusion assay of 24 hr erastin or staurosporine treatment with or without caspase inhibitor Z-VAD-FMK pre-treatment for 1 hr. The first 2 bars of each of the bar graph represents DMSO. The third and fourth bars of each of the bar graph represents 5 µM Erastin. The fifth and sixth bars of each bar graph represents 1 µM Staurosporine. (F-G) Mean fluorescence intensity after 10 hr erastin treatment across cell lines by flow cytometry using BODIPY-C11 probe to measure lipid ROS (F) and CM-H2DCFDA probe to measure cytosolic ROS (G). Data shown in barplots represent mean±sem of three independent experiments. For F-G: the first bar of each bar graph represents DMSO. The second bar of each bar graph represents 5 µM Erastin. The third bar of each bar graph represents DFO. The fourth bar of each bar graph represents DFO+Erastin. For B-G: Undifferentiated cell lines include M229R, M296, and M410; Neural Crest-like cell lines include M233, M238P, and M238R; Transitory cell lines include M397 and M229P; Melanocytic cell lines include M202, M249P, and M249R.
Figure 12:
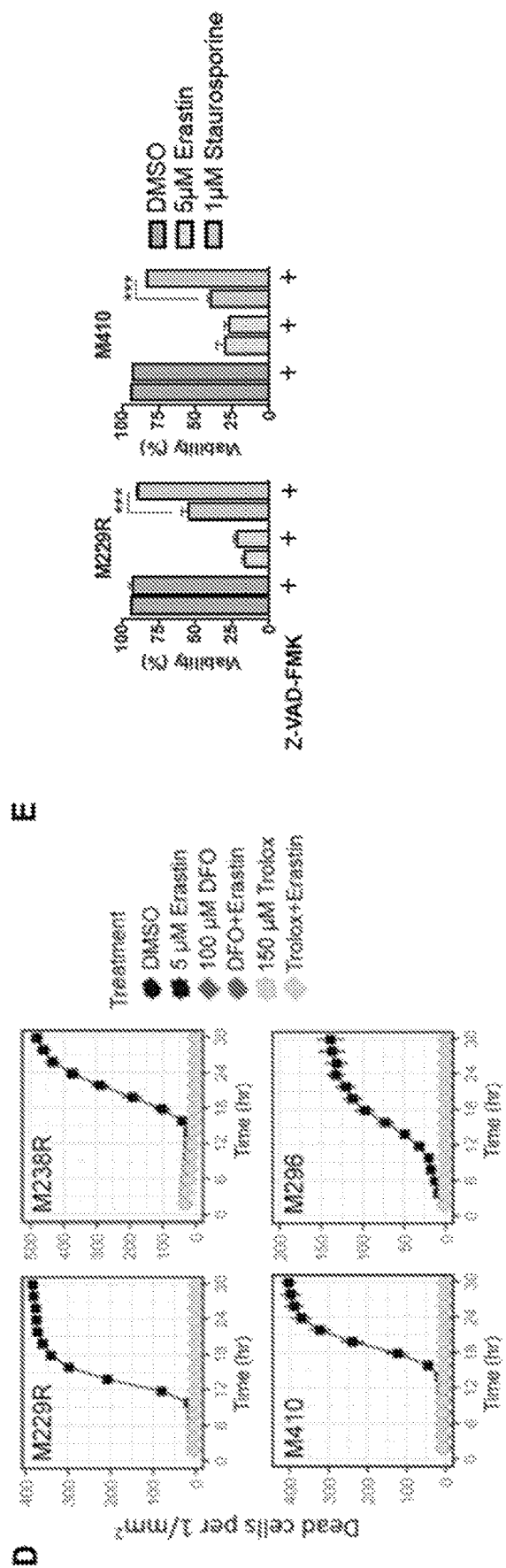
Figure 12:
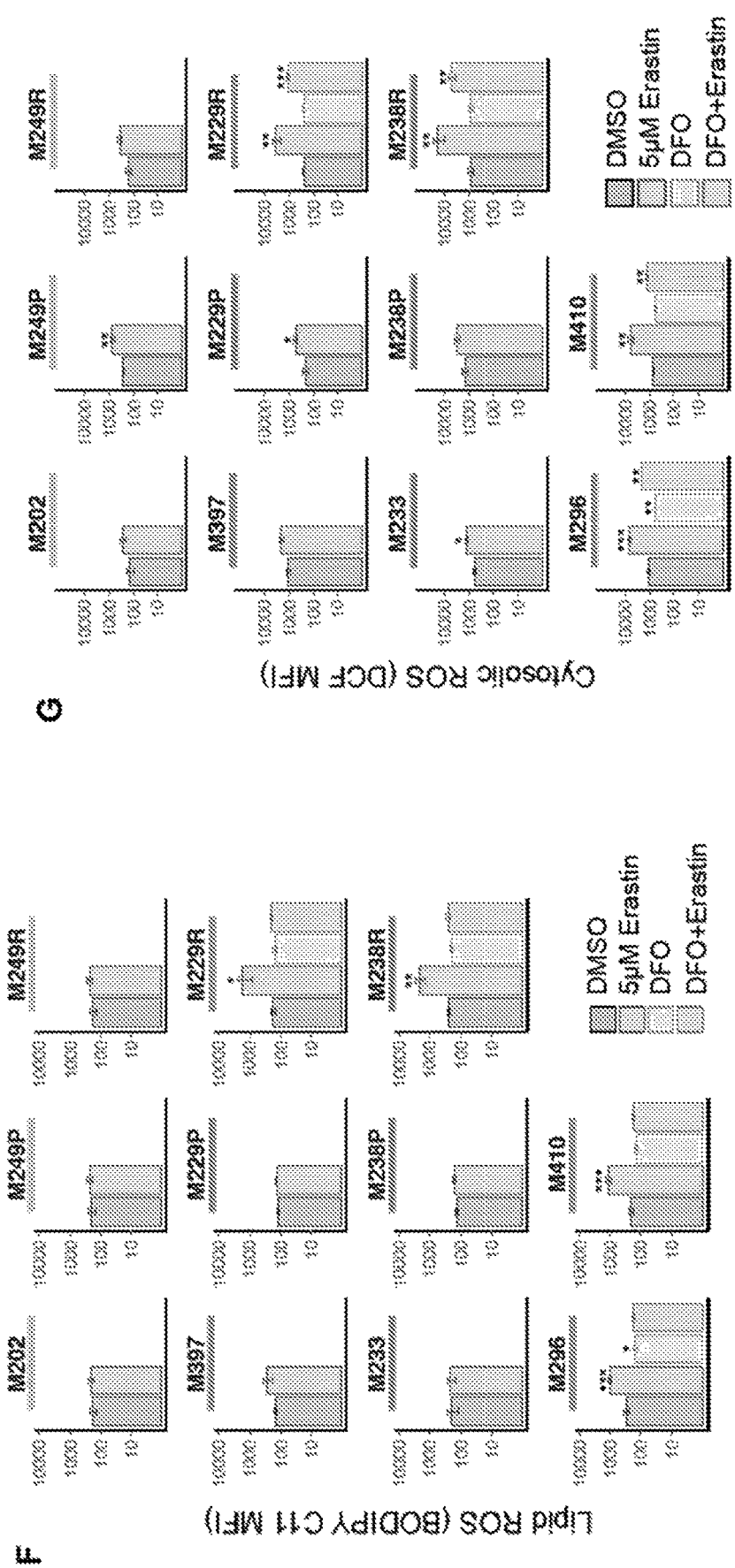
Figure 13:
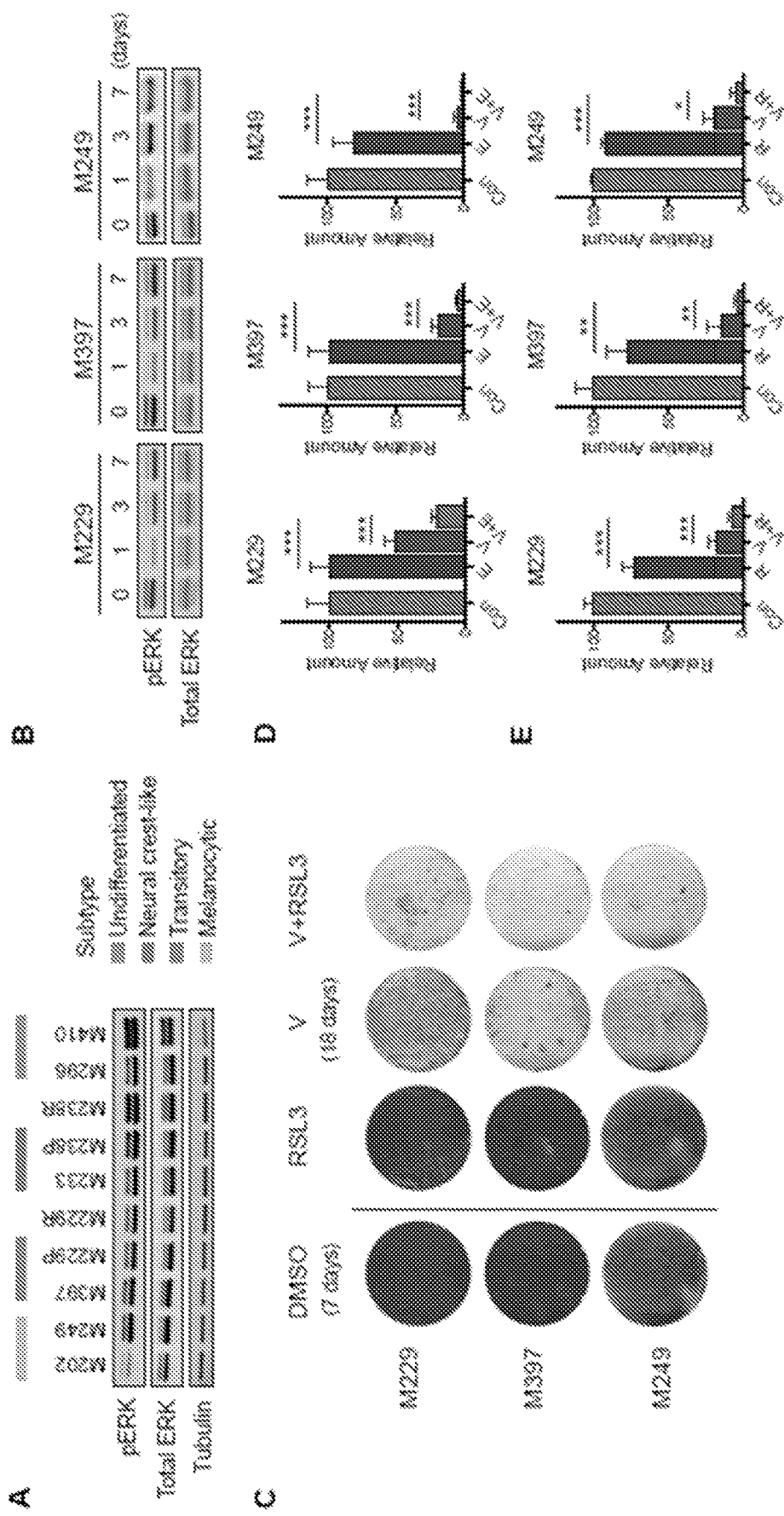
FIG. 13—Reduction in persistent dedifferentiated melanoma cells upon combination treatment with RSL3. (A)
Figure 13:
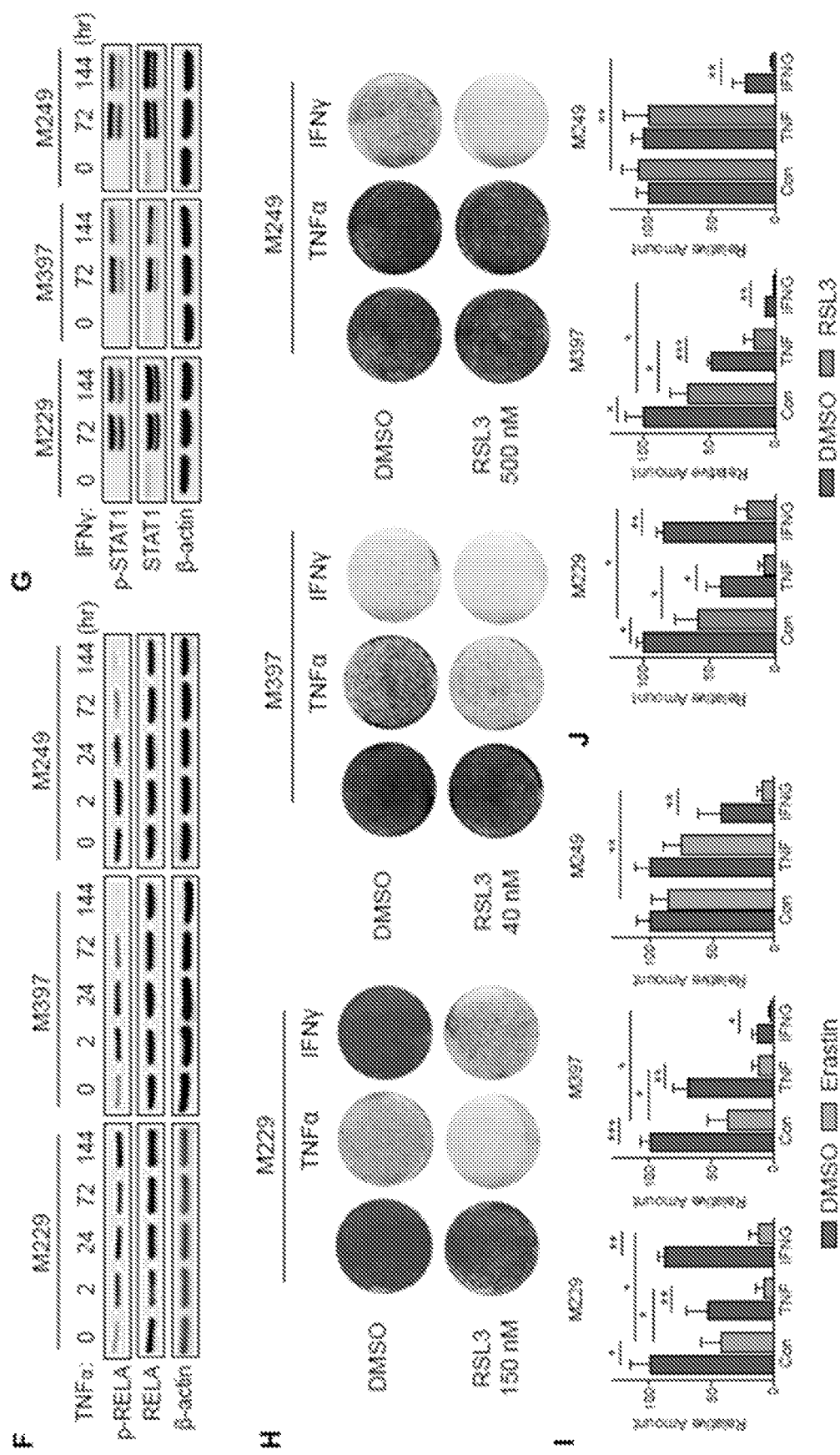

4. Pharmacogenomics Integration Reveal Inverse Relationship Between Differentiation State and Sensitivity to Ferroptosis Inducing Drugs Through the prediction of subtypes from the CCLE and GDSC dataset, the inventors utilized the matching drug sensitivity profiles available from the pharmacogenomics-based Cancer Therapeutics Response Portal (CTRP) (Seashore-Ludlow et al., 2015). The inventors applied an ANOVA filter (P<0.01) to identify drugs that exhibited subtype-specific sensitivity and performed hierarchical clustering to identify clusters with a similar mechanism of action to increase confidence of target specificity. Interrogation of the compounds screened revealed that with increased dedifferentiation status there was an increased sensitivity to all ferroptosis inducing drugs (n=4/4) irrespective of mutation status (FIG. 3A). These compounds are erastin, (1S,3R)-RSL3, ML162, and ML210 (FIG. 3B). Small molecule compounds (1S,3R)-RSL3, ML162, ML210 induce ferroptosis by direct inhibition of GPX4, while erastin indirectly inhibits GPX4 through depletion of glutathione by targeting the System Xc-transporter (Dixon et al., 2012; Yang et al., 2014). In contrast, the inventors did not observe subtype-specific sensitivity in the subclass of ROS inducing drugs that do not induce ferroptosis (FIG. 12A).

Additional small molecule cell death-inducing compounds having specificity for dedifferentiated melanoma cells include Ki8751 (a VEGFR2 kinase inhibitor), SGX-523 (a c-Met kinase inhibitor (RTK inhibitor)), AZD7762 (a Chk1 & Chk2 inhibitor-Checkpoint kinase 1 and 2 inhibitor), KW-2449 (a multi-kinase inhibitor—a FLT3 inhibitor), NVP-TAE684 (a ALK kinase inhibitor), AZD4547 (a Pan FGFR kinase inhibitor (RTK inhibitor)), TG-101348 (a JAK2 kinase inhibitor), bleomycin A2 (a DNA damaging agent), axitinib (a VEGFR kinase inhibitor), cytochalasin B (an inhibitor of actin polymerization), dasatinib (a Src kinase inhibitor), SNX-2112 (an HSP90 inhibitor), Semagacestat (a γ-secretase inhibitor), CHIR-99021 (a GSK-3 inhibitor), B02 (a RAD51 inhibitor), olaparib (a PARP inhibitor), silmitasertib (a casein kinase II (CK2) inhibitor), tanespimycin (a HSP90 inhibitor), nintedanib (a tyrosine-kinase inhibitor, targeting VEGFR, FGFR, and PDGFR), ML031 (a Sphingosine-1-phosphate (S1P) agonist), canertinib (a ErbB family inhibitor (EGFR, HER-2, ErbB-4)), SMER-3 (a MET30 Antagonist), BCL-LZH-4 (a inhibitor of Bcl-2 family proteins), SN-38 (a topoisomerase inhibitor), tamatinib (an inhibitor of immunoglobulin E (IgE)- and IgG-mediated activation of Fc receptor signaling), ML334 diastereomer (a small molecule inhibitor of the Keap1-Nrf2 interaction), analogues, salts and derivatives thereof.

Due to the increased levels of System Xc-observed across various cancer types and its potential as a therapeutic target (Doxsee et al., 2007; Guo et al., 2011; Lo et al., 2008; Timmerman et al., 2013), the inventors focused on exploring the treatment of melanoma cells with erastin, as well as with the GPX4 targeting agent RSL3. As predicted, there was increased sensitivity to erastin and RSL3 with dedifferentiation (FIG. 4C and FIG. 14C-F). The melanocytic subtype cell lines M202 and M249 were highly resistant to erastin. Transitory subtype lines M229P and M397, and neural crest-like subtype lines M233 and M238P were only moderately sensitive. In contrast, the undifferentiated subtype cell lines M410, and RTK acquired resistance lines M229R and M238R were highly sensitive. While M238R did not switch completely to be classified as the undifferentiated subtype, analysis of subtype signatures did reveal greater expression of the undifferentiated signature and thus dedifferentiation when compared to the parental line (FIG. 2A). As a negative control, this increase in sensitivity was not observed in M249R, which achieves resistance to vemurafenib through acquisition of an NRAS mutation. However, there were also other factors that affect sensitivity since M296 exhibited moderate sensitivity despite being an undifferentiated subtype cell line. Direct inhibition of GPX4 by treatment with RSL3 also resulted in similar patterns of drug sensitivity across subtypes, supporting a common ferroptosis mechanism (FIG. 12B). In contrast, treatment with piperlongumine, a ROS inducing drug that triggers apoptosis (Raj et al., 2011), does not show any differentiation stage-associated trend (FIG. 12C).

Figure 5:
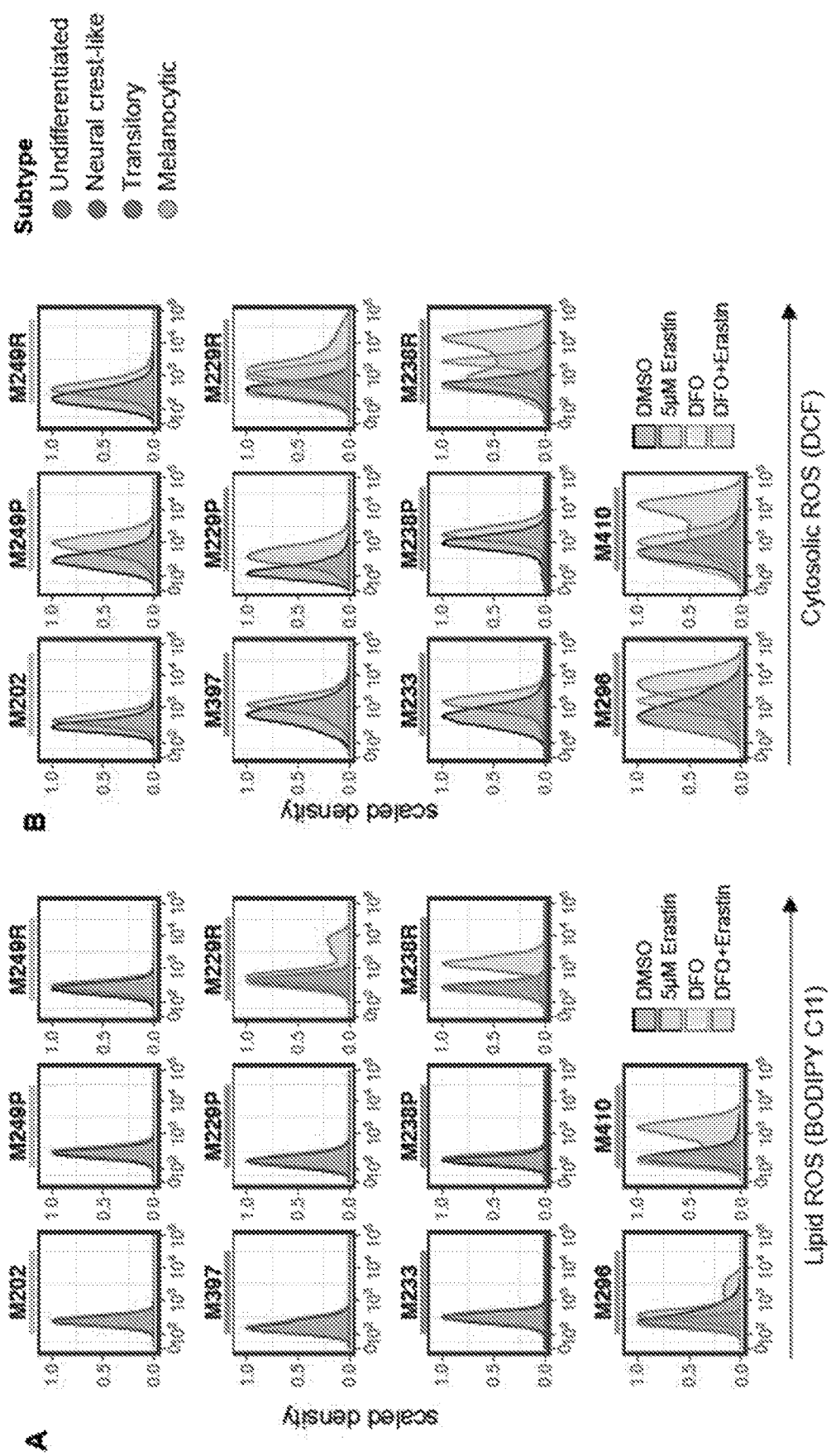
FIG. 5—Erastin treatment induces of lipid and cytosolic ROS in sensitive cell lines. (A-B) ROS measurements after 10 hr erastin treatment across cell lines by flow cytometry using BODIPY-C11 probe to measure lipid ROS (A) and CM-H2DCFDA probe to measure cytosolic ROS (B). Undifferentiated cell lines include M229R, M296, and M410; Neural Crest-like cell lines include M233, M238P, and M238R; Transitory cell lines include M397 and M229P; Melanocytic cell lines include M202, M249P, and M249R. (C-D) Relative amounts of reduced glutathione GSH (C) and oxidized GSSG (D) after 8 hr erastin treatment compared to untreated parental control for the indicated isogenic cell lines. (P: Erastin-insensitive parental cell lines; R: erastin-sensitive BRAFi-resistant cell lines.) Data shown in barplots represent mean±sem of three replicates. In C and D, each bar above P or R represents data from the DMSO control (left bar) and 5 µM Erastin (right bar)
Figure 5:
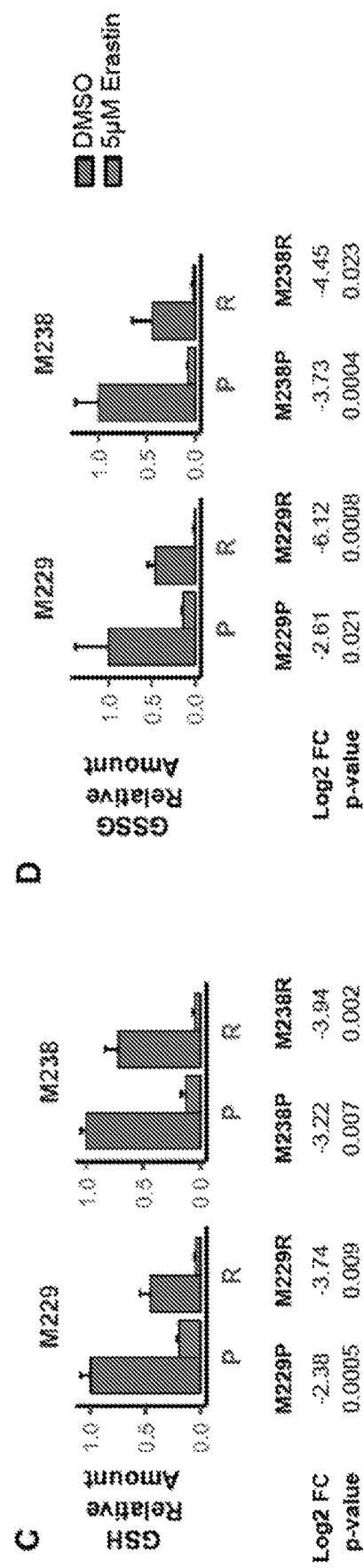

The inventors next sought to confirm if the mechanism of cell death by erastin treatment in melanoma is through ferroptosis. Cell death induced by erastin treatment in the undifferentiated signature cell lines M296, M410 M229R, and M238R, occurred rapidly in about 12 hours (FIG. 12D). The decrease in cell viability could be almost completely rescued either by iron chelation using deferoxamine (DFO) or by the lipophilic antioxidant Trolox (FIG. 4D, FIG. 12D), demonstrating that cell death is both iron and ROS dependent respectively. This mechanism of cell death is distinct from apoptosis, as treatment with the pan-caspase inhibitor Z-VAD-FMK could not rescue death induced by erastin treatment, but could rescue apoptosis induced by staurosporine as a positive control (FIG. 12E). Furthermore, the inventors observed a high induction of lipid ROS at a time preceding cell death (10 hr) for these erastin sensitive cell lines, which was not present in the other non-sensitive lines tested (FIG. 5A, FIG. 12F). This increase in lipid ROS could be rescued by DFO treatment, all together indicating that the mechanism of cell death occurs through the iron dependent accumulation of lipid ROS that is characteristic of ferroptosis. Cytosolic ROS was also elevated at this time-point in all cell lines after treatment, but at substantially higher levels in the undifferentiated signature cell lines. This increase in cytosolic ROS is also iron-dependent as this increase can be reduced by DFO treatment (FIG. 5B, FIG. 12G). To test if the differences in ROS could be a result of the inability of erastin to deplete glutathione in the less sensitive cells, the inventors measured the levels of glutathione by mass spectrometry in isogenic sub-lines M229P and M229R, and M238P and M238R. Erastin treatment significantly depleted both reduced (GSH) and oxidized glutathione (GSSG) across all the cell lines (FIG. 5C-D). However, M229R and M238R had lower basal levels and also exhibited a greater fold change decrease with treatment compared to their respective parental lines in both GSH and GSSG, which could account for the differences in sensitivity.

Figure 6:
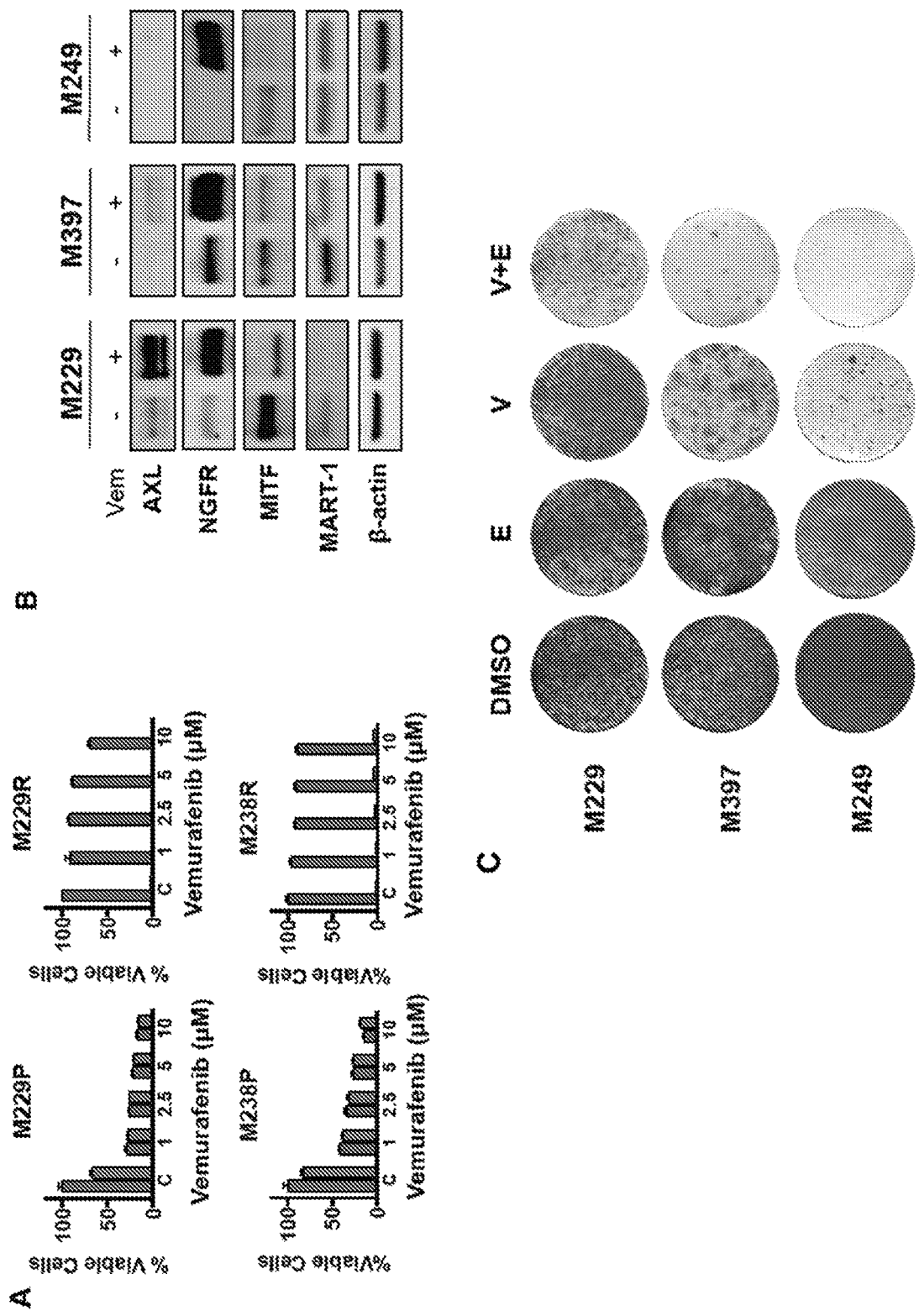
FIG. 6—Reduction in persistent melanoma cells upon combination treatment with vemurafenib and erastin. (A) Measurement of percent viable cells compared to vehicle control (DMSO) of erastin treatment combined with increasing concentration of BRAFi vemurafenib for 72 hours. Data shown in barplots represent mean±sem of three replicates. (B) Increases in the AXL and NGFR biomarkers, and decreases in the MITF and MART-1 biomarkers (immunoblot) confirming dedifferentiation of cell lines treated with long-term (21 days) vemurafenib treatment. (C) Crystal violet staining assays of long-term combination treatment of erastin (E=1 µM for M229/M397, 5 µM for M249) and vemurafenib (V=1 µM) for 16 days (M229), 24 days (M397), or 21 days (M249). DMSO treated cells were stained when confluent (7 days). Data shown is representative of three independent experiments.

5. Combination Treatment with Erastin to Target De-differentiation Associated Resistance to BRAF Inhibition Erastin and other ferroptosis inducing drugs were initially discovered from a RAS synthetic lethal screen and studies have shown a dependence on MAPK signaling for ferroptosis in some contexts (Dolma et al., 2003; Yang and Stockwell, 2008; Yagoda et al., 2007). Therefore, to evaluate the feasibility of combination treatment to overcome BRAF inhibitor resistance, the inventors first confirmed that the presence of vemurafenib does not reduce the high lethality observed with erastin treatment in dedifferentiated, vemurafenib-resistant cell lines. As expected, vemurafenib treatment alone was effective in reducing the viability of parental cell lines M229P and M238P, but had little effect on vemurafenib-resistant lines M229R and M238R. On the other hand, treatment with erastin in the dedifferentiated M229R and M238R lines resulted in a substantial loss of viable cells that was not attenuated even in the presence of high concentrations of vemurafenib (FIG. 6A). This result confirms no drug antagonism between BRAF inhibition and erastin in these dedifferentiated melanoma cells.

Considering that erastin and BRAF inhibitors target melanoma cells in different differentiation stages, and dedifferentiation is an adaptive response to BRAFi, the inventors sought to directly test their efficacy against BRAF mutant melanomas in a co-treatment strategy. The inventors thus evaluated the effects of combination treatment on three melanoma cell lines that are initially BRAFi sensitive but typically show eventual resistance due to dedifferentiation. Biomarker evaluation of the vemurafenib alone-treated cell lines confirmed their inhibitor-induced dedifferentiation with long-term treatment (FIG. 6B). Notably, inclusion of erastin or RSL3 with vemurafenib in the treatment protocol resulted in a substantial decrease in long-term persisting cells (16-24 days), supporting this dual targeting therapeutic approach (FIG. 6C and FIG. 13C-E).

In concordance with a diverse spectrum of resistance mechanisms, there are diverse responses to therapy in tumor biopsy expression profiles of patients with disease progression on either single or double drug therapy (Hugo et al., 2015). This diversity in therapy response has been reported previously in tumors, where different resistance mechanisms were found within the same patient and even within the same lesion (Allen et al., 2014; Shi et al., 2014). In the Hugo et al. data set, we identified 6 patients out of 28 profiled that had at least one disease progression tumor with moderate de-differentiation direction (negative) changes in trajectory position score (data not shown). In these de-differentiation cases, all were independently identified to have MITF downregulation or PDGFRβ upregulation by transcription or by methylation mechanisms (Hugo et al., 2015). In the twelve other patients profiled, no considerable differentiation related changes were observed (data not shown), consistent with the involvement of differentiation-independent, MAPK-reactivation resistance mechanisms.

While upon melanoma disease progression there are diverse responses in differentiation state, data from biopsies of patients early in the treatment cycle (1-3 weeks) on BRAFi therapy (vemurafenib or dabrafenib) or BRAFi plus MEKi therapy (BRAFi+trametinib) (Kwong et al., 2015) show a more consistent trend towards de-differentiation. The majority of on-treatment tumors exhibit varying degrees of de-differentiation direction (negative) changes in their trajectory position scores (FIG. 81D). In one of these patients (MDA-Pt16), biopsy data exists to again demonstrate that later disease progression can result in even greater changes in de-differentiation. These profile changes support that de-differentiation is a common early adaptive response to therapy (Fallahi-Sichani et al., 2017; Titz et al., 2016), and that acquired resistance upon disease progression is ultimately maintained by a spectrum of mechanisms that includes de-differentiation.

Figure 7:
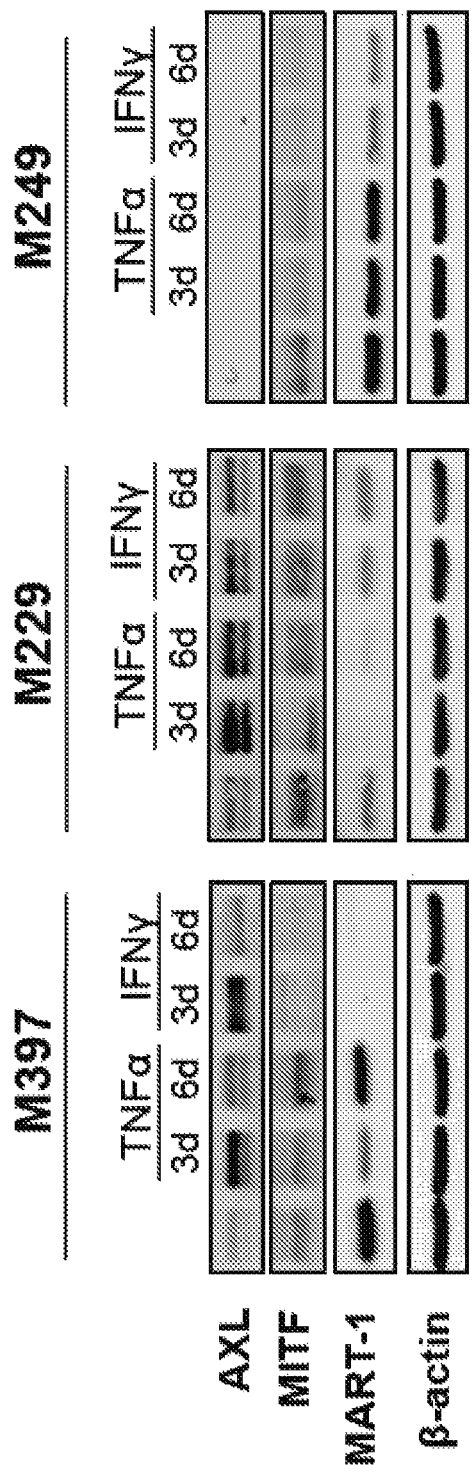
FIG. 7—Reduction in persistent melanoma cells upon treatment with erastin under inflammatory cytokine stimulation. (A) Immunoblot showing increases in the AXL biomarker, and decreases in the MITF and MART-1 biomarkers confirming dedifferentiation of cell lines treated with the indicated cytokines. (B) Crystal violet staining assays of erastin treatment for 7 days with cytokine exposure for the initial 3 days (M229 and M249) or 7 days (M397). IFNγ=100 U/mL, TNFα=1000 U/mL. Data shown is representative of three independent experiments.
Figure 7:
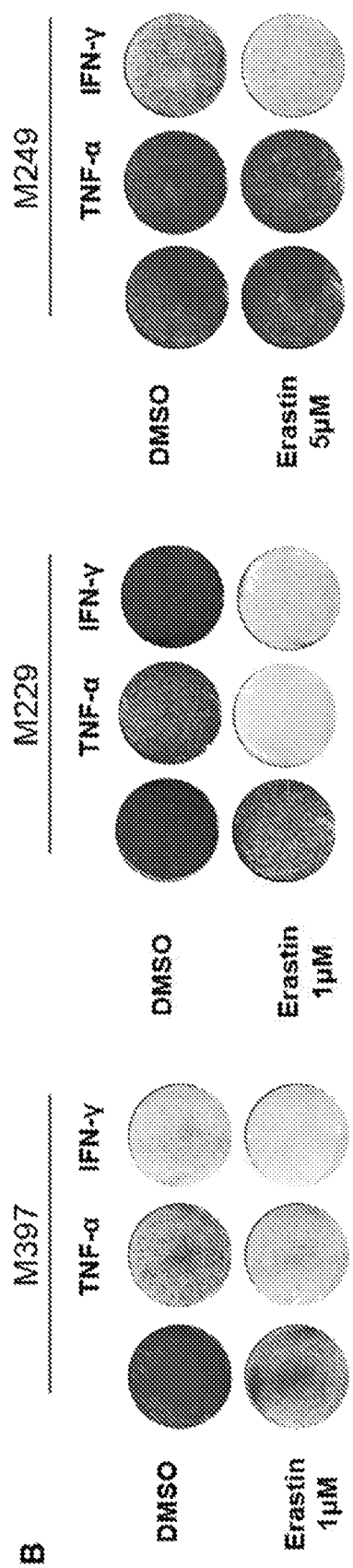

6. Combination Treatment with Erastin to Target De-differentiation Associated with Immunotherapy The dedifferentiation response of melanoma cells by pro-inflammatory signaling can be replicated in vitro in cell lines by treatment with cytokines secreted by T cells such as TNFα and IFNγ (Landsberg et al., 2012; Natarajan et al., 2014; Riesenberg et al., 2015). Therefore, the inventors sought to test if cytokine-induced de-differentiation would cause melanoma cells to become more sensitive to erastin treatment. The inventors confirmed that TNFα and IFNγ induced de-differentiation, as determined by up-regulation of AXL and decreased levels of MITF or its target gene MART-1 (FIG. 7A). The degree of dedifferentiation was cell specific and more prominent in cell lines M229 and M397. Consistent with the de-differentiation response, clonogenic assays revealed that treatment with erastin or RSL3 in the presence of these cytokines resulted in increased cell death compared to cytokine-only or untreated cells (FIG. 7B and FIG. 13H-J). In a cell line with only modest biomarker-based dedifferentiation upon IFNγ cytokine treatment (M249), the inventors still observed increased sensitivity under higher doses of ferroptosis-inducing drugs (5 μM erastin, 500 nM RSL3). In these experiments, the combined treatment contributed substantially and in some cases in a synthetic lethal fashion to reducing any persisting population. Further relevance for such a dual-targeting approach comes from the observation that melanoma cells can up-regulate surface expression of the PD-L1 ligand in response to IFNγ to suppress T cell function through activation of inhibitory PD1 receptor signaling (Iwai et al., 2002; Taube et al., 2012). Therefore, reducing this de-differentiated persisting population of cells via their sensitivity to erastin treatment can potentially boost overall antitumor immunity by preventing an accumulation of melanoma cells with immunosuppressive capabilities.

B. Discussion

Multiple studies have shown that melanoma cell lines and tumors can consistently be categorized into two phenotypes with divergent transcriptional profiles related to differentiation. The results of this example expand these two phenotypes into four subtypes that reflect distinct and progressive differentiation states found across multiple independent datasets in both cell lines and tumors. Using an independently trained classifier, subtypes were identified that consistently demonstrated inter-subtype relationships that follow our proposed differentiation progression. Further supportive of this differentiation trajectory is the observation that melanoma cells can de-differentiate progressively through these subtype signatures with elapsed time under BRAF inhibitor treatment and accompanying acquisition of BRAFi resistance.

This refined differentiation framework enabled evaluation of the melanoma subtypes in terms of their drug sensitivity profiles for hundreds of compounds within pharmacogenomics datasets. These findings revealed a previously unreported association of sensitivity to ferroptosis induction with the degree of dedifferentiation, where the undifferentiated subtype was the most sensitive and the melanocytic subtype was the most resistant. This sensitivity has therapeutic implications, and these experiments support the efficacy of ferroptosis inducing drugs in targeting both innate resistance, and acquired dedifferentiation-associated resistance induced by kinase therapies and by immunotherapy-associated cytokines. Therefore, combination therapies that include ferroptosis inducing drugs have the potential to enhance current treatment options for melanoma patients by providing a synthetic lethal approach to kill the persistent melanoma cell populations. Dedifferentiation-based adaption can be seen in patient biopsies in a little as 1 to 3 weeks (Kwong et al., 2015). This early adaptation timeframe argues for upfront co-treatment, which has generally been found more efficient than sequential therapy (Eroglu and Ribas, 2016) and prevents cells resistant to one of the therapies from accumulating additional genomic alterations such as NRAS mutations or BRAF amplifications that would make them more difficult to treat.

Melanocytes have vital antioxidant stresses and defenses inherent to their biology, owing to the high oxidative stress from melanin biosynthetic processes and UV radiation (Denat et al., 2014). Thus, it is conceivable that the loss of differentiation programs that combat redox stresses could render redox-challenged cancer cells susceptible to oxidative stress. High MITF cells were found to be more resistant to H2O2-induced cell death through MITF transcriptional upregulation of the redox sensor APE-1 (Liu et al., 2009). MITF has also been shown to drive the expression of PGC1α, a key transcription factor regulating mitochondria biogenesis and expression of ROS detoxifying enzymes (Vazquez et al., 2013). Notably, in the pharmacogenomics dataset the inventors studied and in our confirmation experiments, sensitivity to drug-induced lipid redox stress was more distinct between differentiation states, than was sensitivity to other categories of drug-induced redox stress.

Interestingly, levels of GSH and GSSG were greatly depleted by erastin in both ferroptosis-sensitive and -resistant isogenic melanoma cell lines. This is intriguing because in the ferroptosis insensitive lines, despite a considerable depletion of GSH, there was no detectable level of lipid ROS and only a moderate increase in cytosolic ROS. Thus, it is possible that the insensitive lines do not generate high levels of ROS. Differential levels of cellular iron, the activity of the iron-dependent ROS producing enzymes such as lipoxygenases, and the availability of oxidizable polyunsaturated fatty acids in the lipid membrane could all contribute to the production of lipid ROS (Dixon et al., 2012; Xie et al., 2016; Yang et al., 2016). Alternatively, erastin insensitive cells may have an increased capacity to regenerate GSH as a response to decreased de novo synthesis. GSH is regenerated from GSSG by the enzyme glutathione reductase (GSR), which requires NADPH. Engagement of metabolic pathways that generate NADPH can therefore promote the regeneration of GSH and the capacity of cells to maintain low ROS levels (Gorrini et al., 2013). Accordingly, low basal levels of NADPH were found to be predictive of sensitivity to ferroptosis across multiple cancer cell lines (Shimada et al., 2016).

Recently, it was shown that metastasizing melanoma cells experienced high levels of oxidative stress and successful metastasis is dependent on metabolic adaptations that increase GSH regeneration (Piskounova et al., 2015). This adaptation was also found to be dependent on NADPH generating enzymes, most notably of the folate pathway. Taken together with the inventors' results, this suggests that metastasizing cells would also be predicted to be more sensitive to ferroptosis due to lower levels of NADPH and GSH from oxidative stress. Thus, treatment with ferroptosis inducing drugs may potentially limit metastasis.

In summary, the refined framework of multi-stage melanoma differentiation subtypes guided the discovery of a rational therapeutic strategy to target the plasticity of melanoma cells associated with resistance. Dedifferentiation is a recurrent innate and acquired resistance mechanism to modern kinase targeted therapies and immunotherapies in the clinic. Thus, ferroptosis inducing drugs and other dedifferentiation-specific cell death inducing drugs offer a new co-treatment component, targeted directly at the dedifferentiation-based resistance escape route that limits the efficacy of current lines of melanoma therapy.

C. Methods

1. Cell Lines, Reagents, Cell Culture and Cell Treatment

Human melanoma cell lines of the M series were established from patient's biopsies under UCLA IRB approval #11-003254 as previously described (Søndergaard et al., 2010). Cells were cultured in RPMI 1640 with L-glutamine, 10% fetal bovine serum, and 1% penicillin, streptomycin and fungizone in a water-saturated incubator at 37° C. with 5% CO2. Cells were maintained and tested for *mycoplasma*, and regularly authenticated to their early passages using GenePrint® 10 System (Promega). Presence of mutations in the genes of interest were checked by OncoMap 3 or Iontrone, and was confirmed by PCR and Sanger sequencing as previously described (Wong et al., 2014). Vemurafenib (PLX 4032), erastin, Z-VAD-FMK, R428 and piperlongumine were all purchased from Selleck Chemicals. Deferoxamine was obtained from Sigma-Aldrich. Staurosporine was obtained from Cayman Chemicals. Trolox was obtained from Acros Organics. Recombinant TNFα and IFNγ were both obtained from Peprotech. For the BRAFi timecourse study, M229 was treated with vemurafenib or DMSO for the indicated timepoints at twice the 50% inhibition concentration (500 nM). For the crystal violet assays, cells for seeded at low density in 6-well plates. The next day media was replaced by drug media and replenished every 2-3 days. Plates were stained with crystal violet solution (1% crystal violet, 10% methanol). Control wells were grown for 1 week and stained when 100% confluent.

2. Transcriptional Profiling by RNA Sequencing

RNA extraction was performed using AllPrep DNA/RNA Mini kit from Qiagen in 53 human melanoma cell lines. Libraries were prepared using the Illumina TruSeq RNA sample preparation kit per the manufacturer's instructions. RNA sequencing was performed using 50 bp paired end sequencing on the Illumina HiSeq 2000 platform. Paired end 50 bp reads generated from the melanoma cell line RNA sequencing were mapped using HISAT2 to the *Homo sapiens* hg38 genome build and raw counts per quantified using HTSeq. Data is deposited in the Gene Expression Omnibus (GEO) database under accession number GSE80829. TCGA skin cutaneous melanoma (SKCM) bulk tumor raw expected counts were downloaded from the TCGA data portal (https://tcga-data.nci.nih.gov). Both the 53 melanoma cell line panel and TCGA raw expected counts were analyzed similarly to reduce technical variability from data processing. Cell line and TCGA raw counts were normalized to FPKM values using conditional quantile normalization (CQN) to adjust for gene length and GC content (Hansen et al., 2012). FPKM values were next transformed in log 2 space with an offset of 1. For the vemurafenib treated samples, RNASeq was performed using 50 bp single end sequencing and mapped the *Homo sapiens* NCBI build 37.2 reference genome using TopHat2 v2.0.9 (Kim et al., 2013) and normalized to fragments per kilobase of exon per million fragments mapped (FPKM) using Cufflinks v2.2.1 and the geometric library size normalization method (Trapnell et al., 2012). FPKM values for single and double drug MAPKi resistant cell lines from Hugo et al were obtained from GSE65186. RSEM expression values of patient tumor samples at baseline and on MAPKi treatment from Kwong et al were obtained from European Genome-phenome Archive (EGA S00001000992).

3. Microarray Transcriptional Profiling Datasets

Dataset from Hoek et al of melanoma cell lines was obtained from GSE4845 and batch normalized using ComBat from the R sva package. Dataset from Mica et al for the melanocyte differentiation stage analysis was obtained from GSE45227. Gene expression profiles from samples representing the growth conditions for each specified stage of differentiation based on the original manuscript was used for analysis (day 0 embryonic stem cell, day 6 neural crest cell, day 11 melanoblast, and day 25 melanocyte). Primary melanocyte expression profiles (adult and neonatal) were used as control. Cell line expression profiles from the CCLE and GSDC databases were downloaded from the respective resource websites (http://www.broadinstitute.org/ccle; http://www.cancerrxgene.org/downloads). For each dataset, microarray probes were collapsed to gene symbol to the maximum average probe. To have a gene list compatible for all datasets used, the inventors took an intersection of genes from both RNASeq and microarray chip platforms, resulting in 10,545 genes.

For the data from Landsberg et al, expression profiles were obtained from GSE40213. Mouse genes were mapped to human homologs using the NCBI HomoloGene database. To account for any genes that might not vary in a mouse and could dilute signal when switching to human analysis, a variance filter of 0.3 was applied.

4. Methylation Analysis

Human tumor methylation 450K array data was obtained from The Cancer Genome Atlas. Cell line methylation 450K array data was obtained from GSE68379. Probes excluded from the downstream analysis were probes with poor detection quality, probes mapping to sex chromosomes, probes with known SNPs at the CG site, and 29,233 probes previously shown to be cross-reactive with genes on sex chromosomes (Chen et al., 2013). Using the UCSC gene annotation, probes mapping to the promoter (TSS1500, TSS200, 5'UTR, and 1stExon) were collapsed to gene level by averaging the sites mapping to each gene. Probes mapping to CG islands and probes mapping to multiple genes were excluded, resulting in gene-level promoter methylation values for 15,580 genes for the cell line data and 14,318 genes for the TCGA data.

5. Classification of Cell Lines and Tumors

The top 3000 genes with the highest variance were used for clustering. Consensus complete linkage hierarchical clustering was performed using the Euclidean distance metric and subsampling 75% of samples and genes 1000 times using the ConsensusClusterPlus R package. Pairwise cluster significance, as defined by whether each cluster originates from different Gaussian distributions, was performed using the sigclust R package. A SVM TSP-based approach as proposed by Shi et al (Shi et al., 2011) was used to train the subtype prediction model, where feature selection was performed by hypergeometric test. The top 250 genes were used to build the model. The gene expression matrix was converted into a gene pair binary matrix of relative comparisons for each pair of genes A and B whether A>B as introduced by the "top scoring pairs" method (Shi et al., 2011). For each subtype, pairs were then scored by hypergeometric test to calculate the p-value of enrichment for that subtype compared to the remaining subtypes. Gene-pairs were then filtered by having a minimum p-value of 1e-05 in at least one subtype, resulting in 1561 gene-pairs. The resulting binary matrix of each cell line with identified subtype was used to train the model using a radial basis function kernel with the R package kernlab. The model performed at 94% accuracy with leave-one-out cross validation. Gene expression profiles for all datasets for prediction were similarly converted to binary matrices and used as test set for this SVM-based prediction approach.

6. Enrichment Analysis, Subtype Signatures, and Differentiation Trajectory Position Scores For subtype comparisons, signal-to-noise ratio of one subtype vs. the remaining three were used to create ranklists. Rank-based enrichment analysis was performed using Gene Set Enrichment Analysis (GSEA) (Subramanian et al., 2005) using the MSigDB C5 GO biological process gene sets. Differential expression analysis used for generating subtype signatures was performed using Significance Analysis of Microarrays at a 5% false discovery rate (FDR) using the same package in R. For subtype signature scores, z-scores for of all member genes were summed and divided by the number of member genes. To avoid potential confounding issues with gene expression from non-tumor sources, genes correlated with the immune and keratin signature were not included. Differentiation trajectory position score was determined using a center of mass approach where all single subtype and transitional-paired subtype average signature scores were summed in a weighted fashion. Weighting represented the relative position along the differentiation trajectory (i) running from 1 to 7 for undifferentiated, undifferentiated-neural crest like pair, neural crest like, neural crest like-transitory pair, transitory, transitory-melanocytic pair, and melanocytic. The formula is given by:

$$\text{Differentiation Trajectory Position} = \frac{\sum_{i=1}^{7} m_i \cdot i}{\sum_{i=1}^{7} m_i}$$

where $m_i$ are the seven signature scores.

7. Statistical Analysis

Principal component analysis (PCA) was performed on mean centered data and all statistical analyses were performed in R (http://www.R-project.org/). Projections were calculated by matrix multiplication of the centered data to be projected using the rotation matrix determined from the PCA of the original source data. ANOVA p-values were determined using the non-parametric Kruskal-Wallis test at a significance threshold of 0.05. Reported p-values between pairs of subtypes were determined using Dunn post-hoc testing with multiple hypothesis correction using the Benjamini & Hochberg method. Heatmaps and figures were generated using pheatmap and ggplot2 R packages.

8. Immune and Keratin Confounding Signature Criteria

A starter list of immune genes was obtained from the Immunome database, downloaded from InnateDB (http://www.innatedb.com). PCA was used to reduce dimensionality of the list of immune genes to a single immune score (PC1). The total list of immune confounded genes was determined by identifying genes that were correlated to the immune score above a threshold value. The threshold correlation was determined using an ROC analysis, comparing distributions of correlations of genes within the immune starter list vs. all others. Keratin confounded genes was identified similarly, using genes annotated as keratins from the NCBI gene database (http://www.ncbi.nlm.nih.gov/gene/) as the starter list of genes.

9. Analysis of Reactive Oxygen Species Production

In 12-well plates, 100,000 cells per well were seeded and allowed to attach for approximately 12 hours. Cells were then treated with media containing 5 μM of erastin, 100 μM deferoxamine or a combination of both, and returned to the 37° C. tissue culture incubator. After 10 hours, drug media was replaced by media containing DMSO control, 5 μM of CM-H2DCFDA dye (Life Technologies, C6827), or 5 μM of C11-BODIPY (Life Technologies, D3861) and incubated for another 20 min at 37° C. Cells were then washed with PBS, harvested by trypsinization, followed by another wash with PBS. Cells were resuspended in 400 μL PBS, strained through a 35 μm nylon mesh filter, and analyzed by flow cytometry using BD LSRII equipped with 488 nm laser for excitation (BD Biosciences).

10. Viability Measurements

All cell viability assays were assayed in 96-well format with 5000 cells seeded per well. Dose-response curves were assayed using CellTiter-Glo luminescent cell viability assay (Promega, G7572). For all other measurements of viable cells, a fluorescent resazurin-based (Sigma-Aldrich, R7017) assay (AlamarBlue) was used with fluorescence measured at 570/600 ex/em wavelength. Percentage cell viability is reported as a percentage relative to the negative control treatment. Measurement of dead cells per time was measured by incubating treated cells with the IncuCyte Cytotox Red Reagent and imaging with IncuCyte ZOOM Live-Cell Imaging System (Essen BioScience). Trypan blue exclusion was also used for cell death assays.

11. Mass Spectrometry-Based Metabolomic Analyses

In 6-well plates, 200,000 cells per seeded per well and allowed to attach over night. The next day, media was replaced with media containing 5 μM of erastin. After 8 hr of treatment, cells were washed with ice-cold 150 mM ammonium acetate (NH4AcO) pH 7.3 and metabolites extracted in 1 ml ice-cold 80% MeOH. The cells were quickly transferred into a microfuge tube, and 10 nmol norvaline was added to the cell suspension for use as an internal standard. The suspension was subsequently vortexed three times over 15 min and then spun down at 4° C. for 5 min. The supernatant was transferred into a glass vial, the cell pellet was re-extracted with 200 μl ice-cold 80% MeOH and spun down and the supernatants were combined. Metabolites were dried at 30° C. under vacuum and resuspended in 50 μl of 70% acetonitrile (ACN).

Samples were run on a Q-Exactive mass spectrometer coupled to an UltiMate 3000RSLC UHPLC system (Thermo Scientific). The mass spectrometer was run in polarity switching mode (+3.00 kV/−2.25 kV) with an m/z window ranging from 65 to 975. Mobile phase A was 5 mM NH4AcO, pH 9.9, and mobile phase B was ACN. Metabolites were separated on a Luna 3 μm NH2 100 Å (150×2.0 mm) (Phenomenex) column. The flow was kept at 200 μl/min, and the gradient was from 15% A to 95% A in 18 min, followed by an isocratic step for 9 min and re-equilibration for 7 min. Metabolites were detected and quantified as area under the curve (AUC) based on retention time and accurate mass (<3 ppm) using the TraceFinder 3.1 (Thermo Scientific) software. Samples were normalized by protein concentration measured using the BCA Protein Assay Kit from Pierce Biotechnology. All samples were run as biological triplicates, and consistent results were seen in independent experiments.

12. Immunoblotting

Cells were lysed in modified RIPA buffer (50 mM Tris-HCl (pH 7.5), 150 NaCl, 10 mM β-glycerophosphate, 1% NP-40, 0.25% sodium deoxycholate, 10 mM sodium pyrophosphate, 30 mM sodium fluoride, 1 mM EDTA, 1 mM vanadate, 20 μg/ml aprotinin, 20 μg/ml leupeptin, and 1 mM phenylmethylsulfonyl fluoride). Whole-cell lysates were resolved by SDS-PAGE on TruPAGE 4-15% gradient gels (Sigma-Aldrich) and blotted onto nitrocellulose membranes. Membranes were blocked overnight with 5% milk and then incubated sequentially with primary and then IRDye-conjugated secondary antibodies (Li-Cor). Blots were imaged using the Odyssey Infrared Imaging System (Li-Cor). Primary antibodies used for Western blot analysis were MITF (DGG7V, CST), MART-1 (A103, SCBT), and AXL (C89E7, CST).

TABLE S1

Melanoma Cell Line Annotations

| Cell Line | Mutation Status | Subtype |
|---|---|---|
| M407 | BRAF mutant | Undifferentiated |
| M410 | BRAF mutant | Undifferentiated |
| M257 | Wild-type | Undifferentiated |
| M244 | NRAS mutant | Undifferentiated |
| M296 | NRAS mutant | Undifferentiated |
| M318 | NRAS mutant | Undifferentiated |
| M381 | BRAF mutant | Undifferentiated |
| M406 | BRAF mutant | Undifferentiated |
| M229AR | BRAF mutant | Undifferentiated |
| Sbcl2 | NRAS mutant | Undifferentiated |
| M233 | BRAF mutant | Neural crest like |
| M243 | NRAS mutant | Neural crest like |
| M245 | NRAS mutant | Neural crest like |
| M238 | BRAF mutant | Neural crest like |
| M370 | BRAF mutant | Neural crest like |
| M409 | BRAF mutant | Neural crest like |
| M423 | NA | Neural crest like |
| M418 | Wild-type | Neural crest like |
| M402 | BRAF mutant | Neural crest like |
| M411 | BRAF mutant | Neural crest like |
| M238AR | BRAF mutant | Neural crest like |
| M255 | BRAF mutant | Neural crest like |
| M409AR | BRAF mutant | Neural crest like |
| M420 | BRAF mutant | Neural crest like |
| M395 | BRAF mutant | Transitory |

TABLE S1-continued

Melanoma Cell Line Annotations

| Cell Line | Mutation Status | Subtype |
|---|---|---|
| M308 | BRAF mutant | Transitory |
| M229 | BRAF mutant | Transitory |
| M263 | BRAF mutant | Transitory |
| M297 | BRAF mutant | Transitory |
| M376 | BRAF/NRAS double mutant | Transitory |
| M398 | BRAF/NRAS double mutant | Transitory |
| M375 | Wild-type | Transitory |
| M399 | BRAF mutant | Transitory |
| M395AR | BRAF mutant | Transitory |
| M397 | BRAF mutant | Transitory |
| M397AR | BRAF mutant | Transitory |
| M202 | NRAS mutant | Melanocytic |
| M207 | NRAS mutant | Melanocytic |
| M230 | Wild-type | Melanocytic |
| M249 | BRAF mutant | Melanocytic |
| M262 | BRAF mutant | Melanocytic |
| M285 | Wild-type | Melanocytic |
| M311 | NRAS mutant | Melanocytic |
| M417 | BRAF mutant | Melanocytic |
| M416 | BRAF mutant | Melanocytic |
| M421 | BRAF mutant | Melanocytic |
| M368 | Wild-type | Melanocytic |
| M403 | BRAF mutant | Melanocytic |
| M408 | NRAS mutant | Melanocytic |
| M249AR | BRAF/NRAS double mutant | Melanocytic |
| M412a | NRAS mutant | Melanocytic |
| M412b | NRAS mutant | Melanocytic |
| PB | Wild-type | Melanocytic |

TABLE S4

Subtype Signatures, Differentially Upregulated Genes

| Gene | Signature | Description |
|---|---|---|
| AJUBA | Undifferentiated | ajuba LIM protein |
| TOR4A | Undifferentiated | torsin family 4, member A |
| MARCH4 | Undifferentiated | membrane-associated ring finger (C3HC4) 4, E3 ubiquitin protein ligase |
| ZDHHC2 | Undifferentiated | Zinc finger, DHHC-type containing 2 |
| ZNF467 | Undifferentiated | Zinc finger protein 467 |
| ZNF185 | Undifferentiated | Zinc finger protein 185 (LIM domain) |
| ZIC2 | Undifferentiated | Zic family member 2 (odd-paired homolog, *Drosophila*) |
| VASN | Undifferentiated | Vasorin |
| UCP2 | Undifferentiated | Uncoupling protein 2 (mitochondrial, proton carrier) |
| GALNT6 | Undifferentiated | UDP-N-acetyl-alpha-D-galactosamine:polypeptide N-acetylgalactosaminyltransferase 6 (GalNAc-T6) |
| TNFAIP2 | Undifferentiated | Tumor necrosis factor, alpha-induced protein 2 |
| TNFSF18 | Undifferentiated | Tumor necrosis factor (ligand) superfamily, member 18 |
| TMEM40 | Undifferentiated | Transmembrane protein 40 |
| TMEM200A | Undifferentiated | Transmembrane protein 200A |
| TMEM184A | Undifferentiated | Transmembrane protein 184A |
| TBL1X | Undifferentiated | Transducin (beta)-like 1X-linked |
| TRERF1 | Undifferentiated | Transcriptional regulating factor 1 |
| TOX | Undifferentiated | Thymocyte selection-associated high mobility group box |
| TBC1D2 | Undifferentiated | TBC1 domain family, member 2 |
| SFN | Undifferentiated | Stratifin |
| SAMD12 | Undifferentiated | Sterile alpha motif domain containing 12 |
| SAMD11 | Undifferentiated | Sterile alpha motif domain containing 11 |
| SOX9 | Undifferentiated | SRY (sex determining region Y)-box 9 |
| SLC8A1 | Undifferentiated | Solute carrier family 8 (sodium/calcium exchanger), member 1 |
| SLC38A4 | Undifferentiated | Solute carrier family 38, member 4 |
| SLC16A14 | Undifferentiated | Solute carrier family 16, member 14 (monocarboxylic acid transporter 14) |
| SCN5A | Undifferentiated | Sodium channel, voltage-gated, type V, alpha subunit |
| SCNN1A | Undifferentiated | Sodium channel, nonvoltage-gated 1 alpha |
| SH3RF2 | Undifferentiated | SH3 domain containing ring finger 2 |
| SERPINB7 | Undifferentiated | Serpin peptidase inhibitor, clade B (ovalbumin), member 7 |
| SLPI | Undifferentiated | Secretory leukocyte peptidase inhibitor |
| SECTM1 | Undifferentiated | Secreted and transmembrane 1 |
| RUNX2 | Undifferentiated | Runt-related transcription factor 2 |
| ARHGAP29 | Undifferentiated | Rho GTPase activating protein 29 |
| REN | Undifferentiated | Renin |
| PAWR | Undifferentiated | PRKC, apoptosis, WT1, regulator |
| PSG9 | Undifferentiated | Pregnancy specific beta-1-glycoprotein 9 |
| PSG5 | Undifferentiated | Pregnancy specific beta-1-glycoprotein 5 |
| PSG4 | Undifferentiated | Pregnancy specific beta-1-glycoprotein 4 |
| PBX1 | Undifferentiated | Pre-B-cell leukemia homeobox 1 |

TABLE S4-continued

Subtype Signatures, Differentially Upregulated Genes

| Gene | Signature | Description |
| --- | --- | --- |
| PLAGL1 | Undifferentiated | Pleiomorphic adenoma gene-like 1 |
| PHLDB2 | Undifferentiated | Pleckstrin homology-like domain, family B, member 2 |
| PLEKHA6 | Undifferentiated | Pleckstrin homology domain containing, family A member 6 |
| PDGFC | Undifferentiated | Platelet derived growth factor C |
| PLAU | Undifferentiated | Plasminogen activator, urokinase |
| PKP2 | Undifferentiated | Plakophilin 2 |
| PLAC8 | Undifferentiated | Placenta-specific 8 |
| PADI3 | Undifferentiated | Peptidyl arginine deiminase, type III |
| PITX1 | Undifferentiated | Paired-like homeodomain 1 |
| NUAK1 | Undifferentiated | NUAK family, SNF1-like kinase, 1 |
| NTNG1 | Undifferentiated | Netrin G1 |
| NMT2 | Undifferentiated | N-myristoyltransferase 2 |
| MYEOV | Undifferentiated | Myeloma overexpressed (in a subset of t(11; 14) positive multiple myelomas) |
| MICAL2 | Undifferentiated | Microtubule associated monoxygenase, calponin and LIM domain containing 2 |
| MGST1 | Undifferentiated | Microsomal glutathione S-transferase 1 |
| MECOM | Undifferentiated | MDS1 and EVI1 complex locus |
| LYPD6B | Undifferentiated | LY6/PLAUR domain containing 6B |
| LAMA5 | Undifferentiated | Laminin, alpha 5 |
| KISS1 | Undifferentiated | KiSS-1 metastasis-suppressor |
| KRT86 | Undifferentiated | Keratin 86 |
| KRT81 | Undifferentiated | Keratin 81 |
| KRT80 | Undifferentiated | Keratin 80 |
| KRT8 | Undifferentiated | Keratin 8 |
| KRT7 | Undifferentiated | Keratin 7 |
| KRT18 | Undifferentiated | Keratin 18 |
| JUP | Undifferentiated | Junction plakoglobin |
| IL7R | Undifferentiated | Interleukin 7 receptor |
| IL4R | Undifferentiated | Interleukin 4 receptor |
| IRS1 | Undifferentiated | Insulin receptor substrate 1 |
| IGFN1 | Undifferentiated | Immunoglobulin-like and fibronectin type III domain containing 1 |
| HES7 | Undifferentiated | Hairy and enhancer of split 7 (*Drosophila*) |
| GDA | Undifferentiated | Guanine deaminase |
| GLIS2 | Undifferentiated | GLIS family zinc finger 2 |
| GATA2 | Undifferentiated | GATA binding protein 2 |
| GPRC5C | Undifferentiated | G protein-coupled receptor, family C, group 5, member C |
| GPRC5A | Undifferentiated | G protein-coupled receptor, family C, group 5, member A |
| FMNL1 | Undifferentiated | Formin-like 1 |
| FOXA1 | Undifferentiated | Forkhead box A1 |
| FLNC | Undifferentiated | Filamin C, gamma |
| FERMT1 | Undifferentiated | Fermitin family member 1 |
| FAT4 | Undifferentiated | FAT tumor suppressor homolog 4 (*Drosophila*) |
| FAM196B | Undifferentiated | Family with sequence similarity 196, member B |
| ELFN2 | Undifferentiated | Extracellular leucine-rich repeat and fibronectin type III domain containing 2 |
| EGFR | Undifferentiated | Epidermal growth factor receptor |
| DSE | Undifferentiated | Dermatan sulfate epimerase |
| DMBT1 | Undifferentiated | Deleted in malignant brain tumors 1 |
| DIO2 | Undifferentiated | Deiodinase, iodothyronine, type II |
| DOCK2 | Undifferentiated | Dedicator of cytokinesis 2 |
| CYP2S1 | Undifferentiated | Cytochrome P450, family 2, subfamily S, polypeptide 1 |
| CRIM1 | Undifferentiated | Cysteine rich transmembrane BMP regulator 1 (chordin-like) |
| CDK15 | Undifferentiated | Cyclin-dependent kinase 15 |
| CORO6 | Undifferentiated | Coronin 6 |
| COLEC10 | Undifferentiated | Collectin sub-family member 10 (C-type lectin) |
| CCDC88C | Undifferentiated | Coiled-coil domain containing 88C |
| CCDC69 | Undifferentiated | Coiled-coil domain containing 69 |
| F3 | Undifferentiated | Coagulation factor III (thromboplastin, tissue factor) |
| F2RL1 | Undifferentiated | Coagulation factor II (thrombin) receptor-like 1 |
| CLU | Undifferentiated | Clusterin |
| CDYL2 | Undifferentiated | Chromodomain protein, Y-like 2 |
| CITED2 | Undifferentiated | Cbp/p300-interacting transactivator, with Glu/Asp-rich carboxy-terminal domain, 2 |

TABLE S4-continued

Subtype Signatures, Differentially Upregulated Genes

| Gene | Signature | Description |
|---|---|---|
| CARD11 | Undifferentiated | Caspase recruitment domain family, member 11 |
| CPA4 | Undifferentiated | Carboxypeptidase A4 |
| CREB3L1 | Undifferentiated | cAMP responsive element binding protein 3-like 1 |
| CNN1 | Undifferentiated | Calponin 1, basic, smooth muscle |
| CALB2 | Undifferentiated | Calbindin 2 |
| CDH4 | Undifferentiated | Cadherin 4, type 1, R-cadherin (retinal) |
| BTBD11 | Undifferentiated | BTB (POZ) domain containing 11 |
| BDNF | Undifferentiated | Brain-derived neurotrophic factor |
| BASP1 | Undifferentiated | Brain abundant, membrane attached signal protein 1 |
| BNC1 | Undifferentiated | Basonuclin 1 |
| ATP8B1 | Undifferentiated | ATPase, aminophospholipid transporter, class I, type 8B, member 1 |
| ABCG2 | Undifferentiated | ATP-binding cassette, sub-family G (WHITE), member 2 |
| ARMC4 | Undifferentiated | Armadillo repeat containing 4 |
| ANKRD1 | Undifferentiated | Ankyrin repeat domain 1 (cardiac muscle) |
| AR | Undifferentiated | Androgen receptor |
| AMIGO2 | Undifferentiated | Adhesion molecule with Ig-like domain 2 |
| ADAMTSL1 | Undifferentiated | ADAMTS-like 1 |
| ACSL5 | Undifferentiated | Acyl-CoA synthetase long-chain family member 5 |
| VIT | Undifferentiated-Neural crest-like | Vitrin |
| VIPR1 | Undifferentiated-Neural crest-like | Vasoactive intestinal peptide receptor 1 |
| VEGFC | Undifferentiated-Neural crest-like | Vascular endothelial growth factor C |
| TWIST2 | Undifferentiated-Neural crest-like | Twist homolog 2 (*Drosophila*) |
| TNFRSF12A | Undifferentiated-Neural crest-like | Tumor necrosis factor receptor superfamily, member 12A |
| TPM1 | Undifferentiated-Neural crest-like | Tropomyosin 1 (alpha) |
| TPBG | Undifferentiated-Neural crest-like | Trophoblast glycoprotein |
| TLE4 | Undifferentiated-Neural crest-like | Transducin-like enhancer of split 4 (E(sp1) homolog, *Drosophila*) |
| TOX2 | Undifferentiated-Neural crest-like | TOX high mobility group box family member 2 |
| TLR4 | Undifferentiated-Neural crest-like | Toll-like receptor 4 |
| THSD4 | Undifferentiated-Neural crest-like | Thrombospondin, type I, domain containing 4 |
| STX1A | Undifferentiated-Neural crest-like | Syntaxin 1A (brain) |
| SYT1 | Undifferentiated-Neural crest-like | Synaptotagmin I |
| SYNPO | Undifferentiated-Neural crest-like | Synaptopodin |
| STRA6 | Undifferentiated-Neural crest-like | Stimulated by retinoic acid gene 6 homolog (mouse) |
| STC2 | Undifferentiated-Neural crest-like | Stanniocalcin 2 |
| SPRED3 | Undifferentiated-Neural crest-like | Sprouty-related, EVH1 domain containing 3 |
| SPOCD1 | Undifferentiated-Neural crest-like | SPOC domain containing 1 |
| SPOCK1 | Undifferentiated-Neural crest-like | Sparc/osteonectin, cwcv and kazal-like domains proteoglycan (testican) 1 |
| SLC2A1 | Undifferentiated-Neural crest-like | Solute carrier family 2 (facilitated glucose transporter), member 1 |
| SLC16A2 | Undifferentiated-Neural crest-like | Solute carrier family 16, member 2 (monocarboxylic acid transporter 8) |
| SLC14A1 | Undifferentiated-Neural crest-like | Solute carrier family 14 (urea transporter), member 1 (Kidd blood group) |
| SLC12A8 | Undifferentiated-Neural crest-like | Solute carrier family 12 (potassium/chloride transporters), member 8 |
| SMAGP | Undifferentiated-Neural crest-like | Small cell adhesion glycoprotein |
| SLIT2 | Undifferentiated-Neural crest-like | Slit homolog 2 (*Drosophila*) |
| SDK1 | Undifferentiated-Neural crest-like | Sidekick homolog 1, cell adhesion molecule (chicken) |
| STAC | Undifferentiated-Neural crest-like | SH3 and cysteine rich domain |
| SLFN11 | Undifferentiated-Neural crest-like | Schlafen family member 11 |
| S100A2 | Undifferentiated-Neural crest-like | S100 calcium binding protein A2 |
| ROBO4 | Undifferentiated-Neural crest-like | Roundabout homolog 4, magic roundabout (*Drosophila*) |
| RAB27B | Undifferentiated-Neural crest-like | RAB27B, member RAS oncogene family |
| PKIA | Undifferentiated-Neural crest-like | Protein kinase (cAMP-dependent, catalytic) inhibitor alpha |
| PRSS23 | Undifferentiated-Neural crest-like | Protease, serine, 23 |
| PAPPA | Undifferentiated-Neural crest-like | Pregnancy-associated plasma protein A, pappalysin 1 |
| PRDM1 | Undifferentiated-Neural crest-like | PR domain containing 1, with ZNF domain |
| KCNMA1 | Undifferentiated-Neural crest-like | Potassium large conductance calcium-activated channel, subfamily M, alpha member 1 |

TABLE S4-continued

Subtype Signatures, Differentially Upregulated Genes

| Gene | Signature | Description |
| --- | --- | --- |
| KCNN4 | Undifferentiated-Neural crest-like | Potassium intermediate/small conductance calcium-activated channel, subfamily N, member 4 |
| PODXL | Undifferentiated-Neural crest-like | Podocalyxin-like |
| PDGFRB | Undifferentiated-Neural crest-like | Platelet-derived growth factor receptor, beta polypeptide |
| PLAUR | Undifferentiated-Neural crest-like | Plasminogen activator, urokinase receptor |
| PXDN | Undifferentiated-Neural crest-like | Peroxidasin homolog (*Drosophila*) |
| PTX3 | Undifferentiated-Neural crest-like | Pentraxin 3, long |
| NMNAT2 | Undifferentiated-Neural crest-like | Nicotinamide nucleotide adenylyltransferase 2 |
| NRP1 | Undifferentiated-Neural crest-like | Neuropilin 1 |
| NGEF | Undifferentiated-Neural crest-like | Neuronal guanine nucleotide exchange factor |
| NEGR1 | Undifferentiated-Neural crest-like | Neuronal growth regulator 1 |
| NRG1 | Undifferentiated-Neural crest-like | Neuregulin 1 |
| NTN4 | Undifferentiated-Neural crest-like | Netrin 4 |
| MT2A | Undifferentiated-Neural crest-like | Metallothionein 2A |
| MT1E | Undifferentiated-Neural crest-like | Metallothionein 1E |
| MPP4 | Undifferentiated-Neural crest-like | Membrane protein, palmitoylated 4 (MAGUK p55 subfamily member 4) |
| LOXL2 | Undifferentiated-Neural crest-like | Lysyl oxidase-like 2 |
| LDOC1 | Undifferentiated-Neural crest-like | Leucine zipper, down-regulated in cancer 1 |
| LAMB3 | Undifferentiated-Neural crest-like | Laminin, beta 3 |
| JUN | Undifferentiated-Neural crest-like | Jun proto-oncogene |
| IL31RA | Undifferentiated-Neural crest-like | Interleukin 31 receptor A |
| IL11 | Undifferentiated-Neural crest-like | Interleukin 11 |
| IL1B | Undifferentiated-Neural crest-like | Interleukin 1, beta |
| ITGA3 | Undifferentiated-Neural crest-like | Integrin, alpha 3 (antigen CD49C, alpha 3 subunit of VLA-3 receptor) |
| ITGA2 | Undifferentiated-Neural crest-like | Integrin, alpha 2 (CD49B, alpha 2 subunit of VLA-2 receptor) |
| IGFBP6 | Undifferentiated-Neural crest-like | Insulin-like growth factor binding protein 6 |
| ID1 | Undifferentiated-Neural crest-like | Inhibitor of DNA binding 1, dominant negative helix-loop-helix protein |
| INHBA | Undifferentiated-Neural crest-like | Inhibin, beta A |
| HRH1 | Undifferentiated-Neural crest-like | Histamine receptor H1 |
| GAS6 | Undifferentiated-Neural crest-like | Growth arrest-specific 6 |
| GLIPR1 | Undifferentiated-Neural crest-like | GLI pathogenesis-related 1 |
| GFRA1 | Undifferentiated-Neural crest-like | GDNF family receptor alpha 1 |
| GATA3 | Undifferentiated-Neural crest-like | GATA binding protein 3 |
| GPR176 | Undifferentiated-Neural crest-like | G protein-coupled receptor 176 |
| FZD2 | Undifferentiated-Neural crest-like | Frizzled homolog 2 (*Drosophila*) |
| FJX1 | Undifferentiated-Neural crest-like | Four jointed box 1 (*Drosophila*) |
| FOSL1 | Undifferentiated-Neural crest-like | FOS-like antigen 1 |
| FOXF1 | Undifferentiated-Neural crest-like | Forkhead box F1 |
| FBLIM1 | Undifferentiated-Neural crest-like | Filamin binding LIM protein 1 |
| FLNB | Undifferentiated-Neural crest-like | Filamin B, beta |
| FAM83G | Undifferentiated-Neural crest-like | Family with sequence similarity 83, member G |
| FAM20C | Undifferentiated-Neural crest-like | Family with sequence similarity 20, member C |
| FAM171A1 | Undifferentiated-Neural crest-like | Family with sequence similarity 171, member A1 |
| FAM155A | Undifferentiated-Neural crest-like | Family with sequence similarity 155, member A |
| ERRFI1 | Undifferentiated-Neural crest-like | ERBB receptor feedback inhibitor 1 |
| EFNB2 | Undifferentiated-Neural crest-like | Ephrin-B2 |
| DPYD | Undifferentiated-Neural crest-like | Dihydropyrimidine dehydrogenase |
| DKK1 | Undifferentiated-Neural crest-like | Dickkopf homolog 1 (*Xenopus laevis*) |
| DOCK5 | Undifferentiated-Neural crest-like | Dedicator of cytokinesis 5 |
| CYR61 | Undifferentiated-Neural crest-like | Cysteine-rich, angiogenic inducer, 61 |
| CLMP | Undifferentiated-Neural crest-like | CXADR-like membrane protein |
| COL13A1 | Undifferentiated-Neural crest-like | Collagen, type XIII, alpha 1 |
| COL12A1 | Undifferentiated-Neural crest-like | Collagen, type XII, alpha 1 |
| COL5A1 | Undifferentiated-Neural crest-like | Collagen, type V, alpha 1 |
| F2RL2 | Undifferentiated-Neural crest-like | Coagulation factor II (thrombin) receptor-like 2 |
| C16orf45 | Undifferentiated-Neural crest-like | Chromosome 16 open reading frame 45 |
| C15orf52 | Undifferentiated-Neural crest-like | Chromosome 15 open reading frame 52 |
| C12orf75 | Undifferentiated-Neural crest-like | Chromosome 12 open reading frame 75 |
| CD163L1 | Undifferentiated-Neural crest-like | CD163 molecule-like 1 |
| CAV1 | Undifferentiated-Neural crest-like | Caveolin 1, caveolae protein, 22 kDa |
| CARD10 | Undifferentiated-Neural crest-like | Caspase recruitment domain family, member 10 |
| CLCF1 | Undifferentiated-Neural crest-like | Cardiotrophin-like cytokine factor 1 |
| CDH13 | Undifferentiated-Neural crest-like | Cadherin 13, H-cadherin (heart) |
| BMP2 | Undifferentiated-Neural crest-like | Bone morphogenetic protein 2 |

TABLE S4-continued

Subtype Signatures, Differentially Upregulated Genes

| Gene | Signature | Description |
| --- | --- | --- |
| AXL | Undifferentiated-Neural crest-like | AXL receptor tyrosine kinase |
| ABCC3 | Undifferentiated-Neural crest-like | ATP-binding cassette, sub-family C (CFTR/MRP), member 3 |
| ARNTL2 | Undifferentiated-Neural crest-like | Aryl hydrocarbon receptor nuclear translocator-like 2 |
| ANTXR2 | Undifferentiated-Neural crest-like | Anthrax toxin receptor 2 |
| ANXA1 | Undifferentiated-Neural crest-like | Annexin A1 |
| AKR1C3 | Undifferentiated-Neural crest-like | Aldo-keto reductase family 1, member C3 (3-alpha hydroxysteroid dehydrogenase, type II) |
| ARL4C | Undifferentiated-Neural crest-like | ADP-ribosylation factor-like 4C |
| PXYLP1 | Neural crest-like | 2-phosphoxylose phosphatase 1 |
| CXCL8 | Neural crest-like | C-X-C Motif Chemokine Ligand 8 |
| CEMIP | Neural crest-like | Cell Migration Inducing Hyaluronan Binding Protein |
| TCAF2 | Neural crest-like | TRPM8 Channel Associated Factor 2 |
| ZNF469 | Neural crest-like | Zinc finger protein 469 |
| WNT5A | Neural crest-like | Wingless-type MMTV integration site family, member 5A |
| TMEM47 | Neural crest-like | Transmembrane protein 47 |
| TMEM171 | Neural crest-like | Transmembrane protein 171 |
| TGFBI | Neural crest-like | Transforming growth factor, beta-induced, 68 kDa |
| TGFA | Neural crest-like | Transforming growth factor, alpha |
| TFAP2C | Neural crest-like | Transcription factor AP-2 gamma (activating enhancer binding protein 2 gamma) |
| TSPAN13 | Neural crest-like | Tetraspanin 13 |
| SQRDL | Neural crest-like | Sulfide quinone reductase-like (yeast) |
| SULF1 | Neural crest-like | Sulfatase 1 |
| ST8SIA5 | Neural crest-like | ST8 alpha-N-acetyl-neuraminide alpha-2,8-sialyltransferase 5 |
| SOX2 | Neural crest-like | SRY (sex determining region Y)-box 2 |
| SLC24A3 | Neural crest-like | Solute carrier family 24 (sodium/potassium/calcium exchanger), member 3 |
| SLITRK6 | Neural crest-like | SLIT and NTRK-like family, member 6 |
| SHISA2 | Neural crest-like | Shisa homolog 2 (*Xenopus laevis*) |
| SH3PXD2A | Neural crest-like | SH3 and PX domains 2A |
| SERTAD4 | Neural crest-like | SERTA domain containing 4 |
| STK32B | Neural crest-like | Serine/threonine kinase 32B |
| SEMA3B | Neural crest-like | Sema domain, immunoglobulin domain (Ig), short basic domain, secreted, (semaphorin) 3B |
| SFRP1 | Neural crest-like | Secreted frizzled-related protein 1 |
| S100A6 | Neural crest-like | S100 calcium binding protein A6 |
| RAMP1 | Neural crest-like | Receptor (G protein-coupled) activity modifying protein 1 |
| PMEPA1 | Neural crest-like | Prostate transmembrane protein, androgen induced 1 |
| PCSK5 | Neural crest-like | Proprotein convertase subtilisin/kexin type 5 |
| PHLDA2 | Neural crest-like | Pleckstrin homology-like domain, family A, member 2 |
| PLA2G7 | Neural crest-like | Phospholipase A2, group VII (platelet-activating factor acetylhydrolase, plasma) |
| OPRD1 | Neural crest-like | Opioid receptor, delta 1 |
| NTM | Neural crest-like | Neurotrimin |
| NRXN3 | Neural crest-like | Neurexin 3 |
| NES | Neural crest-like | Nestin |
| MUC5B | Neural crest-like | Mucin 5B, oligomeric mucus/gel-forming |
| MAP1LC3A | Neural crest-like | Microtubule-associated protein 1 light chain 3 alpha |
| LRRC15 | Neural crest-like | Leucine rich repeat containing 15 |
| KIAA1755 | Neural crest-like | KIAA1755 |
| ITGB8 | Neural crest-like | Integrin, beta 8 |
| IER3 | Neural crest-like | Immediate early response 3 |
| HHEX | Neural crest-like | Hematopoietically expressed homeobox |
| GDNF | Neural crest-like | Glial cell derived neurotrophic factor |
| GLI2 | Neural crest-like | GLI family zinc finger 2 |
| FOXC2 | Neural crest-like | Forkhead box C2 (MFH-1, mesenchyme forkhead 1) |
| FLT1 | Neural crest-like | Fms-related tyrosine kinase 1 (vascular endothelial growth factor/vascular permeability factor receptor) |
| FAT3 | Neural crest-like | FAT tumor suppressor homolog 3 (*Drosophila*) |

TABLE S4-continued

Subtype Signatures, Differentially Upregulated Genes

| Gene | Signature | Description |
| --- | --- | --- |
| FEZ1 | Neural crest-like | Fasciculation and elongation protein zeta 1 (zygin I) |
| FAM135B | Neural crest-like | Family with sequence similarity 135, member B |
| EHF | Neural crest-like | Ets homologous factor |
| EML1 | Neural crest-like | Echinoderm microtubule associated protein like 1 |
| DRD2 | Neural crest-like | Dopamine receptor D2 |
| DEPDC7 | Neural crest-like | DEP domain containing 7 |
| CYB5R2 | Neural crest-like | Cytochrome b5 reductase 2 |
| CSRP2 | Neural crest-like | Cysteine and glycine-rich protein 2 |
| CCL2 | Neural crest-like | Chemokine (C-C motif) ligand 2 |
| CADM3 | Neural crest-like | Cell adhesion molecule 3 |
| CADM1 | Neural crest-like | Cell adhesion molecule 1 |
| CD96 | Neural crest-like | CD96 molecule |
| CTSS | Neural crest-like | Cathepsin S |
| CHST2 | Neural crest-like | Carbohydrate (N-acetylglucosamine-6-O) sulfotransferase 2 |
| CHST1 | Neural crest-like | Carbohydrate (keratan sulfate Gal-6) sulfotransferase 1 |
| CACNA2D3 | Neural crest-like | Calcium channel, voltage-dependent, alpha 2/delta subunit 3 |
| BST1 | Neural crest-like | Bone marrow stromal cell antigen 1 |
| ABCA6 | Neural crest-like | ATP-binding cassette, sub-family A (ABC1), member 6 |
| ANGPTL4 | Neural crest-like | Angiopoietin-like 4 |
| AIM2 | Neural crest-like | Absent in melanoma 2 |
| SPRY4 | Neural crest-like-Transitory | Sprouty homolog 4 (*Drosophila*) |
| SORCS1 | Neural crest-like-Transitory | Sortilin-related VPS10 domain containing receptor 1 |
| SLC35F1 | Neural crest-like-Transitory | Solute carrier family 35, member F1 |
| SERPINA5 | Neural crest-like-Transitory | Serpin peptidase inhibitor, clade A (alpha-1 antiproteinase, antitrypsin), member 5 |
| RFTN2 | Neural crest-like-Transitory | Raftlin family member 2 |
| PCDH1 | Neural crest-like-Transitory | Protocadherin 1 |
| PTPRZ1 | Neural crest-like-Transitory | Protein tyrosine phosphatase, receptor-type, Z polypeptide 1 |
| PRICKLE2 | Neural crest-like-Transitory | Prickle homolog 2 (*Drosophila*) |
| OLIG2 | Neural crest-like-Transitory | Oligodendrocyte lineage transcription factor 2 |
| LOXL4 | Neural crest-like-Transitory | Lysyl oxidase-like 4 |
| LOXL3 | Neural crest-like-Transitory | Lysyl oxidase-like 3 |
| LGI4 | Neural crest-like-Transitory | Leucine-rich repeat LGI family, member 4 |
| LAMA4 | Neural crest-like-Transitory | Laminin, alpha 4 |
| GAS7 | Neural crest-like-Transitory | Growth arrest-specific 7 |
| GRIK2 | Neural crest-like-Transitory | Glutamate receptor, ionotropic, kainate 2 |
| FREM2 | Neural crest-like-Transitory | FRAS1 related extracellular matrix protein 2 |
| FREM1 | Neural crest-like-Transitory | FRAS1 related extracellular matrix 1 |
| EPHB3 | Neural crest-like-Transitory | EPH receptor B3 |
| CRIP2 | Neural crest-like-Transitory | Cysteine-rich protein 2 |
| COL4A1 | Neural crest-like-Transitory | Collagen, type IV, alpha 1 |
| CADM4 | Neural crest-like-Transitory | Cell adhesion molecule 4 |
| BAALC | Neural crest-like-Transitory | Brain and acute leukemia, cytoplasmic |
| ABCA8 | Neural crest-like-Transitory | ATP-binding cassette, sub-family A (ABC1), member 8 |
| AGMO | Neural crest-like-Transitory | Alkylglycerol monooxygenase |
| ALDH1A3 | Neural crest-like-Transitory | Aldehyde dehydrogenase 1 family, member A3 |
| XYLT1 | Transitory | Xylosyltransferase I |
| TSPAN7 | Transitory | Tetraspanin 7 |
| SOD3 | Transitory | Superoxide dismutase 3, extracellular |
| SCRG1 | Transitory | Stimulator of chondrogenesis 1 |
| SORL1 | Transitory | Sortilin-related receptor, L(DLR class) A repeats containing |
| SEMA3E | Transitory | Sema domain, immunoglobulin domain (Ig), short basic domain, secreted, (semaphorin) 3E |
| SELENBP1 | Transitory | Selenium binding protein 1 |
| RNASE1 | Transitory | Ribonuclease, RNase A family, 1 (pancreatic) |
| RAPGEF4 | Transitory | Rap guanine nucleotide exchange factor (GEF) 4 |
| PCDH7 | Transitory | Protocadherin 7 |
| PRSS33 | Transitory | Protease, serine, 33 |
| PCSK6 | Transitory | Proprotein convertase subtilisin/kexin type 6 |
| PLBD1 | Transitory | Phospholipase B domain containing 1 |
| NELL1 | Transitory | NEL-like 1 (chicken) |
| NPR1 | Transitory | Natriuretic peptide receptor A/guanylate cyclase A (atrionatriuretic peptide receptor A) |

TABLE S4-continued

Subtype Signatures, Differentially Upregulated Genes

| Gene | Signature | Description |
|---|---|---|
| MCAM | Transitory | Melanoma cell adhesion molecule |
| MMP15 | Transitory | Matrix metallopeptidase 15 (membrane-inserted) |
| MAMDC2 | Transitory | MAM domain containing 2 |
| LSAMP | Transitory | Limbic system-associated membrane protein |
| LRRTM4 | Transitory | Leucine rich repeat transmembrane neuronal 4 |
| GDF11 | Transitory | Growth differentiation factor 11 |
| FXYD3 | Transitory | FXYD domain containing ion transport regulator 3 |
| EBF3 | Transitory | Early B-cell factor 3 |
| COL11A2 | Transitory | Collagen, type XI, alpha 2 |
| COL9A1 | Transitory | Collagen, type IX, alpha 1 |
| CX3CL1 | Transitory | Chemokine (C-X3-C motif) ligand 1 |
| BCHE | Transitory | Butyrylcholinesterase |
| ANO4 | Transitory | Anoctamin 4 |
| ALDH1A1 | Transitory | Aldehyde dehydrogenase 1 family, member A1 |
| ADGRG1 | Transitory-Melanocytic | Adhesion G Protein-Coupled Receptor G1 |
| MOB3B | Transitory-Melanocytic | MOB kinase activator 3B |
| SEPT4 | Transitory-Melanocytic | septin 4 |
| TUBB4A | Transitory-Melanocytic | tubulin, beta 4A class IVa |
| UBAP1L | Transitory-Melanocytic | Ubiquitin Associated Protein 1 Like |
| ZNF704 | Transitory-Melanocytic | Zinc finger protein 704 |
| WFDC1 | Transitory-Melanocytic | WAP four-disulfide core domain 1 |
| VGF | Transitory-Melanocytic | VGF nerve growth factor inducible |
| VAT1 | Transitory-Melanocytic | Vesicle amine transport protein 1 homolog (*T. californica*) |
| GALNT3 | Transitory-Melanocytic | UDP-N-acetyl-alpha-D-galactosamine:polypeptide N-acetylgalactosaminyltransferase 3 (GalNAc-T3) |
| UGT2B7 | Transitory-Melanocytic | UDP glucuronosyltransferase 2 family, polypeptide B7 |
| TYRP1 | Transitory-Melanocytic | Tyrosinase-related protein 1 |
| TYR | Transitory-Melanocytic | Tyrosinase (oculocutaneous albinism IA) |
| TTYH2 | Transitory-Melanocytic | Tweety homolog 2 (*Drosophila*) |
| TMC6 | Transitory-Melanocytic | Transmembrane channel-like 6 |
| TMCC2 | Transitory-Melanocytic | Transmembrane and coiled-coil domain family 2 |
| TBC1D7 | Transitory-Melanocytic | TBC1 domain family, member 7 |
| TBC1D16 | Transitory-Melanocytic | TBC1 domain family, member 16 |
| STXBP6 | Transitory-Melanocytic | Syntaxin binding protein 6 (amisyn) |
| ST8SIA1 | Transitory-Melanocytic | ST8 alpha-N-acetyl-neuraminide alpha-2,8-sialyltransferase 1 |
| ST3GAL6 | Transitory-Melanocytic | ST3 beta-galactoside alpha-2,3-sialyltransferase 6 |
| SOX6 | Transitory-Melanocytic | SRY (sex determining region Y)-box 6 |
| SLC5A4 | Transitory-Melanocytic | Solute carrier family 5 (low affinity glucose cotransporter), member 4 |
| SLC45A2 | Transitory-Melanocytic | Solute carrier family 45, member 2 |
| SLC27A3 | Transitory-Melanocytic | Solute carrier family 27 (fatty acid transporter), member 3 |
| SLC24A5 | Transitory-Melanocytic | Solute carrier family 24, member 5 |
| SIRPA | Transitory-Melanocytic | Signal-regulatory protein alpha |
| SCUBE2 | Transitory-Melanocytic | Signal peptide, CUB domain, EGF-like 2 |
| STK32A | Transitory-Melanocytic | Serine/threonine kinase 32A |
| RLBP1 | Transitory-Melanocytic | Retinaldehyde binding protein 1 |
| RENBP | Transitory-Melanocytic | Renin binding protein |
| RRAGD | Transitory-Melanocytic | Ras-related GTP binding D |
| RASSF3 | Transitory-Melanocytic | Ras association (RalGDS/AF-6) domain family member 3 |
| RAP1GAP | Transitory-Melanocytic | RAP1 GTPase activating protein |
| RAB38 | Transitory-Melanocytic | RAB38, member RAS oncogene family |
| QDPR | Transitory-Melanocytic | Quinoid dihydropteridine reductase |
| P2RX7 | Transitory-Melanocytic | Purinergic receptor P2X, ligand-gated ion channel, 7 |
| PRR5 | Transitory-Melanocytic | Proline rich 5 (renal) |
| PMEL | Transitory-Melanocytic | Premelanosome protein |
| PLXNC1 | Transitory-Melanocytic | Plexin C1 |
| PLEKHH1 | Transitory-Melanocytic | Pleckstrin homology domain containing, family H (with MyTH4 domain) member 1 |
| PLA1A | Transitory-Melanocytic | Phospholipase A1 member A |
| PDE3B | Transitory-Melanocytic | Phosphodiesterase 3B, cGMP-inhibited |
| PHACTR1 | Transitory-Melanocytic | Phosphatase and actin regulator 1 |
| PPARGC1A | Transitory-Melanocytic | Peroxisome proliferator-activated receptor gamma, coactivator 1 alpha |

TABLE S4-continued

Subtype Signatures, Differentially Upregulated Genes

| Gene | Signature | Description |
| --- | --- | --- |
| PMP2 | Transitory-Melanocytic | Peripheral myelin protein 2 |
| PI15 | Transitory-Melanocytic | Peptidase inhibitor 15 |
| OGDHL | Transitory-Melanocytic | Oxoglutarate dehydrogenase-like |
| NRG3 | Transitory-Melanocytic | Neuregulin 3 |
| NKAIN4 | Transitory-Melanocytic | Na+/K+ transporting ATPase interacting 4 |
| ASAH1 | Transitory-Melanocytic | N-acylsphingosine amidohydrolase (acid ceramidase) 1 |
| NAT8L | Transitory-Melanocytic | N-acetyltransferase 8-like (GCN5-related, putative) |
| GNPTAB | Transitory-Melanocytic | N-acetylglucosamine-1-phosphate transferase, alpha and beta subunits |
| MYO10 | Transitory-Melanocytic | Myosin X |
| MBP | Transitory-Melanocytic | Myelin basic protein |
| MCC | Transitory-Melanocytic | Mutated in colorectal cancers |
| MITF | Transitory-Melanocytic | Microphthalmia-associated transcription factor |
| MFAP3L | Transitory-Melanocytic | Microfibrillar-associated protein 3-like |
| LDB3 | Transitory-Melanocytic | LIM domain binding 3 |
| LRGUK | Transitory-Melanocytic | Leucine-rich repeats and guanylate kinase domain containing |
| LGI3 | Transitory-Melanocytic | Leucine-rich repeat LGI family, member 3 |
| LINGO1 | Transitory-Melanocytic | Leucine rich repeat and Ig domain containing 1 |
| LGALS3 | Transitory-Melanocytic | Lectin, galactoside-binding, soluble, 3 |
| LAMC3 | Transitory-Melanocytic | Laminin, gamma 3 |
| LAMA1 | Transitory-Melanocytic | Laminin, alpha 1 |
| KLF15 | Transitory-Melanocytic | Kruppel-like factor 15 |
| KAZN | Transitory-Melanocytic | Kazrin, periplakin interacting protein |
| IRX6 | Transitory-Melanocytic | Iroquois homeobox 6 |
| IRF4 | Transitory-Melanocytic | Interferon regulatory factor 4 |
| INPP4B | Transitory-Melanocytic | Inositol polyphosphate-4-phosphatase, type II, 105 kDa |
| ID4 | Transitory-Melanocytic | Inhibitor of DNA binding 4, dominant negative helix-loop-helix protein |
| IGSF11 | Transitory-Melanocytic | Immunoglobulin superfamily, member 11 |
| HAS2 | Transitory-Melanocytic | Hyaluronan synthase 2 |
| HPS4 | Transitory-Melanocytic | Hermansky-Pudlak syndrome 4 |
| GREB1 | Transitory-Melanocytic | Growth regulation by estrogen in breast cancer 1 |
| GHR | Transitory-Melanocytic | Growth hormone receptor |
| GDF15 | Transitory-Melanocytic | Growth differentiation factor 15 |
| GAB2 | Transitory-Melanocytic | GRB2-associated binding protein 2 |
| GPM6B | Transitory-Melanocytic | Glycoprotein M6B |
| GPNMB | Transitory-Melanocytic | Glycoprotein (transmembrane) nmb |
| GYPC | Transitory-Melanocytic | Glycophorin C (Gerbich blood group) |
| GYG2 | Transitory-Melanocytic | Glycogenin 2 |
| GAPDHS | Transitory-Melanocytic | Glyceraldehyde-3-phosphate dehydrogenase, spermatogenic |
| GJB1 | Transitory-Melanocytic | Gap junction protein, beta 1, 32 kDa |
| GPRC5B | Transitory-Melanocytic | G protein-coupled receptor, family C, group 5, member B |
| FMN1 | Transitory-Melanocytic | Formin 1 |
| FCGR2B | Transitory-Melanocytic | Fc fragment of IgG, low affinity IIb, receptor (CD32) |
| FCER1G | Transitory-Melanocytic | Fc fragment of IgE, high affinity I, receptor for; gamma polypeptide |
| FAM69C | Transitory-Melanocytic | Family with sequence similarity 69, member C |
| FAM167B | Transitory-Melanocytic | Family with sequence similarity 167, member B |
| ESRP1 | Transitory-Melanocytic | Epithelial splicing regulatory protein 1 |
| DUSP15 | Transitory-Melanocytic | Dual specificity phosphatase 15 |
| DSTYK | Transitory-Melanocytic | Dual serine/threonine and tyrosine protein kinase |
| DCT | Transitory-Melanocytic | Dopachrome tautomerase (dopachrome delta-isomerase, tyrosine-related protein 2) |
| D4S234E | Transitory-Melanocytic | DNA segment on chromosome 4 (unique) 234 expressed sequence |
| DAPK1 | Transitory-Melanocytic | Death-associated protein kinase 1 |
| CDK5R1 | Transitory-Melanocytic | Cyclin-dependent kinase 5, regulatory subunit 1 (p35) |
| CELF2 | Transitory-Melanocytic | CUGBP, Elav-like family member 2 |
| CTTNBP2 | Transitory-Melanocytic | Cortactin binding protein 2 |
| CHCHD6 | Transitory-Melanocytic | Coiled-coil-helix-coiled-coil-helix domain containing 6 |

TABLE S4-continued

Subtype Signatures, Differentially Upregulated Genes

| Gene | Signature | Description |
| --- | --- | --- |
| CHCHD10 | Transitory-Melanocytic | Coiled-coil-helix-coiled-coil-helix domain containing 10 |
| C11orf96 | Transitory-Melanocytic | Chromosome 11 open reading frame 96 |
| CHN2 | Transitory-Melanocytic | Chimerin (chimaerin) 2 |
| CHL1 | Transitory-Melanocytic | Cell adhesion molecule with homology to L1CAM (close homolog of L1) |
| CITED1 | Transitory-Melanocytic | Cbp/p300-interacting transactivator, with Glu/Asp-rich carboxy-terminal domain, 1 |
| CARD14 | Transitory-Melanocytic | Caspase recruitment domain family, member 14 |
| CPN1 | Transitory-Melanocytic | Carboxypeptidase N, polypeptide 1 |
| CA14 | Transitory-Melanocytic | Carbonic anhydrase XIV |
| CAPN3 | Transitory-Melanocytic | Calpain 3, (p94) |
| MERTK | Transitory-Melanocytic | C-mer proto-oncogene tyrosine kinase |
| BCAS3 | Transitory-Melanocytic | Breast carcinoma amplified sequence 3 |
| BEST1 | Transitory-Melanocytic | Bestrophin 1 |
| BCL2A1 | Transitory-Melanocytic | BCL2-related protein A1 |
| BIRC7 | Transitory-Melanocytic | Baculoviral IAP repeat containing 7 |
| ATP6V0A4 | Transitory-Melanocytic | ATPase, H+ transporting, lysosomal V0 subunit a4 |
| ATP10A | Transitory-Melanocytic | ATPase, class V, type 10A |
| APOE | Transitory-Melanocytic | Apolipoprotein E |
| APOC1 | Transitory-Melanocytic | Apolipoprotein C-I |
| ASB2 | Transitory-Melanocytic | Ankyrin repeat and SOCS box containing 2 |
| ANK2 | Transitory-Melanocytic | Ankyrin 2, neuronal |
| ADRBK2 | Transitory-Melanocytic | Adrenergic, beta, receptor kinase 2 |
| ADCY1 | Transitory-Melanocytic | Adenylate cyclase 1 (brain) |
| ACP5 | Transitory-Melanocytic | Acid phosphatase 5, tartrate resistant |
| PFKFB2 | Transitory-Melanocytic | 6-phosphofructo-2-kinase/fructose-2,6-biphosphatase 2 |
| HTR2B | Transitory-Melanocytic | 5-hydroxytryptamine (serotonin) receptor 2B |
| CCDC171 | Melanocytic | Coiled-Coil Domain Containing 171 |
| CFAP61 | Melanocytic | cilia and flagella associated protein 61 |
| ZDHHC11B | Melanocytic | Zinc finger, DHHC-type containing 11B |
| VEPH1 | Melanocytic | Ventricular zone expressed PH domain homolog 1 (zebrafish) |
| TNFRSF14 | Melanocytic | Tumor necrosis factor receptor superfamily, member 14 (herpesvirus entry mediator) |
| TDRD3 | Melanocytic | Tudor domain containing 3 |
| TPPP | Melanocytic | Tubulin polymerization promoting protein |
| TRIM63 | Melanocytic | Tripartite motif containing 63 |
| TRPM1 | Melanocytic | Transient receptor potential cation channel, subfamily M, member 1 |
| TTC39A | Melanocytic | Tetratricopeptide repeat domain 39A |
| TSPAN10 | Melanocytic | Tetraspanin 10 |
| SLC7A8 | Melanocytic | Solute carrier family 7 (amino acid transporter, L-type), member 8 |
| SLC16A6 | Melanocytic | Solute carrier family 16, member 6 (monocarboxylic acid transporter 7) |
| SLAMF7 | Melanocytic | SLAM family member 7 |
| SEMA6A | Melanocytic | Sema domain, transmembrane domain (TM), and cytoplasmic domain, (semaphorin) 6A |
| RUNX3 | Melanocytic | Runt-related transcription factor 3 |
| RNF144B | Melanocytic | Ring finger protein 144B |
| RNLS | Melanocytic | Renalase, FAD-dependent amine oxidase |
| RGS12 | Melanocytic | Regulator of G-protein signaling 12 |
| PYCARD | Melanocytic | PYD and CARD domain containing |
| PRUNE2 | Melanocytic | Prune homolog 2 (*Drosophila*) |
| PRKCB | Melanocytic | Protein kinase C, beta |
| PRDM7 | Melanocytic | PR domain containing 7 |
| KCNAB2 | Melanocytic | Potassium voltage-gated channel, shaker-related subfamily, beta member 2 |
| OCA2 | Melanocytic | Oculocutaneous albinism II |
| NR4A3 | Melanocytic | Nuclear receptor subfamily 4, group A, member 3 |
| NAV2 | Melanocytic | Neuron navigator 2 |
| MYO1D | Melanocytic | Myosin ID |
| MAPK4 | Melanocytic | Mitogen-activated protein kinase 4 |
| MAT1A | Melanocytic | Methionine adenosyltransferase I, alpha |
| MLANA | Melanocytic | Melan-A |
| LXN | Melanocytic | Latexin |
| KCP | Melanocytic | Kielin/chordin-like protein |
| IL16 | Melanocytic | Interleukin 16 (lymphocyte chemoattractant factor) |
| IL12RB2 | Melanocytic | Interleukin 12 receptor, beta 2 |
| HSD17B14 | Melanocytic | Hydroxysteroid (17-beta) dehydrogenase 14 |

TABLE S4-continued

Subtype Signatures, Differentially Upregulated Genes

| Gene | Signature | Description |
| --- | --- | --- |
| HMOX1 | Melanocytic | Heme oxygenase (decycling) 1 |
| H2AFJ | Melanocytic | H2A histone family, member J |
| GOLGA7B | Melanocytic | Golgin A7 family, member B |
| QPCT | Melanocytic | Glutaminyl-peptide cyclotransferase |
| GFOD1 | Melanocytic | Glucose-fructose oxidoreductase domain containing 1 |
| GPR143 | Melanocytic | G protein-coupled receptor 143 |
| FYB | Melanocytic | FYN binding protein |
| FAM83H | Melanocytic | Family with sequence similarity 83, member H |
| FAM174B | Melanocytic | Family with sequence similarity 174, member B |
| EPHA5 | Melanocytic | EPH receptor A5 |
| ENTHD1 | Melanocytic | ENTH domain containing 1 |
| DNAJA4 | Melanocytic | DnaJ (Hsp40) homolog, subfamily A, member 4 |
| DENND2D | Melanocytic | DENN/MADD domain containing 2D |
| C2orf88 | Melanocytic | Chromosome 2 open reading frame 88 |
| CCL18 | Melanocytic | Chemokine (C-C motif) ligand 18 (pulmonary and activation-regulated) |
| CEACAM1 | Melanocytic | Carcinoembryonic antigen-related cell adhesion molecule 1 (biliary glycoprotein) |
| CAPG | Melanocytic | Capping protein (actin filament), gelsolin-like |
| CDH3 | Melanocytic | Cadherin 3, type 1, P-cadherin (placental) |
| CDH1 | Melanocytic | Cadherin 1, type 1, E-cadherin (epithelial) |
| ATP6V0D2 | Melanocytic | ATPase, H+ transporting, lysosomal 38 kDa, V0 subunit d2 |
| ABCD1 | Melanocytic | ATP-binding cassette, sub-family D (ALD), member 1 |
| ABCB5 | Melanocytic | ATP-binding cassette, sub-family B (MDR/TAP), member 5 |
| APOLD1 | Melanocytic | Apolipoprotein L domain containing 1 |
| ANKRD30B | Melanocytic | Ankyrin repeat domain 30B |
| ADCY2 | Melanocytic | Adenylate cyclase 2 (brain) |
| ADAM23 | Melanocytic | ADAM metallopeptidase domain 23 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references and the publications referred to throughout the specification, to the extent that they provide exemplary procedural or other details supplementary to those set forth herein, are specifically incorporated herein by reference.

Barretina, J. Caponigro, G., Stransky, N., Venkatesan, K., Margolin, A. A., Kim, S., Wilson, C. J., Lehár, J., Kryukov, G. V., Sonkin, D., Reddy, A., Liu, M., Murray, L., Berger, M. F., Monahan, J. E., Morais, P., Meltzer, J., Korejwa, A., Jané-Valbuena, J., Mapa, F. A., Thibault, J., Bric-Furlong, E., Raman, P., Shipway, A., Engels, I. H., Cheng, J., Yu, G. K., Yu, J., Aspesi, P., de Silva, M., Jagtap, K., Jones, M. D., Wang, L., Hatton, C., Palescandolo, E., et al. (2012). The Cancer Cell Line Encyclopedia enables predictive modelling of anticancer drug sensitivity. Nature 483, 603-607.

Chen, Y., Lemire, M., Choufani, S., Butcher, D. T., Grafodatskaya, D., Zanke, B. W., Gallinger, S., Hudson, T. J., and Weksberg, R. (2013). Discovery of cross-reactive probes and polymorphic CpGs in the Illumina Infinium HumanMethylation450 microarray. Epigenetics 8, 203-209.

Denat, L., Kadekaro, A. L., Marrot, L., Leachman, S. A., and Abdel-Malek, Z. A. (2014). Melanocytes as Instigators and Victims of Oxidative Stress. Journal of Investigative Dermatology 134, 1512-1518.

Dixon, S. J., Lemberg, K. M., Lamprecht, M. R., Skouta, R., Zaitsev, E. M., Gleason, C. E., Patel, D. N., Bauer, A. J., Cantley, A. M., Yang, W. S., Morrison, B., and Stockwell, B. R. (2012). Ferroptosis: An Iron-Dependent Form of Nonapoptotic Cell Death. Cell 149, 1060-1072.

Dolma, S., Lessnick, S. L., Hahn, W. C., and Stockwell, B. R. (2003). Identification of genotype-selective antitumor agents using synthetic lethal chemical screening in engineered human tumor cells. Cancer Cell 3, 285-296.

Doxsee, D. W., Gout, P. W., Kurita, T., Lo, M., Buckley, A. R., Wang, Y., Xue, H., Karp, C. M., Cutz, J.-C., Cunha, G. R., and Wang, Y.-Z. (2007). Sulfasalazine-induced cystine starvation: Potential use for prostate cancer therapy. Prostate 67, 162-171.

Eroglu, Z., and Ribas, A. (2016). Combination therapy with BRAF and MEK inhibitors for melanoma: latest evidence and place in therapy. Therapeutic Advances in Medical Oncology 8, 48-56.

Girotti, M. R., Pedersen, M., Sanchez-Laorden, B., Viros, A., Turajlic, S., Niculescu-Duvaz, D., Zambon, A., Sinclair, J., Hayes, A., Gore, M., Lorigan, P., Springer, C., Larkin, J., Jorgensen, C., and Marais, R. (2013). Inhibiting EGF Receptor or SRC Family Kinase Signaling Overcomes BRAF Inhibitor Resistance in Melanoma. Cancer Discovery 3, 158-167.

Gorrini, C., Harris, I. S., and Mak, T. W. (2013). Modulation of oxidative stress as an anticancer strategy. Nat Rev Drug Discov 12, 931-947.

Guo, W., Zhao, Y., Zhang, Z., Tan, N., Zhao, F., Ge, C., Liang, L., Jia, D., Chen, T., Yao, M., Li, J., and He, X. (2011). Disruption of xCT inhibits cell growth via the ROS/autophagy pathway in hepatocellular carcinoma. Cancer Letters 312, 55-61.

Hansen, K. D., Irizarry, R. A., and Wu, Z. (2012). Removing technical variability in RNA-seq data using conditional quantile normalization. Biostat 13, 204-216.

Hoek, K. S., Schlegel, N. C., Brafford, P., Sucker, A., Ugurel, S., Kumar, R., Weber, B. L., Nathanson, K. L., Phillips, D. J., Herlyn, M., Schadendorf, D., and Dummer, R. (2006). Metastatic potential of melanomas defined by specific gene expression profiles with no BRAF signature. Pigment Cell Research 19, 290-302.

Hoek, K. S., Schlegel, N. C., Eichhoff, O. M., Widmer, D. S., Praetorius, C., Einarsson, S. O., Valgeirsdottir, S., Bergsteinsdottir, K., Schepsky, A., Dummer, R., and Steingrimsson, E. (2008). Novel MITF targets identified using a two-step DNA microarray strategy. Pigment Cell & Melanoma Research 21, 665-676.

Hugo, W., Shi, H., Sun, L., Piva, M., Song, C., Kong, X., Moriceau, G., Hong, A., Dahlman, K. B., Johnson, D. B., Sosman, J. A., Ribas, A., and Lo, R. S. (2015). Non-genomic and Immune Evolution of Melanoma Acquiring MAPKi Resistance. Cell 162, 1271-1285.

Iorio, F., Knijnenburg, T. A., Vis, D. J., Bignell, G. R., Menden, M. P., Schubert, M., Aben, N., Gonçalves, E., Barthorpe, S., Lightfoot, H., Cokelaer, T., Greninger, P., van Dyk, E., Chang, H., de Silva, H., Heyn, H., Deng, X., Egan, R. K., Liu, Q., Mironenko, T., Mitropoulos, X., Richardson, L., Wang, J., Zhang, T., Moran, S., Sayols, S., Soleimani, M., Tamborero, D., Lopez-Bigas, N., Ross-Macdonald, P., Esteller, M., Gray, N. S., Haber, D. A., Stratton, M. R., Benes, C. H., et al. (2016). A Landscape of Pharmacogenomic Interactions in Cancer. Cell 166, 740-754.

Iwai, Y., Ishida, M., Tanaka, Y., Okazaki, T., Honjo, T., and Minato, N. (2002). Involvement of PD-L1 on tumor cells in the escape from host immune system and tumor immunotherapy by PD-L1 blockade. PNAS 99, 12293-12297.

Kawakami, Y., Dang, N., Wang, X., Tupesis, J., Robbins, P. F., Wang, R. F., Wunderlich, J. R., Yannelli, J. R., and Rosenberg, S. A. Recognition of shared melanoma antigens in association with major H1a-a alleles by tumor infiltrating T lymphocytes from 123 patients with melanoma. J. Immunother. 23, 17-27.

Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome Biology 14, R36.

Konieczkowski, D. J., Johannessen, C. M., Abudayyeh, O., Kim, J. W., Cooper, Z. A., Piris, A., Frederick, D. T., Barzily-Rokni, M., Straussman, R., Haq, R., Fisher, D. E., Mesirov, J. P., Hahn, W. C., Flaherty, K. T., Wargo, J. A., Tamayo, P., and Garraway, L. A. (2014). A Melanoma Cell State Distinction Influences Sensitivity to MAPK Pathway Inhibitors. Cancer Discovery 4, 816-827.

Kwong, L. N., Boland, G. M., Frederick, D. T., Helms, T. L., Akid, A. T., Miller, J. P., Jiang, S., Cooper, Z. A., Song, X., Seth, S., Kamara, J., Protopopov, A., Mills, G. B., Flaherty, K. T., Wargo, J. A., and Chin, L. (2015). Co-clinical assessment identifies patterns of BRAF inhibitor resistance in melanoma. Journal of Clinical Investigation 125, 1459-1470.

Landsberg, J., Kohlmeyer, J., Renn, M., Bald, T., Rogava, M., Cron, M., Fatho, M., Lennerz, V., Wölfel, T., Hölzel, M., and Tüting, T. (2012). Melanomas resist T-cell therapy through inflammation-induced reversible dedifferentiation. Nature 490, 412-416.

Lauss, M., Haq, R., Cirenajwis, H., Phung, B., Harbst, K., Staaf, J., Rosengren, F., Holm, K., Aine, M., Jirström, K., Borg, Å., Busch, C., Geisler, J., Lønning, P. E., Ringnér, M., Howlin, J., Fisher, D. E., and Jonsson, G. (2015). Genome-Wide DNA Methylation Analysis in Melanoma Reveals the Importance of CpG Methylation in MITF Regulation. Journal of Investigative Dermatology 135, 1820-1828.

Liu, F., Fu, Y., and Meyskens Jr., F. L. (2009). MiTF Regulates Cellular Response to Reactive Oxygen Species through Transcriptional Regulation of APE-1/Ref-1. Journal of Investigative Dermatology 129, 422-431.

Liu, Y., Hayes, D. N., Nobel, A., and Marron, J. S. (2008). Statistical Significance of Clustering for High-Dimension, Low-Sample Size Data. Journal of the American Statistical Association 103, 1281-1293.

Lo, M., Wang, Y.-Z., and Gout, P. W. (2008). The x c-cystine/glutamate antiporter: A potential target for therapy of cancer and other diseases. J. Cell. Physiol. 215, 593-602.

Luke, J. J., Flaherty, K. T., Ribas, A., and Long, G. V. (2017). Targeted agents and immunotherapies: optimizing outcomes in melanoma. Nat Rev Clin Oncol advance online publication.

Mica, Y., Lee, G., Chambers, S. M., Tomishima, M. J., and Studer, L. (2013). Modeling Neural Crest Induction, Melanocyte Specification, and Disease-Related Pigmentation Defects in hESCs and Patient-Specific iPSCs. Cell Reports 3, 1140-1152.

Moll, R., Divo, M., and Langbein, L. (2008). The human keratins: biology and pathology. Histochem Cell Biot 129, 705-733.

Monti, S., Tamayo, P., Mesirov, J., and Golub, T. (2003). Consensus Clustering: A Resampling-Based Method for Class Discovery and Visualization of Gene Expression Microarray Data. Machine Learning 52, 91-118.

Müller, J., Krijgsman, O., Tsoi, J., Robert, L., Hugo, W., Song, C., Kong, X., Possik, P. A., Cornelissen-Steijger, P. D. M., Foppen, M. H. G., Kemper, K., Goding, C. R., McDermott, U., Blank, C., Haanen, J., Graeber, T. G., Ribas, A., Lo, R. S., and Peeper, D. S. (2014). Low MITF/AXL ratio predicts early resistance to multiple targeted drugs in melanoma. Nat Commun 5, 5712.

Natarajan, V. T., Ganju, P., Singh, A., Vijayan, V., Kirty, K., Yadav, S., Puntambekar, S., Bajaj, S., Dani, P. P., Kar, H. K., Gadgil, C. J., Natarajan, K., Rani, R., and Gokhale, R. S. (2014). IFN-γ signaling maintains skin pigmentation homeostasis through regulation of melanosome maturation. Proc Natl Acad Sci USA 111, 2301-2306.

Nazarian, R., Shi, H., Wang, Q., Kong, X., Koya, R. C., Lee, H., Chen, Z., Lee, M.-K., Attar, N., Sazegar, H., Chodon, T., Nelson, S. F., McArthur, G., Sosman, J. A., Ribas, A., and Lo, R. S. (2010). Melanomas acquire resistance to B-RAF (V600E) inhibition by RTK or N-RAS upregulation. Nature 468, 973-977.

Piskounova, E., Agathocleous, M., Murphy, M. M., Hu, Z., Huddlestun, S. E., Zhao, Z., Leitch, A. M., Johnson, T. M., DeBerardinis, R. J., and Morrison, S. J. (2015). Oxidative stress inhibits distant metastasis by human melanoma cells. Nature 527, 186-191.

Raj, L., Ide, T., Gurkar, A. U., Foley, M., Schenone, M., Li, X., Tolliday, N. J., Golub, T. R., Carr, S. A., Shamji, A. F., Stern, A. M., Mandinova, A., Schreiber, S. L., and Lee, S. W. (2011). Selective killing of cancer cells by a small molecule targeting the stress response to ROS. Nature 475, 231-234.

Riesenberg, S., Groetchen, A., Siddaway, R., Bald, T., Reinhardt, J., Smorra, D., Kohlmeyer, J., Renn, M., Phung, B., Aymans, P., Schmidt, T., Hornung, V., Davidson, I., Goding, C. R., Jönsson, G., Landsberg, J., Tüting, T., and Hölzel, M. (2015). MITF and c-Jun antagonism interconnects melanoma dedifferentiation with pro-inflammatory cytokine responsiveness and myeloid cell recruitment. Nat Commun 6, 8755.

Rodeck, U., Nishiyama, T., and Mauviel, A. (1999). Independent Regulation of Growth and SMAD-mediated Transcription by Transforming Growth Factor f3 in Human Melanoma Cells. Cancer Res 59, 547-550.

Sauka-Spengler, T., and Bronner-Fraser, M. (2008). A gene regulatory network orchestrates neural crest formation. Nat Rev Mol Cell Biol 9, 557-568.

Schepsky, A., Bruser, K., Gunnarsson, G. J., Goodall, J., Hallsson, J. H., Goding, C. R., Steingrimsson, E., and Hecht, A. (2006). The Microphthalmia-Associated Transcription Factor Mitf Interacts with β-Catenin To Determine Target Gene Expression. Mol. Cell. Biol. 26, 8914-8927.

Seashore-Ludlow, B., Rees, M. G., Cheah, J. H., Cokol, M., Price, E. V., Coletti, M. E., Jones, V., Bodycombe, N. E., Soule, C. K., Gould, J., Alexander, B., Li, A., Montgomery, P., Wawer, M. J., Kuru, N., Kotz, J. D., Hon, C. S.-Y., Munoz, B., Liefeld, T., Dančík, V., Bittker, J. A., Palmer, M., Bradner, J. E., Shamji, A. F., Clemons, P. A., and Schreiber, S. L. (2015). Harnessing Connectivity in a Large-Scale Small-Molecule Sensitivity Dataset. Cancer Discov.

Shaffer, S. M., Dunagin, M. C., Torborg, S. R., Torre, E. A., Emert, B., Krepler, C., Beqiri, M., Sproesser, K., Brafford, P. A., Xiao, M., Eggan, E., Anastopoulos, I. N., Vargas-Garcia, C. A., Singh, A., Nathanson, K. L., Herlyn, M., and Raj, A. (2017). Rare cell variability and drug-induced reprogramming as a mode of cancer drug resistance. Nature advance online publication.

Shakhova, O., Zingg, D., Schaefer, S. M., Hari, L., Civenni, G., Blunschi, J., Claudinot, S., Okoniewski, M., Beermann, F., Mihic-Probst, D., Moch, H., Wegner, M., Dummer, R., Barrandon, Y., Cinelli, P., and Sommer, L. (2012). Sox10 promotes the formation and maintenance of giant congenital naevi and melanoma. Nat Cell Biol 14, 882-890.

Shi, P., Ray, S., Zhu, Q., and Kon, M. A. (2011). Top scoring pairs for feature selection in machine learning and applications to cancer outcome prediction. BMC Bioinformatics 12, 375.

Shimada, K., Hayano, M., Pagano, N. C., and Stockwell, B. R. (2016). Cell-Line Selectivity Improves the Predictive Power of Pharmacogenomic Analyses and Helps Identify NADPH as Biomarker for Ferroptosis Sensitivity. Cell Chemical Biology 23, 225-235.

Søndergaard, J. N., Nazarian, R., Wang, Q., Guo, D., Hsueh, T., Mok, S., Sazegar, H., MacConaill, L. E., Barretina, J. G., Kehoe, S. M., Attar, N., Euw, E. von, Zuckerman, J. E., Chmielowski, B., Comin-Anduix, B., Koya, R. C., Mischel, P. S., Lo, R. S., and Ribas, A. (2010). Differential sensitivity of melanoma cell lines with BRAF V600E mutation to the specific Raf inhibitor PLX4032. Journal of Translational Medicine 8, 39.

Soudja, S. M., Wehbe, M., Mas, A., Chasson, L., Tenbossche, C. P. de, Huijbers, I., Eynde, B. V. den, and Schmitt-Verhulst, A.-M. (2010). Tumor-Initiated Inflammation Overrides Protective Adaptive Immunity in an Induced Melanoma Model in Mice. Cancer Res 70, 3515-3525.

Subramanian, A., Tamayo, P., Mootha, V. K., Mukherjee, S., Ebert, B. L., Gillette, M. A., Paulovich, A., Pomeroy, S. L., Golub, T. R., Lander, E. S., and Mesirov, J. P. (2005). Gene set enrichment analysis: A knowledge-based approach for interpreting genome-wide expression profiles. PNAS 102, 15545-15550.

Sun, C., Wang, L., Huang, S., Heynen, G. J. J. E., Prahallad, A., Robert, C., Haanen, J., Blank, C., Wesseling, J., Willems, S. M., Zecchin, D., Hobor, S., Bajpe, P. K., Lieftink, C., Mateus, C., Vagner, S., Grernrum, W., Hofland, I., Schlicker, A., Wessels, L. F. A., Beijersbergen, R. L., Bardelli, A., Di Nicolantonio, F., Eggermont, A. M. M., and Bernards, R. (2014). Reversible and adaptive resistance to BRAF (V600E) inhibition in melanoma. Nature 508, 118-122.

Taube, J. M., Anders, R. A., Young, G. D., Xu, H., Sharma, R., McMiller, T. L., Chen, S., Klein, A. P., Pardoll, D. M., Topalian, S. L., and Chen, L. (2012). Colocalization of Inflammatory Response with B7-H1 Expression in Human Melanocytic Lesions Supports an Adaptive Resistance Mechanism of Immune Escape. Science Translational Medicine 4, 127ra37-127ra37.

Timmerman, L. A., Holton, T., Yuneva, M., Louie, R. J., Padró, M., Daemen, A., Hu, M., Chan, D. A., Ethier, S. P., van't Veer, L. J., Polyak, K., McCormick, F., and Gray, J. W. (2013). Glutamine Sensitivity Analysis Identifies the xCT Antiporter as a Common Triple-Negative Breast Tumor Therapeutic Target. Cancer Cell 24, 450-465.

Tirosh, I., Izar, B., Prakadan, S. M., Wadsworth, M. H., Treacy, D., Trombetta, J. J., Rotem, A., Rodman, C., Lian, C., Murphy, G., Fallahi-Sichani, M., Dutton-Regester, K., Lin, J.-R., Cohen, O., Shah, P., Lu, D., Genshaft, A. S., Hughes, T. K., Ziegler, C. G. K., Kazer, S. W., Gaillard, A., Kolb, K. E., Villani, A.-C., Johannessen, C. M., Andreev, A. Y., Allen, E. M. V., Bertagnolli, M., Sorger, P. K., Sullivan, R. J., Flaherty, K. T., Frederick, D. T., Jané-Valbuena, J., Yoon, C. H., Rozenblatt-Rosen, O., Shalek, A. K., et al. (2016). Dissecting the multicellular ecosystem of metastatic melanoma by single-cell RNA-seq. Science 352, 189-196.

Trapnell, C., Roberts, A., Goff, L., Pertea, G., Kim, D., Kelley, D. R., Pimentel, H., Salzberg, S. L., Rinn, J. L., and Pachter, L. (2012). Differential gene and transcript expression analysis of RNA-seq experiments with TopHat and Cufflinks. Nat. Protocols 7, 562-578.

Vazquez, F., Lim, J.-H., Chim, H., Bhalla, K., Girnun, G., Pierce, K., Clish, C. B., Granter, S. R., Widlund, H. R., Spiegelman, B. M., and Puig server, P. (2013). PGC1α Expression Defines a Subset of Human Melanoma Tumors with Increased Mitochondrial Capacity and Resistance to Oxidative Stress. Cancer Cell 23, 287-301.

Wong, D. J., Robert, L., Atefi, M. S., Lassen, A., Avarappatt, G., Cerniglia, M., Avramis, E., Tsoi, J., Foulad, D., Graeber, T. G., Comin-Anduix, B., Samatar, A., Lo, R. S., and Ribas, A. (2014). Antitumor activity of the ERK inhibitor SCH722984 against BRAF mutant, NRAS mutant and wild-type melanoma. Molecular Cancer 13, 194.

Xie, Y., Hou, W., Song, X., Yu, Y., Huang, J., Sun, X., Kang, R., and Tang, D. (2016). Ferroptosis: process and function. Cell Death Differ 23, 369-379.

Yagoda, N., von Rechenberg, M., Zaganjor, E., Bauer, A. J., Yang, W. S., Fridman, D. J., Wolpaw, A. J., Smukste, I., Peltier, J. M., Boniface, J. J., Smith, R., Lessnick, S. L., Sahasrabudhe, S., and Stockwell, B. R. (2007). RAS-RAF-MEK-dependent oxidative cell death involving voltage-dependent anion channels. Nature 447, 865-869.

Yang, W. S., and Stockwell, B. R. (2008). Synthetic Lethal Screening Identifies Compounds Activating Iron-Dependent, Nonapoptotic Cell Death in Oncogenic-RAS-Harboring Cancer Cells. Chemistry & Biology 15, 234-245.

Yang, W. S., SriRamaratnam, R., Welsch, M. E., Shimada, K., Skouta, R., Viswanathan, V. S., Cheah, J. H., Clemons, P. A., Shamji, A. F., Clish, C. B., Brown, L. M., Girotti, A. W., Cornish, V. W., Schreiber, S. L., and Stockwell, B. R. (2014). Regulation of Ferroptotic Cancer Cell Death by GPX4. Cell 156, 317-331.

Yang, W. S., Kim, K. J., Gaschler, M. M., Patel, M., Shchepinov, M. S., and Stockwell, B. R. (2016). Peroxidation of polyunsaturated fatty acids by lipoxygenases drives ferroptosis. PNAS 113, E4966-E4975.

What is claimed is:

1. A method for treating or preventing BRAF inhibitor resistance in a subject having dedifferentiated melanoma, the method comprising administering a GPX4 inhibitor and a BRAF inhibitor in parallel.

2. The method of claim 1, wherein the BRAF inhibitor comprises encorafenib, binimetinib, vemurafenib, or combinations thereof.

3. The method of claim 1, wherein the GPX4 inhibitor comprises a direct GPX4 inhibitor.

4. The method of claim 1, wherein the GPX4 inhibitor comprises one or more of RSL3, RSL5, ML162, ML210, DPI7, DPI10, DPI12, DPI13, DPI17, DPI18, DPI19, CIL56, FIN56, salts or derivatives thereof.

5. The method of claim 2, wherein the BRAF inhibitor comprises vemurafenib.

6. A method for treating a subject having dedifferentiated melanoma, the method comprising administering a GPX4 inhibitor to the subject, wherein the subject is being treated in parallel with a BRAF inhibitor.

7. The method of claim 6, wherein the BRAF inhibitor comprises encorafenib, binimetinib, vemurafenib, or combinations thereof.

8. The method of claim 7, wherein the BRAF inhibitor comprises vemurafenib.

9. The method of claim 6, wherein the GPX4 inhibitor comprises a direct GPX4 inhibitor.

10. The method of claim 6, wherein the GPX4 inhibitor comprises one or more of RSL3, RSL5, ML162, ML210, DPI7, DPI10, DPI12, DPI13, DPI17, DPI18, DPI19, CIL56, FIN56, salts or derivatives thereof.

11. The method of claim 6, wherein the subject has been determined to have melanoma cells with reduced expression of MITF; wherein the reduced expression of MITF is reduced compared to the level of expression of MITF in a cancerous sample with a melanocytic phenotype.

12. The method of claim 6, wherein the subject has been determined to have melanoma cells with reduced expression of MITF; wherein the reduced expression of MITF is reduced compared to the level of expression of MITF in a cancerous sample with a melanocytic phenotype.

* * * * *